(12) United States Patent
Prade et al.

(10) Patent No.: US 8,847,031 B2
(45) Date of Patent: Sep. 30, 2014

(54) THERMOCELLULASES FOR LIGNOCELLULOSIC DEGRADATION

(75) Inventors: Rolf A. Prade, Stillwater, OK (US); Hongliang Wang, Tempe, AZ (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 560 days.

(21) Appl. No.: 13/003,183

(22) PCT Filed: Jul. 9, 2009

(86) PCT No.: PCT/US2009/050080
§ 371 (c)(1),
(2), (4) Date: Apr. 8, 2011

(87) PCT Pub. No.: WO2010/006152
PCT Pub. Date: Jan. 14, 2010

(65) Prior Publication Data
US 2011/0183381 A1    Jul. 28, 2011

Related U.S. Application Data

(60) Provisional application No. 61/079,208, filed on Jul. 9, 2008.

(51) Int. Cl.
*A01H 5/00* (2006.01)
*C12N 9/42* (2006.01)
*C07H 21/04* (2006.01)

(52) U.S. Cl.
USPC ............... 800/320.1; 435/209; 536/23.2

(58) Field of Classification Search
USPC ............... 800/320.1; 435/209; 536/23.2
See application file for complete search history.

(56) References Cited

U.S. PATENT DOCUMENTS

| 2003/0129723 A1 | 7/2003 | Ishikawa et al. |
| 2006/0003433 A1 | 1/2006 | Steer et al. |
| 2006/0200877 A1 | 9/2006 | Lanahan et al. |
| 2009/0019608 A1 | 1/2009 | Lopez de Leon et al. |

FOREIGN PATENT DOCUMENTS

WO    WO 03018766 A2 *  3/2003

OTHER PUBLICATIONS

Frottin et al., "The proteomics of N-terminal methionine cleavage," Molecular and Cellular proteomics 5.12, pp. 2336-2349, 2006.*
Result 2, search of instant SEQ ID No. 2 in the protein Geneseq database, alignment with SEQ ID No. 55 of WO 03/018766 A2, performed on Jul. 5, 2013.*
Result 14, search of instant Seq ID No. 2 in the DNA Geneseq database, alignment with SEQ ID No. 56 of WO 03/018766 A2, performed on Jul. 5, 2013.*
Result 15, search of instant SEQ ID No. 2 in the DNA GenEmbl database, alignment w/ P. furiosus eg1A gene used in WO 03/018766A2, performed on Jul. 5, 2013.*

(Continued)

*Primary Examiner* — Rosanne Kosson
(74) *Attorney, Agent, or Firm* — Fellers, Snider, Blankenship, Bailey & Tippens, P.C.; Terry L. Watt

(57) ABSTRACT

Thermostable cellulase enzyme systems comprising at least one each of a thermostable endoglucanase, an exo-processive-endoglucanase, and a β-glucosidase carry out the complete, coordinated hydrolysis of crystalline cellulose to monomeric glucose.

3 Claims, 28 Drawing Sheets

High-temperature operating and thermo-stable cellulases

| PROTEIN | Source | | | Physical Properties | | | | | Functional Properties | | | | |
|---|---|---|---|---|---|---|---|---|---|---|---|---|---|
| | Locus | Codon Usage | CaZy | MW$_d$ | pI | Charge pH7 | T$^0$ °C | pH range | Mode of Operation | Specific Activity | | | |
| | | | | | | | | | | $_{sw}$Avicel | $_{av}$Cellulose | Paper | pNPG |
| Tcel1 | o-eglA | corn optimized | GH12 | 34,005 | 4.80 | -13.10 | 102 | 7 - 8 | exocellulase | 63.4 | 13.6 | 10.5 | - |
| Tcel2 | petroB | bacteria | GH12 | 31,816 | 4.77 | -13.30 | 98 | 6 - 7 | exocellulase | 8.1 | 2.2 | 2.9 | - |
| Tcel3 | ph1171 | archea | GH5 | 51,930 | 6.47 | -3.60 | 94 | 6 | exocellulase | 48.5 | 8.4 | 8.6 | - |
| Tcel4 | o-E1 | rice optimized | GH5 | 59,980 | 7.05 | 0.30 | 95 | 5 - 6 | endocellulase | 6.8 | 2.2 | 4.1 | - |
| Tcel5 | petroA | bacteria | GH12 | 38,226 | 5.58 | -6.60 | 96 | 5 - 6 | endocellulase | 34.1 | 6.8 | 8.0 | - |
| Tcel6 | zp#4 | corn optimized | GH12 | 31,818 | 5.66 | -5.00 | 85 | 5 - 6 | endocellulase | 20.6 | 5.1 | 5.1 | - |
| Tcel7 | Tpet0898 | bacteria | GH3 | 81,243 | 5.38 | -16.90 | 98 | 5 | beta-glucosidase | 0.8 | 0.8 | - | 69.4 |
| Tcel8 | Tpet0952 | bacteria | GH1 | 51,509 | 5.84 | -9.10 | 92 | 6 - 7 | beta-glucosidase | 1.7 | 1.5 | - | 60.9 |
| Tcel9 | g12#3 | corn optimized | GH12 | 45,059 | 6.16 | -2.20 | 85 | 5 - 6 | endocellulase | 5.2 | 1.4 | 7.5 | - |
| Tcel10 | ph0746 | archea | GH65 | 85,598 | 7.80 | 4.30 | 94 | 6 | endocellulase | 4.9 | 1.5 | 3.9 | - |

$_{sw}$AVICEL Phosphoric acid swollen Avicel, $_{av}$Cellulose, Avicel (Sigmacell): Cellulase specific activity, mM reducing sugar/mg protein/day at 85 °C, pH 6
Beta-glucosidase specific acitvity, nM pN/ug protein/min

(56) References Cited

OTHER PUBLICATIONS

Result 2, search of instant SEQ ID No. 1 in the DNA Geneseq database, alignment with SEQ ID No. 56 of WO 03/018766 A2, performed on Jul. 5, 2013.*
Sequence Listing, print copy from Score, printed Jan. 27, 2014.*
Ahlawat, et al., "Production of thermostable pectinase and xylanase for their potential application in bleaching of kraft pulp", 2007, pp. 763-770 (Abstract Only), vol. 34(12), Publisher: J Ind Microbiol Biotechnol, Published in: US.
GenBank ABQ46873, "URL: http://www.ncbi.nlm.nih.gov/protein/147735533", May 18, 2007, Publisher: GenBank—Online Retrieved from the NIH NCBI database using the internet.
GenBank CP000702, "URL: httb://www.ncbi.nlm.nih.gov/nuccore/147734689", May 18, 2007, Publisher: GenBank—Online Retrieved from the NIH NCBI database using the internet.
Haki, et al., "Developments in industrially important thermostable enzymes: a review", 2003, pp. 17-34 (Abstract Only), vol. 89(1), Publisher: Bioresour Technol, Published in: US.
Ratanachomsri, et al., "Thermostable xylanase from Marasmius sp.: purification and characterization", 2006, pp. 105-110 (Abstract Only), vol. 39(10, Publisher: J Biochem Mol Biol, Published in: US.
Ruller, et al., "Thermostable variants of the recombinant xylanase A from *Bacillus subtilis* produced by directed evolution show . . . ", 2008, pp. 1280-1293 (Abstract Only), vol. 70(4), Publisher: Proteins, Published in: US.
Sapre, et al., "Purification and characterization of a thermostable-cellulase free xylanase from Synephalastrum racemosum Cohn", 2005, pp. 327-334 (Abstract Only), vol. 51(6), Publisher: J Gen Appl Microbiol, Published in: US.
Simpson, et al., "An extremely thermostable xylanase from the termophilic eubacterium Thermotoga", 1991, pp. 413-417 (Abstract Only), vol. 277 (Pt 2), Publisher: Biochem J, Published in: US.
Stephens, et al., "Directed evolution of the termostable xylanase from *Thermomyces lanuginosus*", 2007, pp. 348-354 (Abstract Only), vol. 127(3), Publisher: J Biotechnol, Published in: US.
Tatu, et al., "Role of a disulfide cross-link in the conformational stability of a thermostable xylanase", 1990, pp. 641-646 (Abstract Only), vol. 9(5), Publisher: J Protein Chem, Published in: US.
Techapun, et al., "Thermostable and alkaline-tolerant cellulase-free xylanase produced by thermotolerant *Streptomyces* sp. Ab106", 2002, pp. 431-434 (Abstract Only), vol. 93(4), Publisher: J Biosci Bioeng, Published in: US.
Viikari, et al., "Thermostable enzymes in lignocellulose hydrolysis", 2007, pp. 121-145 (Abstract Only), vol. 108, Publisher: Adv Biochem Eng Biotechnol, Published in: US.
Weng, et al., "Construction, expression, and charcterization of a thermostable xylanase", 2005, pp. 188-192 (Abstract Only), vol. 51(3), Publisher: Curr Microbiol, Published in: US.
Zhengqiang, et al., "Characterization of a thermostable family 10 endo-xylanase (XynB) from Thermotoga maritima that cleaves p-nitrophenyl . . . ", 2001, pp. 423-428 (Abstract Only), vol. 92(5), Publisher: J Biosci Bioeng, Published in: US.
Bauer, et al, "An Endoglucanase, EglA, from the Hyperthermophilic Archaeon *Pyrococcus furiosus*..", Jan. 1999, pp. 284-290, vol. 181, No. 1, Publisher: Journal of Bacteriology, Published in: US.
PCT International Search Report, Application No. PCT/US2009/050080, mailed Mar. 19, 2010.
PCT Written Opinion of the ISA, Application No. PCT/US2009/050080, mailed Mar. 19, 2010.

* cited by examiner

A.

```
ATGATCTATTTTGTTGAGAAATACCACACCTCAGAAGACAAATCCACAAGCAATACCTC
CTCAACCCCCCCTCAAACGACACTTAGCACAACAAAGGTTCTCAAAATTCGGTATCCTG
ACGACGGCGAATGGCCTGGCGCTCCCATAGACAAAGACGGCGACGGAAATCCTGAGTTC
TATATCGAAATCAACCTCTGGAACATACTCAACGCGACTGGATTCGCAGAGATGACCTA
TAACTTGACATCTGGCGTTCTCCATTACGTTCAACAACTCGATAATATCGTTCTCCGCG
ATCGCTCAAACTGGGTACATGGCTATCCTGAAATTTTTTACGGCAATAAACCCTGGAAC
GCGAATTATGCCACCGACGGCCCGATCCCTCTCCCCAGTAAAGTTTCCAATCTCACAGA
CTTTTACTTGACTATCTCCTACAAGCTTGAACCAAAGAACGGACTCCCTATAAATTTTG
CAATCGAATCTTGGCTTACTAGAGAAGCATGGCGCACTACTGGAATCAACTCCGATGAA
CAGGAAGTAATGATCTGGATTTACTATGACGGACTCCAACCAGCCGGTTCCAAGGTGAA
AGAAATCGTTGTACCTATAATCGTTAATGGCACCCCAGTTAATGCTACCTTCGAAGTGT
GGAAAGCTAATATCGGATGGGAATACGTTGCCTTTAGAATCAAGACACCAATTAAAGAA
GGAACCGTGACAATCCCCTACGGTGCATTCATTAGCGTAGCTGCTAACATTTCTTCCCT
CCCAAATTACACAGAACTTTACCTGGAAGACGTTGAGATAGGCACAGAGTTTGGAACAC
CTTCAACTACTAGCGCACATCTCGAATGGTGGATTACTAACATTACCCTCACCCCACTT
GATCGTCCCCTGATCTCC
```

B.

```
MIYFVEKYHTSEDKSTSNTSSTPPQTTLSTTKVLKIRYPDDGEWPGAPIDKDGDGNPEF
YIEINLWNILNATGFAEMTYNLTSGVLHYVQQLDNIVLRDRSNWVHGYPEIFYGNKPWN
ANYATDGPIPLPSKVSNLTDFYLTISYKLEPKNGLPINFAIESWLTREAWRTTGINSDE
QEVMIWIYYDGLQPAGSKVKEIVVPIIVNGTPVNATFEVWKANIGWEYVAFRIKTPIKE
GTVTIPYGAFISVAANISSLPNYTELYLEDVEIGTEFGTPSTTSAHLEWWITNITLTPL
DRPLIS
```

```
ATGAGGTGGGTAGTTCTTCTGATGGTGGCGTTTTCTGCTCTGCTCTTTTCCTCCGAGGT
GGTTCTCACGAGCGTTGGCGCAGCGGATATCTCCTTCAACGGATTTCCCGTCACCATGG
AGCTCAACTTCTGGAACATAAAGTCGTATGAGGGAGAAACGTGGCTCAAATTCGATGGA
GAAAAGGTTGAGTTCTACGCGGATTTGTACAACATCGTTCTTCAGAATCCAGACAGCTG
GGTGCATGGATATCCGGAGATCTACTACGGTTACAAGCCCTGGGCGAGTCACAACAGCG
GTGTTGAATTTCTTCCTGTGAAGGTGAAAGATCTTCCGGATTTCTACGTGACTCTTGAT
TACTCGATCTGGTACGAAAACAATCTGCCTATCAACCTTGCAATGGAAACATGGATCAC
GAAAAGCCCCGACCAGACTTCTGTTTCTTCGGGTGATGCGGAGATCATGGTTTGGTTTT
ACAACAACGTTCTGATGCCCGGCGGTCAGAAAGTGGATGAGTTCACCACAACAGTTGAG
ATAAACGGAGTGAAGCAGGAAGCAAAATGGGATGTTTACTTCGCACCGTGGAGCTGGGA
TTACCTTGCCTTCAGACTGACAACACCGATGAAAGAAGGAAAGGTGAAGTTCAACGTGA
AGGACTTCGTTCAGAAAGCCGCGGAAGTTGTCAAAAAGCACTCAACGAGAATAGACAAT
TTCGAAGAGCTGTATTTCTGCGTCTGGGAGATCGGGACGGAATTTGGAGATCCAAACAC
AACAACGGCAAAATTCGGCTGGACCTTCAAAGACTTCTTCGTCGAAGTTGTAAAATAA
```

B.

```
MRWVVLLMVAFSALLFSSEVVLTSVGAADISFNGFPVTMELNFWNIKSYEGETWLKFDG
EKVEFYADLYNIVLQNPDSWVHGYPEIYYGYKPWASHNSGVEFLPVKVKDLPDFYVTLD
YSIWYENNLPINLAMETWITKSPDQTSVSSGDAEIMVWFYNNVLMPGGQKVDEFTTTVE
INGVKQEAKWDVYFAPWSWDYLAFRLTTPMKEGKVKFNVKDFVQKAAEVVKKHSTRIDN
FEELYFCVWEIGTEFGDPNTTTAKFGWTFKDFFVEVVK
```

ATGGAGGGGAATACTATTCTTAAAATCGTACTAATTTGCACTATTTTAGCAGGCCTATT
CGGGCAAGTCGTGCCAGTATATGCAGAAAATACAACATATCAAACACCGACTGGAATTT
ACTACGAAGTGAGAGGAGATACGATATACATGATTAATGTCACCAGTGGAGAGGAAACT
CCCATTCATCTCTTTGGTGTAAACTGGTTTGGCTTTGAAACACCTAATCATGTAGTGCA
CGGACTTTGGAAGAGAAACTGGGAAGACATGCTTCTTCAGATCAAAAGCTTAGGCTTCA
ATGCAATAAGACTTCCTTTCTGTACTGAGTCTGTAAAACCAGGAACACAACCAATTGGA
ATAGATTACAGTAAAAATCCAGATCTTCGTGGACTAGATAGCCTACAGATTATGGAAAA
GATCATAAAGAAGGCCGGAGATCTTGGTATCTTTGTCTTACTCGACTATCATAGGATAG
GATGCACTCACATAGAACCCCTCTGGTACACGGAAGACTTCTCAGAGGAAGACTTTATT
AACACATGGATAGAGGTTGCCAAAAGGTTCGGTAAGTACTGGAACGTAATAGGGCTGA
TCTAAAGAATGAGCCTCATAGTGTTACCTCACCCCCAGCTGCTTATACAGATGGTACCG
GGGCTACATGGGGTATGGGAAACCCTGCAACCGATTGGAACTTGGCGGCTGAGAGGATA
GGAAAAGCGATTCTGAAGGTTGCCCCTCATTGGTTGATATTCGTGGAGGGGACACAATT
TACTAATCCGAAGACTGACAGTAGTTACAAATGGGGCTACAACGCTTGGTGGGGAGGAA
ATCTAATGGCCGTAAAGGATTATCCAGTTAACTTACCTAGGAATAAGCTAGTATACAGC
CCTCACGTATATGGGCCAGATGTCTATAATCAACCGTACTTTGGTCCCGCTAAGGGTTT
TCCGGATAATCTTCCAGATATCTGGTATCACCACTTTGGATACGTAAAATTAGAACTAG
GATATTCAGTTGTAATAGGAGAGTTTGGAGGAAAATATGGGCATGGAGGCGATCCAAGG
GATGTTATATGGCAAAATAAGCTAGTTGATTGGATGATAGAGAATAAATTTTGTGATTT
CTTTTACTGGAGCTGGAATCCAGATAGTGGAGATACCGGAGGGATTCTACAGGATGATT
GGACAACAATATGGGAAGATAAGTATAATAACCTGAAGAGATTGATGGATAGTTGTTCC
AAAAGTTCTTCAAGTACTCAATCCGTTATTCGGAGTACCACCCCTACAAAGTCAAATAC
AAGTAAGAAGATTTGTGGACCAGCAATTCTTATCATCCTAGCAGTATTCTCTCTTCTCT
TAAGAAGGGCTCCCAGGTAG

B.

MEGNTILKIVLICTILAGLFGQVVPVYAENTTYQTPTGIYYEVRGDTIYMINVTSGEET
PIHLFGVNWFGFETPNHVVHGLWKRNWEDMLLQIKSLGFNAIRLPFCTESVKPGTQPIG
IDYSKNPDLRGLDSLQIMEKIIKKAGDLGIFVLLDYHRIGCTHIEPLWYTEDFSEEDFI
NTWIEVAKRFGKYWNVIGADLKNEPHSVTSPPAAYTDGTGATWGMGNPATDWNLAAERI
GKAILKVAPHWLIFVEGTQFTNPKTDSSYKWGYNAWWGGNLMAVKDYPVNLPRNKLVYS
PHVYGPDVYNQPYFGPAKGFPDNLPDIWYHHFGYVKLELGYSVVIGEFGGKYGHGGDPR
DVIWQNKLVDWMIENKFCDFFYWSWNPDSGDTGGILQDDWTTIWEDKYNNLKRLMDSCS
KSSSSTQSVIRSTTPTKSNTSKKICGPAILIILAVFSLLLRRAPR

```
ATGGAAATCAAGCTCTTCTGCGTGTTTATCGTGTTCATCATCCTCTTCTCCCCTTTCGT
GATTGCACTCTCGTATCCAGATGTTAACTATACTGCCGAGAATGGTATTATCTTCGTGC
AGAACGTCACTACGGGTGAGAAGAAGCCACTTTATCTTCACGGAGTGTCATGGTTTGGA
TTCGAGCTGAAGGACCACGTCGTCTATGGCTTGGATAAACGGAACTGGAAAGATATACT
CAAGGATGTTAAGCGCTTGGGTTTTAATGCTATCAGGCTTCCCTTCTGCTCTGAAAGCA
TCCGCCCTGATACGCGCCCTTCGCCTGAGCGGATAAACTACGAGTTGAACCCCGACTTG
AAGAATCTGACTTCCCTCGAAATAATGGAGAAGATTATTGAATACGCCAACTCAATCGG
GCTCTACATACTCTTGGATTATCACCGCATCGGTTGTGAGGAGATCGAACCTCTTTGGT
ATACCGAGAATTACTCAGAGGAGCAGTATATAAAGGATTGGATCTTCCTCGCAAAGCGG
TTCGGGAAGTACCCTAACGTGATAGGAGCTGATATCAAGAACGAGCCGCATGGTGAAGC
CGGGTGGGGTACGGGAGATGAGCGGGATTTCCGCCTCTTTGCCGAGAAGGTCGGGCGCG
AGATACTCAAGGTGGCCCCACACTGGTTGATATTCGTCGAGGGAACGCAATATACCCAT
GTCCCGAATATTGATGAGATCATCGAGAAGAAGGGCTGGTGGACATTTTGGGGAGAGAA
TCTTATGGGAGTTAAGGACTATCCAGTCAGGCTTCCGCGCGGCAAGGTCGTGTACTCAC
CGCATGTCTATGGACCATCTGTCTACATGATGGACTACTTCAAGTCGCCAGACTTTCCG
AACAATATGCCGATAATCTGGGAAACACACTTCGGATACTTGACCGACCTGAATTATAC
CTTGGTCATAGGCGAGTGGGGTGGCAACTATGAGGGCCTTGACAAGGTGTGGCAAGACG
CTTTCGTGAAGTGGCTGATTAAGAAGAAGATCTATAACTTCTTCTACTGGTGCCTGAAC
CCGGAGTCGGGTGACACCGGTGGCATCTTTCTCGACGACTGGAAAACCGTTAACTGGGA
AAAGATGAGGGTTATTTACAGGCTCATCAAGGCGGCGAACCCCGAGTTTGAGGAACCCC
TTTACATCATTTTGAAAACTAACGCGACGACATCTATCCTGGGCGTGGGTGAGAGGATC
CGGATTTACTGGTACACAAATGGCAAAGTTATTGACTCTAACTTCGCGCATTCCAGCGA
AGGCGAAATGAACATTACAGTGACGAAGTCCATGACTCTGTACATCATCGTGAAGAAGG
GCAATCAGACACTGAGGAAGGAACTCAAACTGTACGTTATCGGCGGCAATTACGGCTCC
AATATCTCCACTACCCAGCTGGTTACTCCCAAGAAAGGCGGCGAAAGGATTAGCACCAG
CCTGAAGCTGGCAATTAGCCTGCTCTTCATTCTCCTCTTCGTTTGGTATCTCCTCCGGG
AGAAGCAT
```

B.

```
MEIKLFCVFIVFIILFSPFVIALSYPDVNYTAENGIIFVQNVTTGEKKPLYLHGVSWFG
FELKDHVVYGLDKRNWKDILKDVKRLGFNAIRLPFCSESIRPDTRPSPERINYELNPDL
KNLTSLEIMEKIIEYANSIGLYILLDYHRIGCEEIEPLWYTENYSEEQYIKDWIFLAKR
FGKYPNVIGADIKNEPHGEAGWGTGDERDFRLFAEKVGREILKVAPHWLIFVEGTQYTH
VPNIDEIIEKKGWWTFWGENLMGVKDYPVRLPRGKVVYSPHVYGPSVYMMDYFKSPDFP
NNMPIIWETHFGYLTDLNYTLVIGEWGGNYEGLDKVWQDAFVKWLIKKKIYNFFYWCLN
PESGDTGGIFLDDWKTVNWEKMRVIYRLIKAANPEFEEPLYIILKTNATTSILGVGERI
RIYWYTNGKVIDSNFAHSSEGEMNITVTKSMTLYIIVKKGNQTLRKELKLYVIGGNYGS
NISTTQLVTPKKGGERISTSLKLAISLLFILLFVWYLLREKH
```

ATGGAAACGCTCCTCCCTGTAGTCGTGGTCCACGATATTGAGCCAGTTTCAATGCGTCT
TCAGAGGTACAAGAACAAAAATTCGATAAAAAGAGAAAAGCAGGGATTAATACCCCTGT
TTTTTTATTTTTGGGTGTATTTAGTTCTATTTGCGAATTTTCAGATTTTGAATGTAAAC
ATTTTCATAATAAGATGTTTTCTGGAGGTGATAATGGTGGTACTGATGACAAAACCGGG
AACATCGGATTTTGTATGGAATGGCATTCCCCTTTCCATGGAGCTGAATCTGTGGAACA
TAAAGGAATACTCCGGTTCTGTAGCTATGAAATTCGACGGTGAAAAGGTAACTTTCGAC
GCGGACATTCAGAATCTTTCTCCAAAAGAACCAGAAAGGTACGTTCTCGGTTATCCCGA
GTTCTATTACGGTTATAAACCCTGGGAAAAGCACACGGCAGAAGGTTCGAAACTTCCAG
TACCTGTTTCCTCTATGAAATCATTTTCCGTCGAAGTTTCTTTCGATATTCACCACGAA
CCGTCTCTGCCTTTGAACTTTGCCATGGAAACATGGCTCACAAGAGAAAAGTACCAGAC
GGAAGCGTCGATCGGCGATGTTGAAATCATGGTCTGGTTCTATTTCAACAATCTCACAC
CAGGGGGCAAAAAGATAGAGGAGTTTACGATTCCGTTCGTGCTGAACGGAGAGAGTGTC
GAAGGCACCTGGGAACTGTGGCACGCGGAGTGGGGATGGGACTACCTCGCTTTCCGCTT
GAAGGATCCCGTGAAGAAGGGAAGGGTGAAGTTCGACGTGAGGCATTTTCTTGATGCCG
CCGGGAAAGCTCTTTCGAATTCCACTCGTGTGAAAGATTTTGAAAATCTTTACTTCACC
GTCTGGGAAATTGGAACCGAGTTTGGAAGCCCGGAAACAAAGAGCGCGCAATTCGGGTG
GAAGTTTGAAAACTTCTCTATTGATCTGGAGGTGAGAGAATGA

B.

METLLPVVVHDIEPVSMRLQRYKNKNSIKREKQGLIPLFFYFWVYLVLFANFQILNVN
IFIIRCFLEVIMVVLMTKPGTSDFVWNGIPLSMELNLWNIKEYSGSVAMKFDGEKVTFD
ADIQNLSPKEPERYVLGYPEFYYGYKPWEKHTAEGSKLPVPVSSMKSFSVEVSFDIHHE
PSLPLNFAMETWLTREKYQTEASIGDVEIMVWFYFNNLTPGGKKIEEFTIPFVLNGESV
EGTWELWHAEWGWDYLAFRLKDPVKKGRVKFDVRHFLDAAGKALSNSTRVKDFENLYFT
VWEIGTEFGSPETKSAQFGWKFENFSIDLEVRE

ATGTTGAAACTTATTCCACTTGTTAATGGCAATTATAAGTTGATTCAATGGGAGCCACT
CGGCGGCGTGCACGGAGCAGATATCGAGTGCATACATGTTACCCCAAACGTATGGAACA
TAGATAAATCATCAGTTGGCACTGTACAGATCGAATATGAGCCCCAAGTTGGCTGTCTT
CGTTTTTCAATTGATTTCCCGAGGATAAGTATAAGACATAATGTAGGCGTAGCGGCATA
TTCAGAAGTTATTTACGGACACAAGCCGTGGGGCCCCACCACTTGCATGGACCCTCAGT
TCAAGTTCCCTATCAAAGTCAATGAGTCAAAAGGACTGTACTCGTATGTAAATTATAAC
GTTAAATCTAGGTCACCAGATGACTCAATCTTTAATATTGCTTACGATCTCTGGCTTAC
AACGTCCCCAAACCTTACAAACGGACCCCAGCCAGGAGACGTAGAAGTTATGATCTGGT
TGTACTACCACGGACAGCGCCCTGCAGGCAGACTCATCGGGGAACTCCGCATGCCGATT
ACATTGGGCGATAGTGAGGCGGCACGTGACTTTGAAGTATGGGTGGCTGACACAGGAAT
AGGAATCGGTGAATGGGCGGTAGTGACCTTCAGAATCAAGGACCCAATAAAGGGCGGTT
TGATAGGAGTTAACCTCATAAACTACATCGAAAGTGCTTTTAAAACGCTCGAAGAACTC
AACCCGGTCAAGTGGCGGTACGGCGACCTGCTCAACAAATATCTTAATGGAATTGAATT
CGGCAGTGAGTTTGGTAATGTCTCCTCAGGAATGATAAAACTTAATTGGGAACTCTGCG
GCCTGAGCCTTGTGAAAGACTCTTCT

B.

MLKLIPLVNGNYKLIQWEPLGGVHGADIECIHVTPNVWNIDKSSVGTVQIEYEPQVGCL
RFSIDFPRISIRHNVGVAAYSEVIYGHKPWGPTTCMDPQFKFPIKVNESKGLYSYVNYN
VKSRSPDDSIFNIAYDLWLTTSPNLTNGPQPGDVEVMIWLYYHGQRPAGRLIGELRMPI
TLGDSEAARDFEVWVADTGIGIGEWAVVTFRIKDPIKGGLIGVNLINYIESAFKTLEEL
NPVKWRYGDLLNKYLNGIEFGSEFGNVSSGMIKLNWELCGLSLVKDSS

```
ATGATGGGAAAGATCGATGAAATCCTTTCACAGCTGACTATTGAAGAAAAGTGAAACT
TGTAGTGGGGGTTGGTCTTCCAGGACTTTTTGGAAATCCACATTCCAGAGTGGCAGGTG
CAGCTGGAGAAACGCATCCTGTTCCGAGGCTTGGAATTCCTTCTTTCGTTCTGGCCGAC
GGTCCCGCGGGCCTCAGAATAAATCCCACAAGAGAGAACGACGAAAACACCTATTACAC
AACAGCGTTTCCTGTTGAAATCATGCTCGCTTCCACCTGGAACAAAGATCTTCTGGAAG
AAGTAGGAAAAGCTATGGGAGAAGAAGTCAGGGAATACGGTGTCGATGTGCTTCTTGCA
CCTGCGATGAACATTCACAGGAACCCTCTTTGTGGAAGGAATTTCGAGTATTATTCAGA
AGATCCTGTCCTTTCCGGTGAAATGGCTTCAGCCTTTGTCAAGGGAGTTCAATCTCAAG
GGGTGGGAGCCTGCATAAAACACTTTGTCGCGAACAACCAGGAAACGAACAGGATGGTA
GTGGACACGATCGTGTCCGAGCGAGCCCTCAGAGAAATATATCTGAAAGGTTTTGAAAT
TGCCGTCAAGAAAGCAAGACCCTGGACCGTGATGAGCGCTTACAACAAACTGAATGGAA
AATACTGTTCACAGAACGAATGGCTTTTGAAGAAGGTTCTCAGGGAAGAATGGGGATTT
GACGGTTTCGTGATGAGCGACTGGTACGCGGGAGACAACCCTGTAGAACAGCTCAAGGC
CGGAAACGATATGATCATGCCTGGAAAAGCGTATCAGGTGAACACGGAAAGAAGAGATG
AAATAGAAGAAATCATGGAGGCGTTGAAGGAGGGAAGACTCAGTGAGGAAGTCCTGAAC
GAATGTGTGAGAAACATCCTCAAAGTTCTTGTGAACGCGCCTTCCTTTAAAGGGTACAG
GTACTCGAACAAACCGGACCTCGAATCTCACGCGAAAGTTGCCTACGAAGCAGGTGTGG
AGGGTGTTGTCCTTCTTGAGAACAACGGTGTTCTTCCATTCGATGAAAGTATCCATGTC
GCCGTCTTTGGCACCGGTCAAATCGAAACAATAAAGGGAGGAACGGGAAGTGGAGACAC
CCATCCGAGATACACGATCTCTATCCTTGAAGGCATAAAAGAAAGAAACATGAAGTTCG
ACGAAGAACTCACCTCCATCTATGAGGATTACATCAAAAAGATGAGAGAAACAGAGGAA
TATAAACCCAGAACTGACTCCTGGGGAACGGTTATAAAACCGAAACTTCCAGAGAACTT
TCTCTCAGAAAAAGAGATAAAGAAGGCTGCGAAGAAAAACGATGCTGCAGTTGTTGTAA
TCAGTAGGATCTCCGGTGAGGGATACGACAGAAAGCCGGTGAAGGTGACTTCACCTCT
CCGATGACGAGCTGGAGCTCATAAAAACAGTCTCAAGGGAATTCCACGAACAGGGTAAG
AAGGTTGTGGTTCTTCTCAACATCGGAAGTCCCATTGAAGTTGCAAGCTGGAGAGATCT
TGTGGATGGAATCCTTCTCGTCTGGCAAGCAGGACAGGAGATGGGAAGAATAGTGGCCG
ATGTTCTTGTGGGAAGGGTAAACCCCTCCGGAAAACTTCCAACGACCTTCCCGAAGGAT
TACTCGGACGTTCCATCCTGGACGTTCCCAGGAGAGCCAAAGGACAATCCGCAAAGAGT
GGTGTACGAGGAAGACATCTACGTGGGATACAGGTACTACGACACCTTTGGTGTGGAAC
CTGCCTACGAGTTCGGCTACGGCCTCTCTTACACAAAGTTTGAATACAAAGATTTAAAG
ATCGCTATCGACGGAGATATACTCAGAGTGTCGTACACGATCACAAACACCGGGGACAG
AGCTGGAAAGGAAGTCTCACAGGTTTATGTCAAAGCTCCAAAAGGGAAAATAGACAAAC
CCTTCCAGGAGCTGAAAGCGTTCCACAAAACAAAACTTTTGAACCCGGGTGAATCCGAA
AAGATCTTTCTGGAAATTCCTCTTAGAGATCTTGCGAGTTTCGATGGGAAAGAATGG
TTGTCGAGTCAGGAGAATACGAGGTCAGGGTCGGTGCATCTTCGAGGGATATAGGTTGA
GAGATATTTTTCTGGTTGAGGGAGAGAAGAGATTCAAACCATGA
```

MMGKIDEILSQLTIEEKVKLVVGVGLPGLFGNPHSRVAGAAGETHPVPRLGIPSFVLAD
GPAGLRINPTRENDENTYYTTAFPVEIMLASTWNKDLLEEVGKAMGEEVREYGVDVLLA
PAMNIHRNPLCGRNFEYYSEDPVLSGEMASAFVKGVQSQGVGACIKHFVANNQETNRMV
VDTIVSERALREIYLKGFEIAVKKARPWTVMSAYNKLNGKYCSQNEWLLKKVLREEWGF
DGFVMSDWYAGDNPVEQLKAGNDMIMPGKAYQVNTERRDEIEEIMEALKEGRLSEEVLN
ECVRNILKVLVNAPSFKGYRYSNKPDLESHAKVAYEAGVEGVVLLENNGVLPFDESIHV
AVFGTGQIETIKGGTGSGDTHPRYTISILEGIKERNMKFDEELTSIYEDYIKKMRETEE
YKPRTDSWGTVIKPKLPENFLSEKEIKKAAKKNDAAVVVISRISGEGYDRKPVKGDFYL
SDDELELIKTVSREFHEQGKKVVVLLNIGSPIEVASWRDLVDGILLVWQAGQEMGRIVA
DVLVGRVNPSGKLPTTFPKDYSDVPSWTFPGEPKDNPQRVVYEEDIYVGYRYYDTFGVE
PAYEFGYGLSYTKFEYKDLKIAIDGDILRVSYTITNTGDRAGKEVSQVYVKAPKGKIDK
PFQELKAFHKTKLLNPGESEKIFLEIPLRDLASFDGKEWVVESGEYEVRVGASSRDIRL
RDIFLVEGEKRFKP

```
ATGAACGTGAAAAAGTTCCCTGAAGGATTCCTCTGGGGTGTTGCAACAGCTTCCTACCA
GATCGAGGGTTCTCCCCTCGCAGACGGAGCTGGTATGTCTATCTGGCACACCTTCTCCC
ATACTCCTGGAAATGTAAAGAACGGTGACACGGGAGATGTGGCCTGCGACCACTACAAC
AGATGGAAAGAGGACATTGAAATCATAGAGAAACTCGGAGTAAAGGCTTACAGATTTTC
AATCAGCTGGCCAAGAATACTTCCGGAAGGAACAGGAAGGGTGAATCAGAAAGGACTGG
ATTTTTACAACAGGATCATAGACACCCTGCTGGAAAAAGGTATCACACCCTTTGTGACC
ATCTATCACTGGGATCTTCCCTTCGCTCTTCAGTTGAAAGGAGGATGGGCGAACAGAGA
AATAGCGGATTGGTTCGCAGAATACTCAAGGGTTCTCTTTGAAAATTTCGGCGACCGTG
TGAAGAACTGGATCACCTTGAACGAACCGTGGGTTGTTGCCATAGTGGGGCATCTGTAC
GGAGTCCACGCTCCTGGAATGAGAGATATTTACGTGGCTTTCCGAGCTGTTCACAATCT
CTTGAGGGCACACGCCAAAGCGGTGAAAGTGTTCAGGGAAACTGTGAAAGATGGAAAGA
TCGGAATAGTTTTCAACAATGGATATTTCGAACCTGCGAGTGAAAAGAGGAGGACATC
AGAGCGGCGAGATTCATGCATCAGTTCAACAACTATCCTCTCTTTCTCAATCCGATCTA
CAGAGGAGATTATCCGGAGCTCGTTCTGGAATTTGCCAGAGAGTATCTACCGGAGAATT
ACAAAGATGACATGTCCGAGATACAGGAAAAGATCGACTTTGTTGGATTGAACTATTAC
TCCGGTCATTTGGTGAAGTTCGATCCAGATGCACCAGCTAAGGTCTCTTTCGTTGAAAG
GGATCTTCCAAAAACAGCCATGGGATGGGAGATCGTTCCAGAAGGAATCTACTGGATCC
TGAAGAAGGTGAAAGAAGAATACAACCCACCAGAGGTTTACATCACAGAGAATGGGCT
GCTTTTGACGACGTAGTTAGTGAAGATGGAAGAGTTCACGATCAAAACAGAATCGATTA
TTTGAAGGCCCACATTGGTCAGGCATGGAAGGCCATACAGGAGGGAGTGCCGCTTAAAG
GTTACTTCGTCTGGTCGCTCCTCGACAATTTCGAATGGGCAGAGGGATATTCCAAGAGA
TTTGGTATTGTGTACGTGGACTACAGTACTCAAAAACGCATCATAAAAGACAGTGGTTA
CTGGTACTCGAACGTGGTCAAAAGCAACAGTCTGGAAGATTGA
```

B.

```
MNVKKFPEGFLWGVATASYQIEGSPLADGAGMSIWHTFSHTPGNVKNGDTGDVACDHYN
RWKEDIEIIEKLGVKAYRFSISWPRILPEGTGRVNQKGLDFYNRIIDTLLEKGITPFVT
IYHWDLPFALQLKGGWANREIADWFAEYSRVLFENFGDRVKNWITLNEPWVVAIVGHLY
GVHAPGMRDIYVAFRAVHNLLRAHAKAVKVFRETVKDGKIGIVFNNGYFEPASEKEEDI
RAARFMHQFNNYPLFLNPIYRGDYPELVLEFAREYLPENYKDDMSEIQEKIDFVGLNYY
SGHLVKFDPDAPAKVSFVERDLPKTAMGWEIVPEGIYWILKKVKEEYNPPEVYITENGA
AFDDVVSEDGRVHDQNRIDYLKAHIGQAWKAIQEGVPLKGYFVWSLLDNFEWAEGYSKR
FGIVYVDYSTQKRIIKDSGYWYSNVVKSNSLED
```

Figure 8A-B

High-temperature operating and thermo-stable cellulases

| PROTEIN | Source | | Physical Properties | | | | | Mode of Operation | Functional Properties | | | |
|---|---|---|---|---|---|---|---|---|---|---|---|---|
| | Locus | Codon Usage | CaZy | MW d | pI | Charge pH7 | T° °C | pH range | | Specific Activity | | | |
| | | | | | | | | | | swAvicel | avCellulose | Paper | pNPG |
| Tcel1 | o-eglA | corn optimized | GH12 | 34,005 | 4.80 | -13.10 | 102 | 7 - 8 | exocellulase | 63.4 | 13.6 | 10.5 | - |
| Tcel2 | petroB | bacteria | GH12 | 31,816 | 4.77 | -13.30 | 98 | 6 - 7 | exocellulase | 8.1 | 2.2 | 2.9 | - |
| Tcel3 | ph1171 | archea | GH5 | 51,930 | 6.47 | -3.60 | 94 | 6 | exocellulase | 48.5 | 8.4 | 8.6 | - |
| Tcel4 | o-E1 | rice optimized | GH5 | 59,980 | 7.05 | 0.30 | 95 | 5 - 6 | endocellulase | 6.8 | 2.2 | 4.1 | - |
| Tcel5 | petroA | bacteria | GH12 | 38,226 | 5.58 | -6.60 | 96 | 5 - 6 | endocellulase | 34.1 | 6.8 | 8.0 | - |
| Tcel6 | zp#4 | corn optimized | GH12 | 31,818 | 5.66 | -5.00 | 85 | 5 - 6 | endocellulase | 20.6 | 5.1 | 5.1 | - |
| Tcel7 | Tpet0898 | bacteria | GH3 | 81,243 | 5.38 | -16.90 | 98 | 5 | beta-glucosidase | 0.8 | 0.8 | - | 69.4 |
| Tcel8 | Tpet0952 | bacteria | GH1 | 51,509 | 5.84 | -9.10 | 92 | 6 - 7 | beta-glucosidase | 1.7 | 1.5 | - | 60.9 |
| Tcel9 | g12#3 | corn optimized | GH12 | 45,059 | 6.16 | -2.20 | 85 | 5 - 6 | endocellulase | 5.2 | 1.4 | 7.5 | - |
| Tcel10 | ph0746 | archea | GH65 | 85,598 | 7.80 | 4.30 | 94 | 6 | endocellulase | 4.9 | 1.5 | 3.9 | - | swAVICEL Phosphoric acid swollen Avicel, avCellulose, Avicel (Sigmacell): Cellulase specific activity, mM reducing sugar/mg protein/day at 85 °C, pH 6
Beta-glucosidase specific acitvity, nM pN/ug protein/min

Figure 9

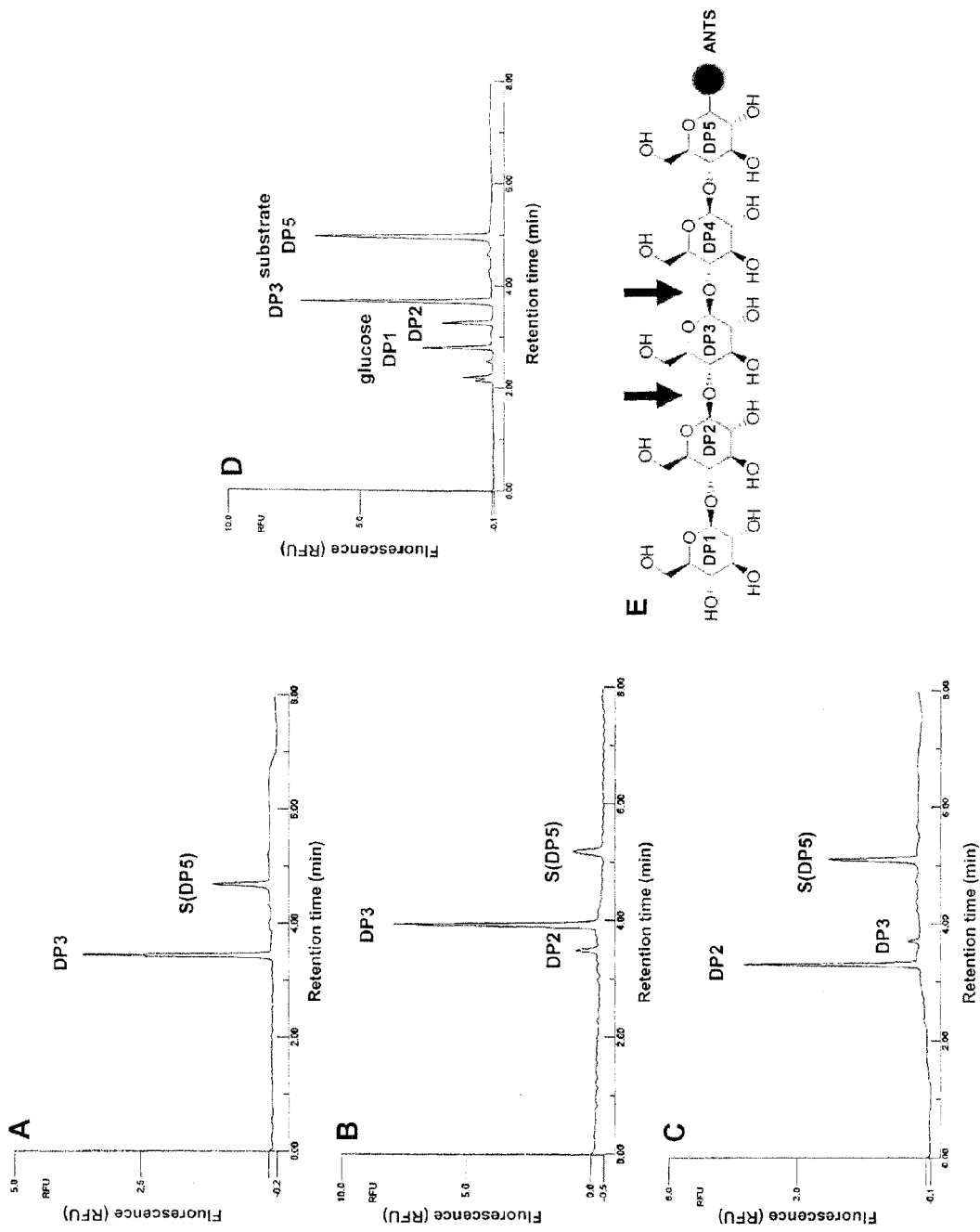
Figure 10A-E

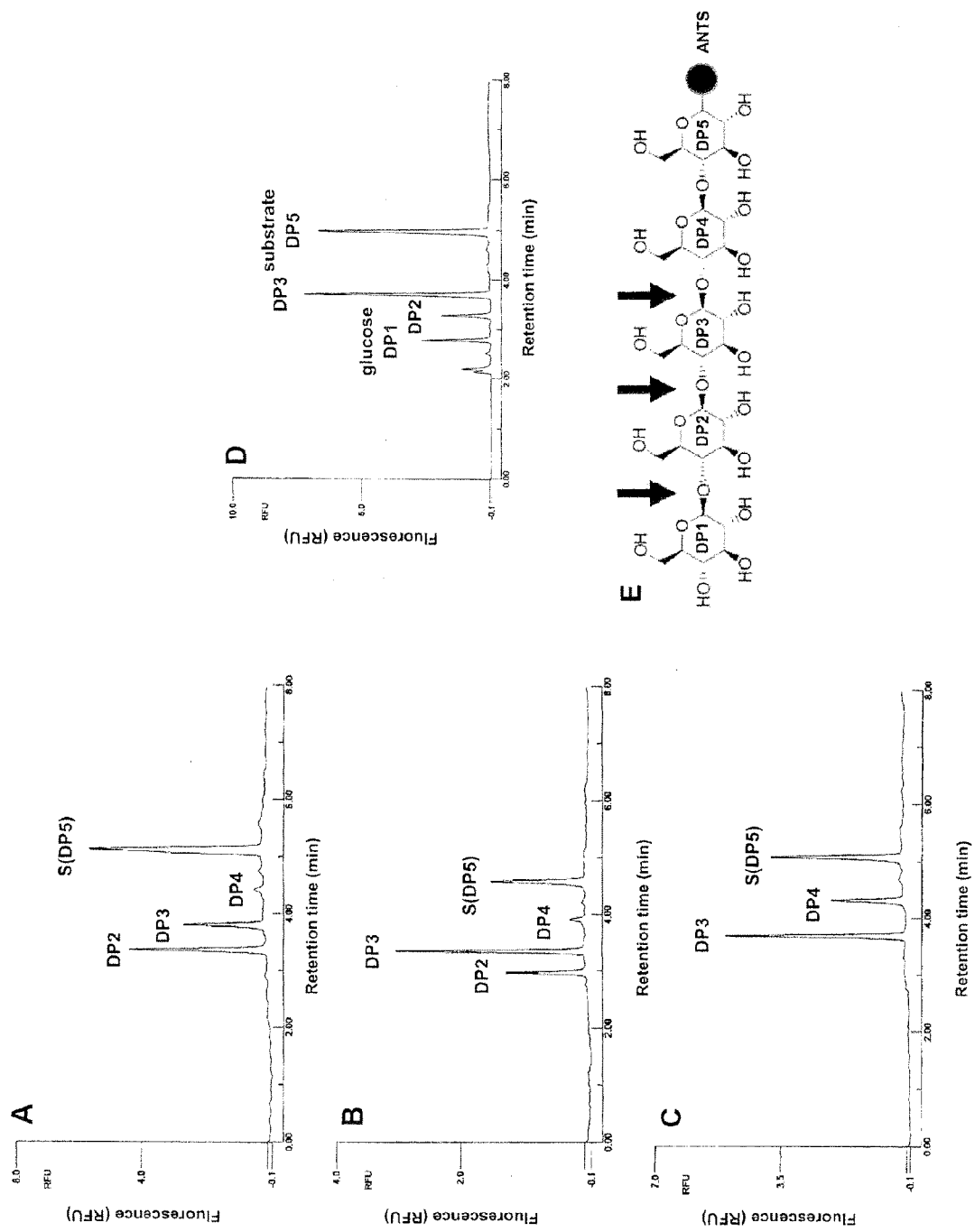
Figure 11A-E

High-temperature catalytic operating cellulases

| PROTEIN | U | T opt °C | % Specific activity at 60 °C | 45 °C | 20 °C |
|---|---|---|---|---|---|
| AVICEL$_{sw}$ | | | | | |
| Tcel1 | 63.4 | 102 | 56.0 | 40.0 | 20.0 |
| Tcel2 | 8.1 | 98.0 | 42.2 | 25.3 | 14.1 |
| Tcel3 | 48.5 | 94.0 | 44.7 | 21.1 | 10.5 |
| Tcel4 | 6.8 | 95.0 | 26.0 | 11.6 | 4.3 |
| Tcel5 | 34.1 | 96.0 | 53.6 | 34.1 | 14.6 |
| Tcel6 | 20.6 | 85.0 | 71.4 | 46.4 | 14.3 |
| pNPG | | | | | |
| Tcel7 | 69.4 | 98.0 | 4.4 | 1.1 | 1.0 |
| Tcel8 | 60.9 | 92.0 | 25.0 | 12.5 | 2.5 |

$_{sw}$AVICEL Phosphoric acid swollen Avicel, $_{av}$Cellulose, Avicel (Sigmacell): Cellulase specific activity, μM reducing sugar/mg protein/day at 85 °C, pH 6, Beta-glucosidase specific activity, nM pN/ug protein/min

Figure 12

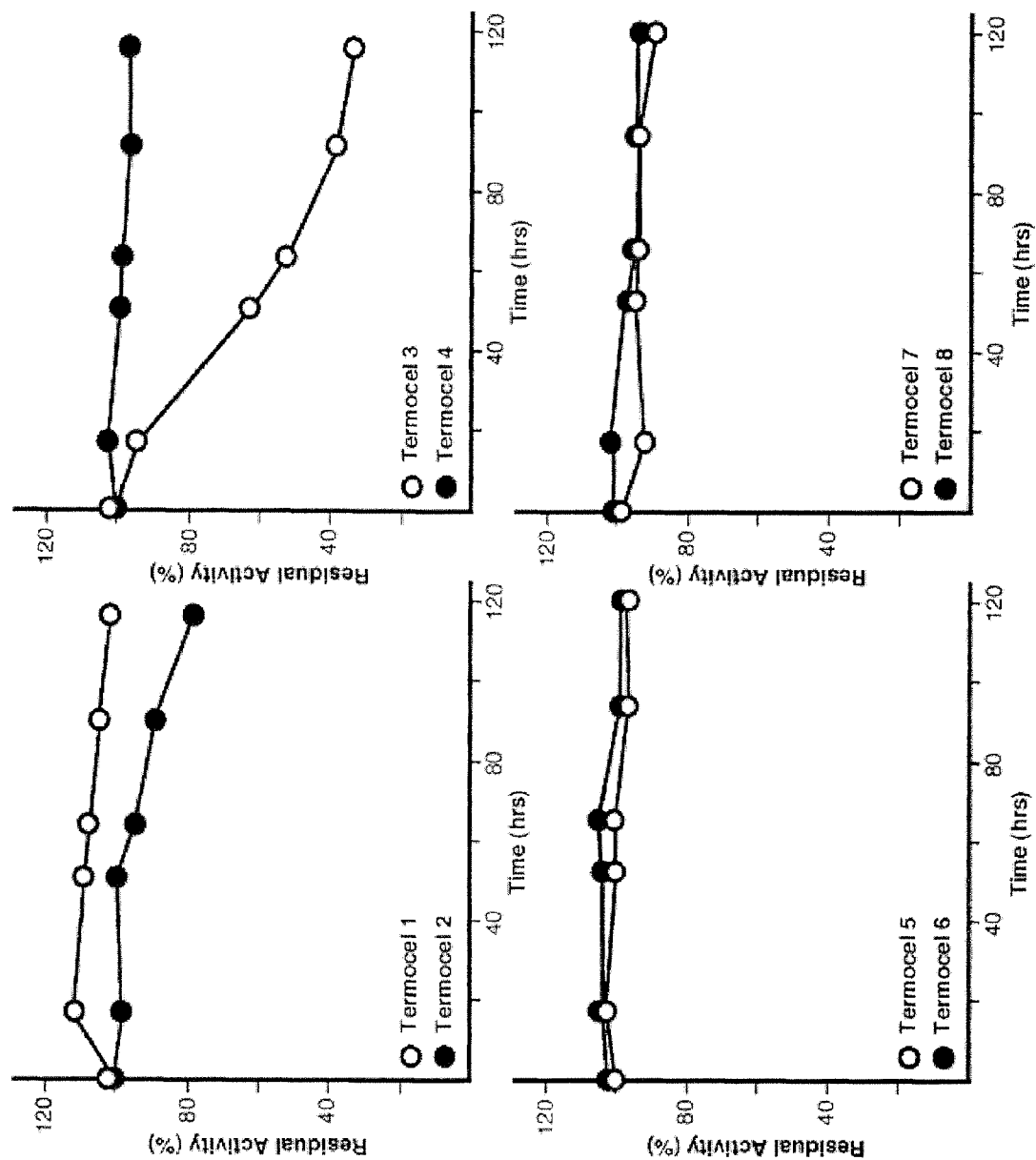
Figure 13A-D

Biomass substrate specificity of Termocels

| Substrate | Specific activity (reducing-end µmole/mg protein/h) | | | | | | | |
|---|---|---|---|---|---|---|---|---|
| | Tcel1 | Tcel2 | Tcel3 | Tcel4 | Tcel5 | Tcel6 | Tcel7 | Tcel8 |
| avicel | 1.62 | - | - | - | 5.35 | - | 0.75 | 1.73 |
| swollen avicel | 29.82 | 57.48 | 11.28 | 21.73 | 36.67 | 29.77 | 0.79 | 1.57 |
| carboxymetnyl cellulose | 69.01 | 234.77 | 68.66 | 53.75 | 131.22 | 167.28 | 0.79 | 1.35 |
| alpha-cellulose | 6.12 | 21.42 | 1.16 | 12.52 | 7.34 | 5.06 | 0.71 | 0.74 |
| barley beta-glucan | 67.51 | 158.26 | 45.07 | 32.26 | 160.36 | 117.91 | 2.99 | 31.34 |
| laminarin | 4.22 | 21.55 | 3.94 | 17.45 | 6.47 | 10.65 | 21.08 | 28.68 |
| lichenan | 110.12 | 269.03 | 82.17 | 51.29 | 238.06 | 192.05 | 8.34 | 44.51 |
| starch | 0.45 | 18.77 | 3.34 | 13.94 | 4.26 | 6.23 | 0.48 | 1.53 |
| birch wood xylan | 31.26 | 18.73 | 4.68 | 19.18 | nd | nd | 0.30 | 1.23 |
| beechwood xylan | 27.55 | 18.98 | 3.69 | 24.31 | 27.30 | 136.76 | 0.89 | 1.12 |
| oat-spelt xylan | 19.07 | 22.23 | 3.44 | 17.51 | 34.29 | 70.27 | 0.70 | 1.32 |
| Wheat arabinoxylan | 23.52 | 21.85 | 3.49 | 15.83 | 36.24 | 181.46 | 0.70 | 1.18 |

```
ATGGACTACTCTATCAACTGCTCTATCAACCCTATAACCCTCATGGTCGCGCACTCTTC
TCCCCTGAACCCATCTAACACACTCGAACTTACACTTATTCTCGAAAATGGCATCACCA
CCACAGTAACTGTCACCGCGACACCACGCAACACTTACCCTATGATCTCCCTTGGCTAC
ATTAATATTACCCCTAACCTCTGGAACCTTAACACAGCTTCGTCATCAGGATACGCCTC
TATGGTCTACGATGCATCACAGGGTGCTCTTTATATTCATGTTAATTTCACAAAGGTTT
ACCTCAATCAGCAAGTTGGTGTTGCCGCCTACTCTGAATTCATCTATGGCTACAAACCC
TGGGGCACGCTCACCTCCGAGGCAGGCGGGTTCAATTTTCCTGTTAAGCTTACCGAACT
CGGTTCTCTTCTTTCGTTCATCAATTACTCACTCATTTCATATTCTCCACAAGTCGCTA
TCTTCGATTGGGCATACGACCTTTGGCTCACAACATCCCCAAATCTCACCAACGGCCCT
CAACCCGGCGACGTCGAGGTCATGATCTGGCTCTATTATCACCTGCAACAACCTGCGGG
TTTTCCCGTCGCTAACGTTACAGTGCCAATATGGGTCAATGGCTCCCTCGTTAACGAAA
CATTTGAGGTTTGGATTGGTTCTCCACAGATCGAACCCGGCACCCACGCTATAGTCTCC
TTCAGGCCAACGAATCCAATCCCTAGAGGCCTCGTCGGCGTAAATGTCACGAAGTTCCT
TCAACTTGCCGTTAACTATCTCGTGACACTCTACCCCTCATACTGGAACTACACATATC
TGGAGAGCAAGTACTTGAATGGCATCGAATTCGGATCAGAATGGGGCAATCCGTCTACA
TACAATATTACACTCAATTGGGTCATTTATAAAGCTTATCTTATCAAGGTGCCTCTGGA
GTCACAGGGCACCGTTACCGTCACATATACTACAACTGTTACATCCACCATGACTGTTA
CCTCAATCCTTGCTACCACATCCACCGTCACCACTACATCTACACTTACATCTACCGTT
ACCGCCACTTCAGTTTCTACTTCCACCGTCACGCAGACTCTCACTACCTCCATCGTCAA
AACCGTCATCCCTGTCTACTATACTGCCACCATAATCGTCCTTCTTATAATCATCGCAG
TCGTCATTGCACTTGCGTTCGCCCGCCGCGGCATCCGGGTTCGTCTCTGT
```

B.

```
MDYSINCSINPITLMVAHSSPLNPSNTLELTLILENGITTTVTVTATPRNTYPMISLGY
INITPNLWNLNTASSSGYASMVYDASQGALYIHVNFTKVYLNQQVGVAAYSEFIYGYKP
WGTLTSEAGGFNFPVKLTELGSLLSFINYSLISYSPQVAIFDWAYDLWLTTSPNLTNGP
QPGDVEVMIWLYYHLQQPAGFPVANVTVPIWVNGSLVNETFEVWIGSPQIEPGTHAIVS
FRPTNPIPRGLVGVNVTKFLQLAVNYLVTLYPSYWNYTYLESKYLNGIEFGSEWGNPST
YNITLNWVIYKAYLIKVPLESQGTVTVTYTTTVTSTMTVTSILATTSTVTTTSTLTSTV
TATSVSTSTVTQTLTTSIVKTVIPVYYTATIIVLLIIAVVIALAFARRGIRVRLC
```

```
ATGAGATTTCAATTCGGATTCTCCAAAGAAGATGAACAGGTGCTGGGCACAATACTAAC
ACTCGGAAATGGACAATTAGGAGTTAGGGGAGAATTTGAACTCGAGAGATCTCCTTATG
GAACGATCGTTAGCGGGGTCTATGATTACACTCCCTACTTCTACAGGGAATTGGTAAAT
GGTCCCAGGACTATAGGGATGATAATAATTATAGATGGAGAACTAATAAATCCAAGCTC
TCAAAAGTCAAGGAATTCCAGAGAGAGCTCGATATAGAAAAGGCTTATTAAGAACTC
ACTTAGAGATTGAAACAAAAATGGAAATAAAATTTTATATAAAAGTACAAGGATAGTC
CACATGAAAAGAAAAACCTAATCCTTCTAGATTTTGAGCTAAAAGCTAGCAAGGGAGG
AATCGCAGTTGTAGTTAATCCCATAGAATTCAATACTGCAAATCCAGGGTTTATAGACG
AGATAATGATCAAGCATTATAGAGTGGACTCGATAAAAGAGACTGAGGAGGGAGTATAC
GCTAGGGTGAAAACTTTAGACAATAAGTACACGTTGGAAATTGCAAGTAGCTTGGTTCC
ATCAGAATATACATCGAGGAGCACCTTTAGAACCGATAATGAAATTGGAGAAATTTACA
TTGTTAAACTTAAACCAGGAAAAACGTACAAATTTACAAAGTACGTTACAGTATCTAAA
GGAGCAGCTTTAGAGGAGTTAAAAGATGTTAAGAGATTAGGATTTGAAAAGCTATATGA
AGAGCATATAAACAGCTGGAAGAGAATATGGGAGAAAGTGAAAGTGGAAATCGAAGGAG
ATAAAGACCTTGAAAATGCCCTAAACTTTAACATTTTTCACTTGATCCAATCCCTTCCA
CCAACAGATAAAGTCTCGCTACCAGCAAGGGGAATACATGGGTTTGGGTATAGGGACA
TATATTCTGGGATACAGAGATATATGCATTACCTTTCTTCATATTCACGATGCCAAAAG
AGGCCAGGAGATTGCTCCTCTATAGATGCAACAACTTAGATGCCGCTAAAGAAAATGCA
AAGATGAATGGATATCAAGGGGTCCAATTTCCCTGGGAGTCGGCAGATGATGGACGCGA
GGCTACCCCCTCTGAGATACCATTGGATATGTTGGGAAGGAAAATCGTTAGAATTTACA
CCGGAGAGGAGGAACATCACATAACTGCGGATATAGCATATATAGTTGATTTTTATTAC
CAAGTCTCTGGAGATCTCGAATTTATGAACAGGTGTGGCCTTGAGATAATCTTTGAGAC
GGCCCGATTTTGGGCTAGTAGGGTTGAGTTCGAGGAAGGAAAAGGGTACGTCATTAAAA
AAGTAATAGGACCTGATGAATACCATGAGCACGTTAACAACAACTTCTTTACAAACTTA
ATGGCCAAGCATAATCTCGAACTTGCAATAAGATACTTTAGAGAGTCAAAGAATAGGGA
ACCGTGGAAAAGATTGTCGAAAAATTAAACATAAGAGAGGAGGAGGTTGAAAAATGGG
AAGAGATAGCTAAAAACATGTACATTCCCAGGAAGATAGACGGAGTTTTTGAAGAGTTT
GATGGTTACTTTGAATTGATGGATTTTGAAGTTGATCCCTTCAATATTGGAGAAAAAAC
ACTCCCCGAGGAAATCAGGAATAACATAGGGAAAACGAAACTCGTTAAGCAGGCCGATG
TCATCATGGCCCAATATCTCCTTAAGGACTACTTCTCTCCAGAGGAAATAAAGAGTAAC
TTTAACTATTATATAAGGAGAACTACCCATGCTTCATCACTCTCCATGCCCCATACGC
GATCATTGCAACCTGGATAGGGGAGGTAAAGATAGCATATGAGTACTTCAAGAGATGTG
CAAATATAGATCTCAAAACGTGTACGGAAACACTGCAGAGGGATTTCACTTAGCAACG
GCGGGAGGAACCTGGCAAGTACTCGTCAGAGGATTTTGTGGCCTCAATGTAAAAGGAAA
CAAAATAGAGCTTAATCCTAATCTTCCTGAAAAATGGAAGTACGTTAAGTTCAGGATAT
TCTTCAAAGGTTCATGGATAGAATTTAAATTTCTAGGAAGAAAGTTAGGGCTAGAATG
CTTGAAGGATCGAGAAAAGTCAAAATATCTAGCTTTGGAAAGGAAGTAGATCTATATCC
TGGAAAAGAGGTTGTAATAGTAGCTAATTAA
```

```
MRFQFGFSKEDEQVLGTILTLGNGQLGVRGEFELERSPYGTIVSGVYDYTPYFYRELVN
GPRTIGMIIIIDGELINPSSQKVKEFQRELDIEKGLLRTHLEIETKNGNKILYKSTRIV
HMKRKNLILLDFELKASKGGIAVVVNPIEFNTANPGFIDEIMIKHYRVDSIKETEEGVY
ARVKTLDNKYTLEIASSLVPSEYTSRSTFRTDNEIGEIYIVKLKPGKTYKFTKYVTVSK
GAALEELKDVKRLGFEKLYEEHINSWKRIWEKVKVEIEGDKDLENALNFNIFHLIQSLP
PTDKVSLPARGIHGFGYRGHIFWDTEIYALPFFIFTMPKEARRLLLYRCNNLDAAKENA
KMNGYQGVQFPWESADDGREATPSEIPLDMLGRKIVRIYTGEEEHHITADIAYIVDFYY
QVSGDLEFMNRCGLEIIFETARFWASRVEFEEGKGYVIKKVIGPDEYHEHVNNNFFTNL
MAKHNLELAIRYFRESKNREPWKKIVEKLNIREEEVEKWEEIAKNMYIPRKIDGVFEEF
DGYFELMDFEVDPFNIGEKTLPEEIRNNIGKTKLVKQADVIMAQYLLKDYFSPEEIKSN
FNYYIRRTTHASSLSMPPYAIIATWIGEVKIAYEYFKRCANIDLKNVYGNTAEGFHLAT
AGGTWQVLVRGFCGLNVKGNKIELNPNLPEKWKYVKFRIFFKGSWIEFKISRKKVRARM
LEGSRKVKISSFGKEVDLYPGKEVVIVAN
```

Figure 17B

>termocel1_nt (Tce11, o-eglA) 903 bp
ATGATCTATTTTGTTGAGAAATACCACACCTCAGAAGACAAATCCACAAGCAATACCTC
CTCAACCCCCCTCAAACGACACTTAGCACAACAAAGGTTCTCAAAATTCGGTATCCTG
ACGACGGCGAATGGCCTGGCGCTCCCATAGACAAAGACGGCGACGGAAATCCTGAGTTC
TATATCGAAATCAACCTCTGGAACATACTCAACGCGACTGGATTCGCAGAGATGACCTA
TAACTTGACATCTGGCGTTCTCCATTACGTTCAACAACTCGATAATATCGTTCTCCGCG
ATCGCTCAAACTGGGTACATGGCTATCCTGAAATTTTTACGGCAATAAACCCTGGAAC
GCGAATTATGCCACCGACGGCCCGATCCCTCTCCCCAGTAAAGTTTCCAATCTCACAGA
CTTTTACTTGACTATCTCCTACAAGCTTGAACCAAAGAACGGACTCCCTATAAATTTTG
CAATCGAATCTTGGCTTACTAGAGAAGCATGGCGCACTACTGGAATCAACTCCGATGAA
CAGGAAGTAATGATCTGGATTTACTATGACGGACTCCAACCAGCCGGTTCCAAGGTGAA
AGAAATCGTTGTACCTATAATCGTTAATGGCACCCCAGTTAATGCTACCTTCGAAGTGT
GGAAAGCTAATATCGGATGGGAATACGTTGCCTTTAGAATCAAGACACCAATTAAAGAA
GGAACCGTGACAATCCCCTACGGTGCATTCATTAGCGTAGCTGCTAACATTTCTTCCCT
CCCAAATTACACAGAACTTTACCTGGAAGACGTTGAGATAGGCACAGAGTTTGGAACAC
CTTCAACTACTAGCGCACATCTCGAATGGTGGATTACTAACATTACCCTCACCCCACTT
GATCGTCCCCTGATCTCC (SEQ ID NO: 1)
>termocel2_nt (Tce12, petroB) 825 bp
ATGAGGTGGGTAGTTCTTCTGATGGTGGCGTTTTCTGCTCTGCTCTTTTCCTCCGAGGT
GGTTCTCACGAGCGTTGGCGCAGCGGATATCTCCTTCAACGGATTTCCCGTCACCATGG
AGCTCAACTTCTGGAACATAAAGTCGTATGAGGGAGAAACGTGGCTCAAATTCGATGGA
GAAAAGGTTGAGTTCTACGCGGATTTGTACAACATCGTTCTTCAGAATCCAGACAGCTG
GGTGCATGGATATCCGGAGATCTACTACGGTTACAAGCCCTGGGCGAGTCACAACAGCG
GTGTTGAATTTCTTCCTGTGAAGGTGAAAGATCTTCCGGATTTCTACGTGACTCTTGAT
TACTCGATCTGGTACGAAAACAATCTGCCTATCAACCTTGCAATGGAAACATGGATCAC
GAAAAGCCCCGACCAGACTTCTGTTTCTTCGGGTGATGCGGAGATCATGGTTTGGTTTT
ACAACAACGTTCTGATGCCCGGCGGTCAGAAAGTGGATGAGTTCACCACAACAGTTGAG
ATAAACGGAGTGAAGCAGGAAGCAAAATGGGATGTTTACTTCGCACCGTGGAGCTGGCA
TTACCTTGCCTTCAGACTGACAACACCGATGAAAGAAGGAAAGGTGAAGTTCAACGTGA
AGGACTTCGTTCAGAAAGCCGCGGAAGTTGTCAAAAAGCACTCAACGAGAATAGACAAT
TTCGAAGAGCTGTATTTCTGCGTCTGGGAGATCGGGACGGAATTTGGAGATCCAAACAC
AACAACGGCAAAATTCGGCTGGACCTTCAAAGACTTCTTCGTCGAAGTTGTAAAATAA
(SEQ ID NO: 3)

>termocel3_nt (Tce13, ph1171) 1377 bp
ATGGACGGGAATACTATTCTTAAAATCGTACTAATTTGCACTATTTTAGCAGGCCTATT
CGGGCAAGTCGTGCCAGTATATGCAGAAAATACAACATATCAAACACCGACTGGAATTT
ACTACGAAGTGAGAGGAGATACGATATACATGATTAATGTCACCAGTGGAGAGGAAACT
CCCATTCATCTCTTTGGTGTAAACTGGTTTGGCTTTGAAACACCTAATCATGTAGTGCA
CGGACTTTGGAAGAGAAACTGGGAAGACATGCTTCTTCAGATCAAAAGCTTAGGCTTCA
ATGCAATAAGACTTCCTTTCTGTACTGAGTCTGTAAAACCAGGAACACAACCAATTGGA
ATAGATTACAGTAAAAATCCAGATCTTCGTGGACTAGATAGCCTACAGATTATGGAAAA
GATCATAAAGAAGGCCGGAGATCTTGGTATCTTTGTCTTACTCGACTATCATAGGATAG
GATGCACTCACATAGAACCCCTCTGGTACACGGAAGACTTCTCAGAGGAAGACTTTATT
AACACATGGATAGAGGTTGCCAAAAGGTTCGGTAAGTACTGGAACGTAATAGGGGCTGA
TCTAAAGAATGAGCCTCATAGTGTTACCTCACCCCCAGCTGCTTATACAGATGGTACCG

Figure 18A

```
GGGCTACATGGGGTATGGGAAACCCTGCAACCGATTGGAACTTGGCGGCTGAGAGGATA
GGAAAAGCGATTCTGAAGGTTGCCCCTCATTGGTTGATATTCGTGGAGGGGACACAATT
TACTAATCCGAAGACTGACAGTAGTTACAAATGGGGCTACAACGCTTGGTGGGGAGGAA
ATCTAATGGCCGTAAAGGATTATCCAGTTAACTTACCTAGGAATAAGCTAGTATACAGC
CCTCACGTATATGGGCCAGATGTCTATAATCAACCGTACTTTGGTCCCGCTAAGGGTTT
TCCGGATAATCTTCCAGATATCTGGTATCACCACTTTGGATACGTAAAATTAGAACTAG
GATATTCAGTTGTAATAGGAGAGTTTGGAGGAAAATATGGGCATGGAGGCGATCCAAGG
GATGTTATATGGCAAAATAAGCTAGTTGATTGGATGATAGAGAATAAATTTTGTGATTT
CTTTTACTGGAGCTGGAATCCAGATAGTGGAGATACCGGAGGGATTCTACAGGATGATT
GGACAACAATATGGGAAGATAAGTATAATAACCTGAAGAGATTGATGGATAGTTGTTCC
AAAAGTTCTTCAAGTACTCAATCCGTTATTCGGAGTACCACCCCTACAAAGTCAAATAC
AAGTAAGAAGATTTGTGGACCAGCAATTCTTATCATCCTAGCAGTATTCTCTCTTCTCT
TAAGAAGGGCTCCCAGGTAG (SEQ ID NO: 5)
>termocel4_nt (Tcel4, o-El) 1542 bp
ATGGAAATCAAGCTCTTCTGCGTGTTTATCGTGTTCATCATCCTCTTCTCCCCTTTCGT
GATTGCACTCTCGTATCCAGATGTTAACTATACTGCCGAGAATGGTATTATCTTCGTGC
AGAACGTCACTACGGGTGAGAAGAAGCCACTTTATCTTCACGGAGTGTCATGGTTTGGA
TTCGAGCTGAAGGACCACGTCGTCTATGGCTTGGATAAACGGAACTGGAAAGATATACT
CAAGGATGTTAAGCGCTTGGTTTTAATGCTATCAGGCTTCCCTTCTGCTCTGAAAGCA
TCCGCCCTGATACGCGCCTTCGCCTGAGCGGATAAACTACGAGTTGAACCCCGACTTG
AAGAATCTGACTTCCCTCGAAATAATGGAGAAGATTATTGAATACGCCAACTCAATCGG
GCTCTACATACTCTTGGATTATCACCGCATCGGTTGTGAGGAGATCGAACCTCTTTGGT
ATACCGAGAATTACTCAGAGGAGCAGTATATAAAGGATTGGATCTTCCTCGCAAAGCGG
TTCGGGAAGTACCCTAACGTGATAGGAGCTGATATCAAGAACGAGCCGCATGGTGAAGC
CGGGTGGGGTACGGGAGATGAGCGGGATTTCCGCCTCTTTGCCGAGAAGGTCGGGCGCG
AGATACTCAAGGTGGCCCCACACTGGTTGATATTCGTCGAGGGAACGCAATATACCCAT
GTCCCGAATATTGATGAGATCATCGAGAAGAAGGGCTGGTGGACATTTTGGGGAGAGAA
TCTTATGGGAGTTAAGGACTATCCAGTCAGGCTTCCGCGCGGCAAGGTCGTGTACTCAC
CGCATGTCTATGGACCATCTGTCTACATGATGGACTACTTCAAGTCGCCAGACTTTCCG
AACAATATGCCGATAATCTGGGAAACACACTTCGGATACTTGACCGACCTGAATTATAC
CTTGGTCATAGGCGAGTGGGGTGGCAACTATGAGGGCCTTGACAAGGTGTGGCAAGACG
CTTTCGTGAAGTGGCTGATTAAGAAGAAGATCTATAACTTCTTCTACTGGTGCCTGAAC
CCGGAGTCGGGTGACACCGGTGGCATCTTTCTCGACGACTGGAAAACCGTTAACTGGGA
AAAGATGAGGGTTATTTACAGGCTCATCAAGGCGGCGAACCCCGAGTTTGAGGAACCCC
TTTACATCATTTTTGAAAACTAACGCGACGACATCTATCCTGGGCGTGGGTGAGAGGATC
CGGATTTACTGGTACACAAATGGCAAAGTTATTGACTCTAACTTCGCGCATTCCAGCGA
AGGCGAAATGAACATTACAGTGACGAAGTCCATGACTCTGTACATCATCGTGAAGAAGG
GCAATCAGACACTGAGGAAGGAACTCAAACTGTACGTTATCGGCGGCAATTACGGCTCC
AATATCTCCACTACCCAGCTGGTTACTCCCAAGAAAGGCGGCGAAAGGATTAGCACCAG
CCTGAAGCTGGCAATTAGCCTGCTCTTCATTCTCCTCTTCGTTTGGTATCTCCTCCGGG
AGAAGCAT (SEQ ID NO: 7)
>termocel5_nt (Tcel5, petroA) 987 bp
ATGGAAACGCTCCTCCCTGTAGTCGTGGTCCACGATATTGAGCCAGTTTCAATGCGTCT
TCAGAGGTACAAGAACAAAAATTCGATAAAAAGAGAAAAGCAGGGATTAATACCCCTGT
```

Figure 18B

TTTTTATTTTTGGGTGTATTTAGTTCTATTTGCGAATTTTCAGATTTTGAATGTAAAC
ATTTTCATAATAAGATGTTTTCTGGAGGTGATAATGGTGGTACTGATGACAAAACCGGG
AACATCGGATTTTGTATGGAATGGCATTCCCCTTTCCATGGAGCTGAATCTGTGGAACA
TAAAGGAATACTCCGGTTCTGTAGCTATGAAATTCGACGGTGAAAAGGTAACTTTCGAC
GCGGACATTCAGAATCTTTCTCCAAAAGAACCAGAAAGGTACGTTCTCGGTTATCCCGA
GTTCTATTACGGTTATAAACCCTGGGAAAAGCACACGGCAGAAGGTTCGAAACTTCCAG
TACCTGTTTCCTCTATGAAATCATTTTCCGTCGAAGTTTCTTTCGATATTCACCACGAA
CCGTCTCTGCCTTTGAACTTTGCCATGGAAACATGGCTCACAAGAGAAAAGTACCAGAC
GGAAGCGTCGATCGGCGATGTTGAAATCATGGTCTGGTTCTATTTCAACAATCTCACAC
CAGGGGGCAAAAAGATAGAGGAGTTTACGATTCCGTTCGTGCTGAACGGAGAGAGTGTC
GAAGGCACCTGGGAACTGTGGCACGCGGAGTGGGGATGGGACTACCTCGCTTTCCGCTT
GAAGGATCCCGTGAAGAAGGGAAGGGTGAAGTTCGACGTGAGGCATTTTCTTGATGCCG
CCGGGAAGCTCTTTCGAATTCCACTCGTGTGAAAGATTTTGAAAATCTTTACTTCACC
GTCTGGGAAATTGGAACCGAGTTTGGAAGCCCGGAAACAAAGAGCGCGCAATTCGGGTG
GAAGTTTGAAAACTTCTCTATTGATCTGGAGGTGAGAGAATGA (SEQ ID NO: 9)
>termocel6_nt (Tcel6) artificial gene with rice codon
optimization based on *Caldivirga maquilingensis* GH12 gene
852 bp
ATGTTGAAACTTATTCCACTTGTTAATGGCAATTATAAGTTGATTCAATGGGAGCCACT
CGGCGGCGTGCACGGAGCAGATATCGAGTGCATACATGTTACCCCAAACGTATGGAACA
TAGATAAATCATCAGTTGGCACTGTACAGATCGAATATGAGCCCCAAGTTGGCTGTCTT
CGTTTTTCAATTGATTTCCCGAGGATAAGTATAAGACATAATGTAGGCGTAGCGGCATA
TTCAGAAGTTATTTACGGACACAAGCCGTGGGGCCCCACCACTTGCATGGACCCTCAGT
TCAAGTTCCCTATCAAAGTCAATGAGTCAAAAGGACTGTACTCGTATGTAAATTATAAC
GTTAAATCTAGGTCACCAGATGACTCAATCTTTAATATTGCTTACGATCTCTGGCTTAC
AACGTCCCCAAACCTTACAAACGGACCCCAGCCAGGAGACGTAGAAGTTATGATCTGGT
TGTACTACCACGGACAGCGCCCTGCAGGCAGACTCATCGGGGAACTCCGCATGCCGATT
ACATTGGGCGATAGTGAGGCGGCACGTGACTTTGAAGTATGGGTGGCTGACACAGGAAT
AGGAATCGGTGAATGGGCGGTAGTGACCTTCAGAATCAAGGACCCAATAAAGGGCGGTT
TGATAGGAGTTAACCTCATAAACTACATCGAAAGTGCTTTTAAAACGCTCGAAGAACTC
AACCCGGTCAAGTGGCGGTACGGCGACCTGCTCAACAAATATCTTAATGGAATTGAATT
CGGCAGTGAGTTTGGTAATGTCTCCTCAGGAATGATAAAACTTAATTGGGAACTCTGCG
GCCTGAGCCTTGTGAAAGACTCTTCT (SEQ ID NO: 11)
>termocel9_nt (Tcel9) artificial gene with corn codon
optimization based on *Caldivirga maquilingensis* GH12 1230
bp
ATGGACTACTCTATCAACTGCTCTATCAACCCTATAACCCTCATGGTCGCGCACTCTTC
TCCCCTGAACCCATCTAACACACTCGAACTTACACTTATTCTCGAAAATGGCATCACCA
CCACAGTAACTGTCACCGCGACACCACGCAACACTTACCCTATGATCTCCCTTGGCTAC
ATTAATATTACCCCTAACCTCTGGAACCTTAACACAGCTTCGTCATCAGGATACGCCTC
TATGGTCTACGATGCATCACAGGGTGCTCTTTATATTCATGTTAATTTCACAAAGGTTT
ACCTCAATCAGCAAGTTGGTGTTGCCGCCTACTCTGAATTCATCTATGGCTACAAACCC
TGGGGCACGCTCACCTCCGAGGCAGGCGGGTTCAATTTTCCTGTTAAGCTTACCGAACT
CGGTTCTCTTCTTTCGTTCATCAATTACTCACTCATTTCATATTCTCCACAAGTCGCTA
TCTTCGATTGGGCATACGACCTTTGGCTCACAACATCCCCAAATCTCACCAACGGCCCT
CAACCCGGCGACGTCGAGGTCATGATCTGGCTCTATTATCACCTGCAACAACCTGCGGG
TTTTCCCGTCGCTAACGTTACAGTGCCAATATGGGTCAATGGCTCCCTCGTTAACGAAA
CATTTGAGGTTTGGATTGGTTCTCCACAGATCGAACCCGGCACCCACGCTATAGTCTCC

Figure 18C

```
TTCAGGCCAACGAATCCAATCCCTAGAGGCCTCGTCGGCGTAAATGTCACGAAGTTCCT
TCAACTTGCCGTTAACTATCTCGTGACACTCTACCCCTCATACTGGAACTACACATATC
TGGAGAGCAAGTACTTGAATGGCATCGAATTCGGATCAGAATGGGGCAATCCGTCTACA
TACAATATTACACTCAATTGGGTCATTTATAAAGCTTATCTTATCAAGGTGCCTCTGGA
GTCACAGGGCACCGTTACCGTCACATATACTACAACTGTTACATCCACCATGACTGTTA
CCTCAATCCTTGCTACCACATCCACCGTCACCACTACATCTACACTTACATCTACCGTT
ACCGCCACTTCAGTTTCTACTTCCACCGTCACGCAGACTCTCACTACCTCCATCGTCAA
AACCGTCATCCCTGTCTACTATACTGCCACCATAATCGTCCTTCTTATAATCATCGCAG
TCGTCATTGCACTTGCGTTCGCCCGCCGCGGCATCCGGGTTCGTCTCTGT (SEQ ID NO: 29)
>termocel10_nt (Tcel10) Based on Pyrococcus horikoshii OT3
RKU GH65 gene 2214 bp
ATGAGATTTCAATTCGGATTCTCCAAAGAAGATGAACAGGTGCTGGGCACAATACTAAC
ACTCGGAAATGGACAATTAGGAGTTAGGGGAGAATTTGAACTCGAGAGATCTCCTTATG
GAACGATCGTTAGCGGGGTCTATGATTACACTCCCTACTTCTACAGGGAATTGGTAAAT
GGTCCCAGGACTATAGGGATGATAATAATTATAGATGGAGAACTAATAAATCCAAGCTC
TCAAAAAGTCAAGGAATTCCAGAGACAGCTCGATATAGAAAAAGGCTTATTAAGAACTC
ACTTAGAGATTGAAACAAAAAATGGAAATAAAATTTTATATAAAAGTACAAGGATAGTC
CACATGAAAAGAAAAAACCTAATCCTTCTAGATTTTGAGCTAAAAGCTAGCAAGGGAGG
AATCGCAGTTGTAGTTAATCCCATAGAATTCAATACTGCAAATCCAGGGTTTATAGACG
AGATAATGATCAAGCATTATAGAGTGGACTCGATAAAAGAGACTGAGGAGGGAGTATAC
GCTAGGGTGAAAACTTTAGACAATAAGTACACGTTGGAAATTGCAAGTAGCTTGGTTCC
ATCAGAATATACATCGAGGAGCACCTTTAGAACCGATAATGAAATTGGAGAAATTTACA
TTGTTAAACTTAAACCAGGAAAAACGTACAAATTTACAAAGTACGTTACAGTATCTAAA
GGAGCAGCTTTAGAGGAGTTAAAAGATGTTAAGAGATTAGGATTTGAAAAGCTATATGA
AGAGCATATAAACAGCTGGAAGAGAATATGGGAGAAAGTGAAAGTGGAAATCGAAGGAG
ATAAAGACCTTGAAAATGCCCTAAACTTTAACATTTTTCACTTGATCCAATCCCTTCCA
CCAACAGATAAAGTCTCGCTACCAGCAAGGGGAATACATGGGTTTGGGTATAGGGACA
TATATTCTGGGATACAGAGATATATGCATTACCTTTCTTCATATTCACGATGCCAAAAG
AGGCCAGGAGATTGCTCCTCTATAGATGCAACAACTTAGATGCCGCTAAAGAAAATGCA
AAGATGAATGGATATCAAGGGGTCCAATTTCCCTGGGAGTCGGCAGATGATGGACGCGA
GGCTACCCCCTCTGAGATACCATTGGATATGTTGGGAAGCAAAATCGTTAGAATTTACA
CCGGAGAGGAGGAACATCACATAACTGCGGATATAGCATATATAGTTGATTTTTATTAC
CAAGTCTCTGGAGATCTCGAATTTATGAACAGGTGTGGCCTTGAGATAATCTTTGAGAC
GGCCCGATTTTGGGCTAGTAGGGTTGAGTTCGAGGAAGGAAAACGGGTACGTCATTAAAA
AAGTAATAGGACCTGATGAATACCATGAGCACGTTAACAACAACTTCTTTACAAACTTA
ATGGCCAAGCATAATCTCGAACTTGCAATAAGATACTTTAGAGAGTCAAAGAATAGGGA
ACCGTGGAAAAGATTGTCGAAAAATTAAACATAAGAGAGGAGGAGGTTGAAAAATGGG
AAGAGATAGCTAAAAACATGTACATTCCCAGGAAGATAGACGGAGTTTTGAAGAGTTT
GATGGTTACTTTGAATTGATGGATTTTGAAGTTGATCCCTTCAATATTGGAGAAAAAAC
ACTCCCCGAGGAAATCAGGAATAACATAGGGAAAACGAAACTCGTTAAGCAGGCCGATG
TCATCATGGCCCAATATCTCCTTAAGGACTACTTCTCTCCAGAGGAAATAAAGAGTAAC
TTTAACTATTATATAAGGAGAACTACCCATGCTTCATCACTCTCCATGCCCCCATACGC
GATCATTGCAACCTGGATAGGGGAGGTAAAGATAGCATATGAGTACTTCAAGAGATGTG
CAAATATAGATCTCAAAAACGTGTACGGAAACACTGCAGAGGGATTTCACTTAGCAACG
GCGGGAGGAACCTGGCAAGTACTCGTCAGAGGATTTTGTGGCCTCAATGTAAAAGGAAA
```

Figure 18D

```
CAAAATAGAGCTTAATCCTAATCTTCCTGAAAAATGGAAGTACGTTAAGTTCAGGATAT
TCTTCAAAGGTTCATGGATAGAATTTAAAATTTCTAGGAAGAAAGTTAGGGCTAGAATG
CTTGAAGGATCGAGAAAAGTCAAAATATCTAGCTTTGGAAAGGAAGTAGATCTATATCC
TGGAAAAGAGGTTGTAATAGTAGCTAATTAA (SEQ ID NO: 31)
>termocel7_nt (Tcel7) Based on Thermotoga petrophila RKU
GH3 gene 2169 bp
ATGATGGGAAAGATCGATGAAATCCTTTCACAGCTGACTATTGAAGAAAAAGTGAAACT
TGTAGTGGGGGTTGGTCTTCCAGGACTTTTTGGAAATCCACATTCCAGAGTGGCAGGTG
CAGCTGGAGAAACGCATCCTGTTCCGAGGCTTGGAATTCCTTCTTTCGTTCTGGCCGAC
GGTCCCGCGGGCCTCAGAATAAATCCCACAAGAGAGAACGACGAAAACACCTATTACAC
AACAGCGTTTCCTGTTGAAATCATGCTCGCTTCCACCTGGAACAAAGATCTTCTGGAAG
AAGTAGGAAAAGCTATGGGAGAAGAAGTCAGGGAATACGGTGTCGATGTGCTTCTTGCA
CCTGCGATGAACATTCACAGGAACCCTCTTTGTGGAAGGAATTTCGAGTATTATTCAGA
AGATCCTGTCCTTTCCGGTGAAATGGCTTCAGCCTTTGTCAAGGGAGTTCAATCTCAAG
GGGTGGGAGCCTGCATAAAACACTTTGTCGCGAACAACCAGGAAACGAACAGGATGGTA
GTGGACACGATCGTGTCCGAGCGAGCCCTCAGAGAAATATATCTGAAAGGTTTTGAAAT
TGCCGTCAAGAAAGCAAGACCCTGGACCGTGATGAGCGCTTACAACAAACTGAATGGAA
AATACTGTTCACAGAACGAATGGCTTTTGAAGAAGGTTCTCAGGGAAGAATGGGGATTT
GACGGTTTCGTGATGAGCGACTGGTACGCGGGAGACAACCCTGTAGAACAGCTCAAGGC
CGGAAACGATATGATCATGCCTGGAAAAGCGTATCAGGTGAACACGGAAAGAAGAGATG
AAATAGAAGAAATCATGGAGGCGTTGAAGGAGGGAAGACTCAGTGAGGAAGTCCTGAAC
GAATGTGTGAGAAACATCCTCAAAGTTCTTGTGAACGCGCCTTCCTTTAAAGGGTACAG
GTACTCGAACAAACCGGACCTCGAATCTCACGCGAAAGTTGCCTACGAAGCAGGTGTGG
AGGGTGTTGTCCTTCTTGAGAACAACGGTGTTCTTCCATTCGATGAAAGTATCCATGTC
GCCGTCTTTGGCACCGGTCAAATCGAAACAATAAAGGGAGGAACGGGAAGTGGAGACAC
CCATCCGAGATACACGATCTCTATCCTTGAAGGCATAAAAGAAAGAAACATGAAGTTCG
ACGAAGAACTCACCTCCATCTATGAGGATTACATCAAAAAGATGAGAGAAACAGAGGAA
TATAAACCCAGAACTGACTCCTGGGGAACGGTTATAAAACCGAAACTTCCAGAGAACTT
TCTCTCAGAAAAAGAGATAAACAAGGCTGCGAAGAAAAACGATGCTGCAGTTGTTGTAA
TCAGTAGGATCTCCGGTGAGGGATACGACAGAAAGCCGGTGAAAGGTGACTTCTACCTC
TCCGATGACGAGCTGGAGCTCATAAAAACAGTCTCAAGGGAATTCCACGAACAGGGTAA
GAAGGTTGTGGTTCTTCTCAACATCGGAAGTCCCATTGAAGTTGCAAGCTGGAGAGATC
TTGTGGATGGAATCCTTCTCGTCTGGCAAGCAGGACAGGAGATGGGAAGAATAGTGGCC
GATGTTCTTGTGGGAAGGGTAAACCCCTCCGGAAAACTTCCAACGACCTTCCCGAAGGA
TTACTCGGACGTTCCATCCTGGACGTTCCCAGGAGAGCCAAAGGACAATCCGCAAAGAG
TGGTGTACGAGGAAGACATCTACGTGGATACAGGTACTACGACACCTTTGGTGTGGAA
CCTGCCTACGAGTTCGGCTACGGCCTCTCTTACACAAAGTTTGAATACAAAGATTTAAA
GATCGCTATCGACGGAGATATACTCAGAGTGTCGTACACGATCACAAACACCGGGGACA
GAGCTGGAAAGGAAGTCTCACAGGTTTATGTCAAAGCTCCAAAAGGGAAAATAGACAAA
CCCTTCCAGGAGCTGAAAGCGTTCCACAAAACAAAACTTTTGAACCCGGGTGAATCCGA
AAAGATCTTTCTGGAAATTCCTCTTAGAGATCTTGCGAGTTTCGATGGGAAGAATGGG
TTGTCGAGTCAGGAGAATACGAGGTCAGGGTCGGTGCATCTTCGAGGGATATAAGGTTG
AGAGATATTTTCTGGTTGAGGGAGAGAAGAGATTCAAACCATGA (SEQ ID NO: 13)
>termocel8_nt (Tcel8) Based on Thermotoga petrophila RKU
GH1 gene 1341 bp
```

Figure 18E

```
ATGAACGTGAAAAAGTTCCCTGAAGGATTCCTCTGGGGTGTTGCAACAGCTTCCTACCA
GATCGAGGGTTCTCCCCTCGCAGACGGAGCTGGTATGTCTATCTGGCACACCTTCTCCC
ATACTCCTGGAAATGTAAAGAACGGTGACACGGGAGATGTGGCCTGCGACCACTACAAC
AGATGGAAAGAGGACATTGAAATCATAGAGAAACTCGGAGTAAAGGCTTACAGATTTTC
AATCAGCTGGCCAAGAATACTTCCGGAAGGAACAGGAAGGGTGAATCAGAAAGGACTGG
ATTTTTACAACAGGATCATAGACACCCTGCTGGAAAAAGGTATCACACCCTTTGTGACC
ATCTATCACTGGGATCTTCCCTTCGCTCTTCAGTTGAAAGGAGGATGGGCGAACAGAGA
AATAGCGGATTGGTTCGCAGAATACTCAAGGGTTCTCTTTGAAAATTTCGGCGACCGTG
TGAAGAACTGGATCACCTTGAACGAACCGTGGGTTGTTGCCATAGTGGGGCATCTGTAC
GGAGTCCACGCTCCTGGAATGAGAGATATTTACGTGGCTTTCCGAGCTGTTCACAATCT
CTTGAGGGCACACGCCAAAGCGGTGAAAGTGTTCAGGGAAACTGTGAAAGATGGAAAGA
TCGGAATAGTTTTCAACAATGGATATTTCGAACCTGCGAGTGAAAAGAGGAGGACATC
AGAGCGGCGAGATTCATGCATCAGTTCAACAACTATCCTCTCTTTCTCAATCCGATCTA
CAGAGGAGATTATCCGGAGCTCGTTCTGGAATTTGCCAGAGAGTATCTACCGGAGAATT
ACAAAGATGACATGTCCGAGATACAGGAAAAGATCGACTTTGTTGGATTGAACTATTAC
TCCGGTCATTTGGTGAAGTTCGATCCAGATGCACCAGCTAAGGTCTCTTTCGTTGAAAG
GGATCTTCCAAAAACAGCCATGGGATGGGAGATCGTTCCAGAAGGAATCTACTGGATCC
TGAAGAAGGTGAAAGAAGAATACAACCCACCAGAGGTTTACATCACAGAGAATGGGGCT
GCTTTTGACGACGTAGTTAGTGAAGATGGAAGAGTTCACGATCAAAACAGAATCGATTA
TTTGAAGGCCCACATTGGTCAGGCATGGAAGGCCATACAGGAGGGAGTGCCGCTTAAAG
GTTACTTCGTCTGGTCGCTCCTCGACAATTTCGAATGGGCAGAGGGATATTCCAAGAGA
TTTGGTATTGTGTACGTGGACTACAGTACTCAAAAACGCATCATAAAAGACAGTGGTTA
CTGGTACTCGAACGTGGTCAAAAGCAACAGTCTGGAAGATTGA(SEQ ID NO: 15)
>pBAD MYC-HIS TAG 66 bp
GAACAAAAACTCATCTCAGAAGAGGATCTGAATAGCGCCGTCGACCATCATCATCATCA
TCATCAT (SEQ ID NO: 17)
```

Figure 18F

>termocell_aa (Tcel1, o-eglA) endoglucanase 301 aa (WITHOUT
N-TERMINAL SIGNAL PEPTIDE, CODONS OPTIMIZED FOR CORN), GH12,
MW 34,005, pI 4.80, charge -13.10
MIYFVEKYHTSEDKSTSNTSSTPPQTTLSTTKVLKIRYPDDGEWPGAPIDKDGDGNPEF
YIEINLWNILNATGFAEMTYNLTSGVLHYVQQLDNIVLRDRSNWVHGYPEIFYGNKPWN
ANYATDGPIPLPSKVSNLTDFYLTISYKLEPKNGLPINFAIESWLTREAWRTTGINSDE
QEVMIWIYYDGLQPAGSKVKEIVVPIIVNGTPVNATFEVWKANIGWEYVAFRIKTPIKE
GTVTIPYGAFISVAANISSLPNYTELYLEDVEIGTEFGTPSTTSAHLEWWITNITLTPL
DRPLIS (SEQ ID NO: 2)
>termocel2_aa (Tcel2, petroB), endoglucanase, 274 aa, GH12,
MW 38,226, pI 5.58, charge -6.60
MRWVVLLMVAFSALLFSSEVVLTSVGAADISFNGFPVTMELNFWNIKSYEGETWLKFDG
EKVEFYADLYNIVLQNPDSWVHGYPEIYYGYKPWASHNSGVEFLPVKVKDLPDFYVTLD
YSIWYENNLPINLAMETWITKSPDQTSVSSGDAEIMVWFYNNVLMPGGQKVDEFTTTVE
INGVKQEAKWDVYFAPWSWDYLAFRLTTPMKEGKVKFNVKDFVQKAAEVVKKHSTRIDN
FEELYFCVWEIGTEFGDPNTTTAKFGWTFKDFFVEVVK (SEQ ID NO: 4)
>termocel3_aa (Tcel3, ph1171) exocellulase 458 aa, GH5, MW
51,930, pI 6.47, charge -3.60
MEGNTILKIVLICTILAGLFGQVVPVYAENTTYQTPTGIYYEVRGDTIYMINVTSGEET
PIHLFGVNWFGFETPNHVVHGLWKRNWEDMLLQIKSLGFNAIRLPFCTESVKPGTQPIG
IDYSKNPDLRGLDSLQIMEKIIKKAGDLGIFVLLDYHRIGCTHIEPLWYTEDFSEEDFI
NTWIEVAKRFGKYWNVIGADLKNEPHSVTSPPAAYTDGTGATWGMGNPATDWNLAAERI
GKAILKVAPHWLIFVEGTQFTNPKTDSSYKWGYNAWWGGNLMAVKDYPVNLPRNKLVYS
PHVYGPDVYNQPYFGPAKGFPDNLPDIWYHHFGYVKLELGYSVVIGEFGGKYGHGGDPR
DVIWQNKLVDWMIENKFCDFFYWSWNPDSGDTGGILQDDWTTIWEDKYNNLKRLMDSCS
KSSSSTQSVIRSTTPTKSNTSKKICGPAILIILAVFSLLLRRAPR (SEQ ID NO: 6)
>termocel4_aa (Tcel4, o-E1) exocellulase 514 aa (CODONS
OPTIMIZED FOR RICE, WITHOUT STOP CODON), GH5, MW 59,980, pI
7.05, charge 0.30
MEIKLFCVFIVFIILFSPFVIALSYPDVNYTAENGIIFVQNVTTGEKKPLYLHGVSWFG
FELKDHVVYGLDKRNWKDILKDVKRLGFNAIRLPFCSESIRPDTRPSPERINYELNPDL
KNLTSLEIMEKIIEYANSIGLYILLDYHRIGCEEIEPLWYTENYSEEQYIKDWIFLAKR
FGKYPNVIGADIKNEPHGEAGWGTGDERDFRLFAEKVGREILKVAPHWLIFVEGTQYTH
VPNIDEIIEKKGWWTFWGENLMGVKDYPVRLPRGKVVYSPHVYGPSVYMMDYFKSPDFP
NNMPIIWETHFGYLTDLNYTLVIGEWGGNYEGLDKVWQDAFVKWLIKKKIYNFFYWCLN
PESGDTGGIFLDDWKTVNWEKMRVIYRLIKAANPEFEEPLYIILKTNATTSILGVGERI
RIYWYTNGKVIDSNFAHSSEGEMNITVTKSMTLYIIVKKGNQTLRKELKLYVIGGNYGS
NISTTQLVTPKKGGERISTSLKLAISLLFILLFVWYLLREKH (SEQ ID NO: 8)
>termoel5_aa (Tcel5, petroA) endoglucanase 328 aa, GH12, MW
38,226, pI 5.58, charge -6.60
METLLPVVVVHDIEPVSMRLQRYKNKNSIKREKQGLIPLFFYFWVYLVLFANFQILNVN
IFIIRCFLEVIMVVLMTKPGTSDFVWNGIPLSMELNLWNIKEYSGSVAMKFDGEKVTFD
ADIQNLSPKEPERYVLGYPEFYYGYKPWEKHTAEGSKLPVPVSSMKSFSVEVSFDIHHE
PSLPLNFAMETWLTREKYQTEASIGDVEIMVWFYNNLTPGGKKIEEFTIPFVLNGESV
EGTWELWHAEWGWDYLAFRLKDPVKKGRVKFDVRHFLDAAGKALSNSTRVKDFENLYFT
VWEIGTEFGSPETKSAQFGWKFENFSIDLEVRE (SEQ ID NO: 10)

Figure 19A

| GH12 | 31,818 | -5.66 | 5.00 |

\>termoel6_aa (Tcel6) endoglucanase 284 aa (CODONS OPTIMIZED
FOR CORN), GH12, MW 31,818, pI 5.66, charge -5.00
MLKLIPLVNGNYKLIQWEPLGGVHGADIECIHVTPNVWNIDKSSVGTVQIEYEPQVGCL
RFSIDFPRISIRHNVGVAAYSEVIYGHKPWGPTTCMDPQFKFPIKVNESKGLYSYVNYN
VKSRSPDDSIFNIAYDLWLTTSPNLTNGPQPGDVEVMIWLYYHGQRPAGRLIGELRMPI
TLGDSEAARDFEVWVADTGIGIGEWAVVTFRIKDPIKGGLIGVNLINYIESAFKTLEEL
NPVKWRYGDLLNKYLNGIEFGSEFGNVSSGMIKLNWELCGLSLVKDSS (SEQ ID NO: 12)

\>termocel9_aa (Tcel9) endoglucanase 410 aa (CODONS
OPTIMIZED FOR CORN), GH12, MW 45,059, pI 6.16, charge -2.20
MDYSINCSINPITLMVAHSSPLNPSNTLELTLILENGITTTVTVTATPRNTYPMISLGY
INITPNLWNLNTASSSGYASMVYDASQGALYIHVNFTKVYLNQQVGVAAYSEFIYGYKP
WGTLTSEAGGFNFPVKLTELGSLLSFINYSLISYSPQVAIFDWAYDLWLTTSPNLTNGP
QPGDVEVMIWLYYHLQQPAGFPVANVTVPIWVNGSLVNETFEVWIGSPQIEPGTHAIVS
FRPTNPIPRGLVGVNVTKFLQLAVNYLVTLYPSYWNYTYLESKYLNGIEFGSEWGNPST
YNITLNWVIYKAYLIKVPLESQGTVTVTYTTTVTSTMTVTSILATTSTVTTTSTLTSTV
TATSVSTSTVTQTLTTSIVKTVIPVYYTATIIVLLIIIAVVIALAFARRGIRVRLC (SEQ ID NO 30)

\>termocel10_aa (Tcel10) endoglucanase 737 aa, GH65, MW
85,598, pI 7.80, charge 4.30
MRFQFGFSKEDEQVLGTILTLGNQLGVRGEFELERSPYGTIVSGVYDYTPYFYRELVN
GPRTIGMIIIDGELINPSSQKVKEFQRELDIEKGLLRTHLEIETKNGNKILYKSTRIV
HMKRKNLILLDPELKASKGGIAVVVNPIEFNTANPGFIDEIMIKHYRVDSIKETEEGVY
ARVKTLDNKYTLEIASSLVPSEYTSRSTFRTDNEIGEIYIVKLKPGKTYKFTKYVTVSK
GAALEELKDVKRLGFEKLYEEHINSWKRIWEKVKVEIEGDKDLENALNFNIFHLIQSLP
PTDKVSLPARGIHGFGYRGHIFWDTEIYALPFFIPTMPKEARRLLLYRCNNLDAAKENA
KMNGYQGVQFPWESADDGREATPSEIPLDMLGRKIVRIYTGEEEHHITADIAYIVDFYY
QVSGDLEFMNRCGLEIIFETARFWASRVEFEEGKGYVIKKVIGPDEYHEHVNNNFFTNL
MAKHNLELAIRYFRESKNREPWKKIVEKLNIREEEVEKWEEIAKNMYIPRKIDGVFEEF
DGYFELMDFEVDPFNIGEKTLPEEIRNNIGKTKLVKQADVIMAQYLLKDYFSPEEIKSN
FNYYIRRTTHASSLSMPPYAIIATWIGEVKIAYEYFKRCANIDLKNVYGNTAEGFHLAT
AGGTWQVLVRGFCGLNVKGNKIELNPNLPEKWKYVKFRIFFKGSWIEFKISRKKVRARM
LEGSRKVKISSFGKEVDLYPGKEVVIVAN (SEQ ID NO: 32)

\>termocel7_aa (Tcel7) beta-glucosidase 722 aa, GH3, MW
81,243, pI 5.38, charge -16.9
MMGKIDEILSQLTIEEKVKLVVGVGLPGLFGNPHSRVAGAAGETHPVPRLGIPSFVLAD
GPAGLRINPTRENDENTYYTTAFPVEIMLASTWNKDLLEEVGKAMGEEVREYGVDVLLA
PAMNIHRNPLCGRNFEYYSEDPVLSGEMASAFVKGVQSQGVGACIKHFVANNQETNRMV
*VDTIVSERALREIYLKGFEIAVKKARPWTVMSAYNKLNGKYCSQNEWLLKKVLREEWGF*
DGFVMSDWYAGDNPVEQLKAGNDMIMPGKAYQVNTERRDEIEEIMEALKEGRLSEEVLN
ECVRNILKVLVNAPSFKGYRYSNKPDLESHAKVAYEAGVEGVVLLENNGVLPFDESIHV
AVFGTGQIETIKGGTGSGDTHPRYTISILEGIKERNMKFDEELTSIYEDYIKKMRETEE
YKPRTDSWGTVIKPKLPENFLSEKEIKKAAKKNDAAVVVISRISGEGYDRKPVKGDFYL
SDDELELIKTVSREFHEQGKKVVVLLNIGSPIEVASWRDLVDGILLVWQAGQEMGRIVA
DVLVGRVNPSGKLPTTFPKDYSDVPSWTFPGEPKDNPQRVVYEEDIYVGYRYYDTFGVE
PAYEFGYGLSYTKFEYKDLKIAIDGDILRVSYTITNTGDRAGKEVSQVYVKAPKGKIDK
PFQELKAFHKTKLLNPGESEKIFLEIPLRDLASFDGKEWVVESGEYEVRVGASSRDIRL
RDIFLVEGEKRFK (SEQ ID NO: 14)

Figure 19B

>termocel8_aa (Tcel8) beta-glucosidase 446 aa, GH1, MW 51509, pI 5.84, charge -9.1
MNVKKFPEGFLWGVATASYQIEGSPLADGAGMSIWHTFSHTPGNVKNGDTGDVACDHYN
RWKEDIEIIEKLGVKAYRFSISWPRILPEGTGRVNQKGLDFYNRIIDTLLEKGITPFVT
IYHWDLPFALQLKGGWANREIADWFAEYSRVLFENFGDRVKNWITLNEPWVVAIVGHLY
GVHAPGMRDIYVAFRAVHNLLRAHAKAVKVFRETVKDGKIGIVFNNGYFEPASEKEEDI
RAARFMHQFNNYPLFLNPIYRGDYPELVLEFAREYLPENYKDDMSEIQEKIDFVGLNYY
SGHLVKFDPDAPAKVSFVERDLPKTAMGWEIVPEGIYWILKKVKEEYNPPEVYITENGA
AFDDVVSEDGRVHDQNRIDYLKAHIGQAWKAIQEGVPLKGYFVWSLLDNFEWAEGYSKR
FGIVYVDYSTQKRIIKDSGYWYSNVVKSNSLED (SEQ ID NO: 16)
>pBAD MYC-HIS TAG 21 aa, MW 2,513, pI 6.20 charge -2.60
EQKLISEEDLNSAVDHHHHHH (SEQ ID NO: 18)

Figure 19C

SEQUENCE LISTING

<160> NUMBER OF SEQ ID NOS: 32

<210> SEQ ID NO 1
<211> LENGTH: 903
<212> TYPE: DNA
<213> ORGANISM: Pyrococcus furiosus

<400> SEQUENCE: 1

| | | | | | |
|---|---|---|---|---|---|
| atgatctatt | ttgttgagaa | ataccacacc | tcagaagaca | aatccacaag | caatacctcc | 60 |
| tcaaccccc | ctcaaacgac | acttagcaca | acaaaggttc | tcaaaattcg | gtatcctgac | 120 |
| gacggcgaat | ggcctggcgc | tcccatagac | aaagacggcg | acggaaatcc | tgagttctat | 180 |
| atcgaaatca | acctctggaa | catactcaac | gcgactggat | tcgcagagat | gacctataac | 240 |
| ttgacatctg | gcgttctcca | ttacgttcaa | caactcgata | atatcgttct | ccgcgatcgc | 300 |
| tcaaactggg | tacatggcta | tcctgaaatt | ttttacggca | ataaaccctg | gaacgcgaat | 360 |
| tatgccaccg | acggcccgat | ccctctcccc | agtaaagttt | ccaatctcac | agacttttac | 420 |
| ttgactatct | cctacaagct | tgaaccaaag | aacggactcc | ctataaattt | tgcaatcgaa | 480 |
| tcttggctta | ctagagaagc | atggcgcact | actggaatca | actccgatga | acaggaagta | 540 |
| atgatctgga | tttactatga | cggactccaa | ccagccggtt | ccaaggtgaa | agaaatcgtt | 600 |
| gtacctataa | tcgttaatgg | cacccagtt | aatgctacct | tcgaagtgtg | aaagctaat | 660 |
| atcggatggg | aatacgttgc | ctttagaatc | aagacaccaa | ttaaagaagg | aaccgtgaca | 720 |
| atccctacg | gtgcattcat | tagcgtagct | gctaacattt | cttccctccc | aaattacaca | 780 |
| gaactttacc | tggaagacgt | tgagataggc | acagagtttg | aacaccttc | aactactagc | 840 |
| gcacatctcg | aatggtggat | tactaacatt | accctcaccc | cacttgatcg | tccctgatc | 900 |
| tcc | | | | | | 903 |

<210> SEQ ID NO 2
<211> LENGTH: 301
<212> TYPE: PRT
<213> ORGANISM: Pyrococcus furiosus

<400> SEQUENCE: 2

Met Ile Tyr Phe Val Glu Lys Tyr His Thr Ser Glu Asp Lys Ser Thr
1               5                   10                  15

Ser Asn Thr Ser Ser Thr Pro Pro Gln Thr Thr Leu Ser Thr Thr Lys
            20                  25                  30

Val Leu Lys Ile Arg Tyr Pro Asp Asp Gly Glu Trp Pro Gly Ala Pro
        35                  40                  45

Ile Asp Lys Asp Gly Asp Gly Asn Pro Glu Phe Tyr Ile Glu Ile Asn
    50                  55                  60

Leu Trp Asn Ile Leu Asn Ala Thr Gly Phe Ala Glu Met Thr Tyr Asn
65                  70                  75                  80

Leu Thr Ser Gly Val Leu His Tyr Val Gln Gln Leu Asp Asn Ile Val
                85                  90                  95

Leu Arg Asp Arg Ser Asn Trp Val His Gly Tyr Pro Glu Ile Phe Tyr
            100                 105                 110

Gly Asn Lys Pro Trp Asn Ala Asn Tyr Ala Thr Asp Gly Pro Ile Pro
        115                 120                 125

Leu Pro Ser Lys Val Ser Asn Leu Thr Asp Phe Tyr Leu Thr Ile Ser
    130                 135                 140

Tyr Lys Leu Glu Pro Lys Asn Gly Leu Pro Ile Asn Phe Ala Ile Glu
145                 150                 155                 160

```
Ser Trp Leu Thr Arg Glu Ala Trp Arg Thr Thr Gly Ile Asn Ser Asp
            165                 170                 175

Glu Gln Glu Val Met Ile Trp Ile Tyr Tyr Asp Gly Leu Gln Pro Ala
            180                 185                 190

Gly Ser Lys Val Lys Glu Ile Val Pro Ile Ile Val Asn Gly Thr
            195                 200                 205

Pro Val Asn Ala Thr Phe Glu Val Trp Lys Ala Asn Ile Gly Trp Glu
    210                 215                 220

Tyr Val Ala Phe Arg Ile Lys Thr Pro Ile Lys Glu Gly Thr Val Thr
225                 230                 235                 240

Ile Pro Tyr Gly Ala Phe Ile Ser Val Ala Ala Asn Ile Ser Ser Leu
                245                 250                 255

Pro Asn Tyr Thr Glu Leu Tyr Leu Glu Asp Val Glu Ile Gly Thr Glu
            260                 265                 270

Phe Gly Thr Pro Ser Thr Thr Ser Ala His Leu Glu Trp Trp Ile Thr
                275                 280                 285

Asn Ile Thr Leu Thr Pro Leu Asp Arg Pro Leu Ile Ser
            290                 295                 300

<210> SEQ ID NO 3
<211> LENGTH: 825
<212> TYPE: DNA
<213> ORGANISM: Thermotoga petrophila

<400> SEQUENCE: 3
atgaggtggg tagttcttct gatggtggcg ttttctgctc tgctctttc ctccgaggtg      60 gttctcacga gcgttggcgc agcggatatc tccttcaacg atttcccgt caccatggag    120 ctcaacttct ggaacataaa gtcgtatgag gagaaacgt ggctcaaatt cgatggagaa    180
aaggttgagt tctacgcgga tttgtacaac atcgttcttc agaatccaga cagctgggtg    240
catggatatc cggagatcta ctacggttac aagccctggg cgagtcacaa cagcggtgtt    300
gaatttcttc ctgtgaaggt gaaagatctt ccggatttct acgtgactct tgattactcg    360
atctggtacg aaaacaatct gcctatcaac cttgcaatgg aaacatggat cacgaaaagc    420
cccgaccaga cttctgtttc ttcgggtgat gcggagatca tggtttggtt ttacaacaac    480
gttctgatgc ccggcggtca gaaagtggat gagttcacca acagttga gataaacgga    540 gtgaagcagg aagcaaaatg ggatgtttac ttcgcaccgt ggagctggga ttaccttgcc    600
ttcagactga caacaccgat gaagaagga aaggtgaagt tcaacgtgaa ggacttcgtt    660
cagaaagccg cggaagttgt caaaaagcac tcaacgagaa tagacaattt cgaagagctg    720
tatttctgcg tctgggagat cgggacggaa tttggagatc caaacacaac aacggcaaaa    780
ttcggctgga ccttcaaaga cttcttcgtc gaagttgtaa aataa                     825

<210> SEQ ID NO 4
<211> LENGTH: 274
<212> TYPE: PRT
<213> ORGANISM: Thermotoga petrophila

<400> SEQUENCE: 4

Met Arg Trp Val Val Leu Leu Met Val Ala Phe Ser Ala Leu Leu Phe
1               5                   10                  15

Ser Ser Glu Val Val Leu Thr Ser Val Gly Ala Ala Asp Ile Ser Phe
            20                  25                  30

Asn Gly Phe Pro Val Thr Met Glu Leu Asn Phe Trp Asn Ile Lys Ser
```

```
                  35                  40                  45
Tyr Glu Gly Glu Thr Trp Leu Lys Phe Asp Gly Glu Lys Val Glu Phe
 50                  55                  60

Tyr Ala Asp Leu Tyr Asn Ile Val Leu Gln Asn Pro Asp Ser Trp Val
 65                  70                  75                  80

His Gly Tyr Pro Glu Ile Tyr Gly Tyr Lys Pro Trp Ala Ser His
                 85                  90                  95

Asn Ser Gly Val Glu Phe Leu Pro Val Lys Val Lys Asp Leu Pro Asp
                100                 105                 110

Phe Tyr Val Thr Leu Asp Tyr Ser Ile Trp Tyr Glu Asn Asn Leu Pro
                115                 120                 125

Ile Asn Leu Ala Met Glu Thr Trp Ile Thr Lys Ser Pro Asp Gln Thr
        130                 135                 140

Ser Val Ser Ser Gly Asp Ala Glu Ile Met Val Trp Phe Tyr Asn Asn
145                 150                 155                 160

Val Leu Met Pro Gly Gly Gln Lys Val Asp Glu Phe Thr Thr Thr Val
                165                 170                 175

Glu Ile Asn Gly Val Lys Gln Glu Ala Lys Trp Asp Val Tyr Phe Ala
                180                 185                 190

Pro Trp Ser Trp Asp Tyr Leu Ala Phe Arg Leu Thr Thr Pro Met Lys
                195                 200                 205

Glu Gly Lys Val Lys Phe Asn Val Lys Asp Phe Val Gln Lys Ala Ala
        210                 215                 220

Glu Val Val Lys Lys His Ser Thr Arg Ile Asp Asn Phe Glu Glu Leu
225                 230                 235                 240

Tyr Phe Cys Val Trp Glu Ile Gly Thr Glu Phe Gly Asp Pro Asn Thr
                245                 250                 255

Thr Thr Ala Lys Phe Gly Trp Thr Phe Lys Asp Phe Val Glu Val
        260                 265                 270

Val Lys

<210> SEQ ID NO 5
<211> LENGTH: 1377
<212> TYPE: DNA
<213> ORGANISM: Pyrococcus horikoshii

<400> SEQUENCE: 5
atggagggga atactattct taaaatcgta ctaatttgca ctattttagc aggcctattc      60
gggcaagtcg tgccagtata tgcagaaaat acaacatatc aaacaccgac tggaatttac     120
tacgaagtga gaggagatac gatatacatg attaatgtca ccagtggaga ggaaactccc     180
attcatctct tggtgtaaa ctggtttggc tttgaaacac taatcatgt agtgcacgga      240 ctttggaaga gaaactggga agacatgctt cttcagatca aaagcttagg cttcaatgca     300
ataagacttc ctttctgtac tgagtctgta aaaccaggaa cacaaccaat tggaatagat     360
tacagtaaaa atccagatct tcgtggacta gatagcctac agattatgga aaagatcata     420
aagaaggccg agatcttgg tatctttgtc ttactcgact atcataggat aggatgcact     480
cacatagaac cctctggta cacggaagac ttctcagagg aagactttat taacacatgg     540
atagaggttg ccaaaaggtt cggtaagtac tggaacgtaa taggggctga tctaaagaat     600
gagcctcata gtgttacctc accccagct gcttatacag atggtaccgg ggctacatgg     660 ggtatggaa accctgcaac cgattggaac ttggcggctg agaggatagg aaaagcgatt     720
ctgaaggttg cccctcattg gttgatattc gtggagggga cacaatttac taatccgaag     780
```

```
actgacagta gttacaaatg gggctacaac gcttggtggg gaggaaatct aatggccgta      840
aaggattatc cagttaactt acctaggaat aagctagtat acagccctca cgtatatggg      900
ccagatgtct ataatcaacc gtactttggt cccgctaagg gttttccgga taatcttcca      960
gatatctggt atcaccactt tggatacgta aaattagaac taggatattc agttgtaata     1020
ggagagtttg gaggaaaata tgggcatgga ggcgatccaa gggatgttat atggcaaaat     1080
aagctagttg attggatgat agagaataaa ttttgtgatt tcttttactg gagctggaat     1140
ccagatagtg gagataccgg agggattcta caggatgatt ggacaacaat atgggaagat     1200
aagtataata acctgaagag attgatggat agttgttcca aaagttcttc aagtactcaa     1260
tccgttattc ggagtaccac ccctacaaag tcaaatacaa gtaagaagat tgtggacca     1320 gcaattctta tcatcctagc agtattctct cttctcttaa gaagggctcc caggtag        1377
```

<210> SEQ ID NO 6
<211> LENGTH: 458
<212> TYPE: PRT
<213> ORGANISM: Pyrococcus horikoshii

<400> SEQUENCE: 6

```
Met Glu Gly Asn Thr Ile Leu Lys Ile Val Leu Ile Cys Thr Ile Leu
 1               5                  10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
    50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205

Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270
```

Trp Gly Gly Asn Leu Met Ala Val Lys Asp Tyr Pro Val Asn Leu Pro
            275                 280                 285

Arg Asn Lys Leu Val Tyr Ser Pro His Val Tyr Gly Pro Asp Val Tyr
    290                 295                 300

Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
                325                 330                 335

Ser Val Val Ile Gly Glu Phe Gly Gly Lys Tyr Gly His Gly Gly Asp
                340                 345                 350

Pro Arg Asp Val Ile Trp Gln Asn Lys Leu Val Asp Trp Met Ile Glu
            355                 360                 365

Asn Lys Phe Cys Asp Phe Phe Tyr Trp Ser Trp Asn Pro Asp Ser Gly
    370                 375                 380

Asp Thr Gly Gly Ile Leu Gln Asp Asp Trp Thr Thr Ile Trp Glu Asp
385                 390                 395                 400

Lys Tyr Asn Asn Leu Lys Arg Leu Met Asp Ser Cys Ser Lys Ser Ser
                405                 410                 415

Ser Ser Thr Gln Ser Val Ile Arg Ser Thr Thr Pro Thr Lys Ser Asn
            420                 425                 430

Thr Ser Lys Lys Ile Cys Gly Pro Ala Ile Leu Ile Ile Leu Ala Val
    435                 440                 445

Phe Ser Leu Leu Leu Arg Arg Ala Pro Arg
    450                 455

<210> SEQ ID NO 7
<211> LENGTH: 1542
<212> TYPE: DNA
<213> ORGANISM: Pyrococcus abyssi

<400> SEQUENCE: 7

```
atggaaatca agctcttctg cgtgtttatc gtgttcatca tcctcttctc ccctttcgtg      60
attgcactct cgtatccaga tgttaactat actgccgaga atggtattat cttcgtgcag     120
aacgtcacta cgggtgagaa gaagccactt tatcttcacg gagtgtcatg gtttggattc     180
gagctgaagg accacgtcgt ctatggcttg ataaacgga actggaaaga tatactcaag     240
gatgttaagc gcttgggttt taatgctatc aggcttccct tctgctctga agcatccgc     300 cctgatacgc gcccttcgcc tgagcggata aactacgagt tgaaccccga cttgaagaat     360
ctgacttccc tcgaaataat ggagaagatt attgaatacg ccaactcaat cgggctctac     420
atactcttgg attatcaccg catcggttgt gaggagatcg aacctctttg gtataccgag     480
aattactcag aggagcagta tataaaggat tggatcttcc tcgcaaagcg gttcgggaag     540
taccctaacg tgataggagc tgatatcaag aacgagccgc atggtgaagc cgggtggggt     600
acgggagatg agcggatttt ccgcctcttt gccgagaagg tcgggcgcga tactcaag      660 gtggccccac actggttgat attcgtcgag ggaacgcaat atacccatgt cccgaatatt     720
gatgagatca tcgagaagaa gggctggtgg acattttggg gagagaatct tatgggagtt     780
aaggactatc cagtcaggct tccgcgcggc aaggtcgtgt actcaccgca tgtctatgga     840
ccatctgtct acatgatgga ctacttcaag tcgccagact ttccgaacaa tatgccgata     900
atctgggaaa cacacttcgg atacttgacc gacctgaatt ataccttggt cataggcgag     960
tggggtggca actatgaggg ccttgacaag gtgtggcaag acgctttcgt gaagtggctg    1020
```

-continued

```
attaagaaga agatctataa cttcttctac tggtgcctga acccgagtc  gggtgacacc    1080 ggtggcatct ttctcgacga ctggaaaacc gttaactggg aaaagatgag ggttatttac    1140
aggctcatca aggcggcgaa ccccgagttt gaggaacccc tttacatcat tttgaaaact    1200
aacgcgacga catctatcct gggcgtgggt gagaggatcc ggatttactg gtacacaaat    1260
ggcaaagtta ttgactctaa cttcgcgcat tccagcgaag gcgaaatgaa cattacagtg    1320
acgaagtcca tgactctgta catcatcgtg aagaagggca atcagacact gaggaaggaa    1380
ctcaaactgt acgttatcgg cggcaattac ggctccaata tctccactac ccagctggtt    1440
actcccaaga aggcggcga  aaggattagc accagcctga agctggcaat tagcctgctc    1500
ttcattctcc tcttcgtttg gtatctcctc cgggagaagc at                       1542
```

<210> SEQ ID NO 8
<211> LENGTH: 514
<212> TYPE: PRT
<213> ORGANISM: Pyrococcus abyssi

<400> SEQUENCE: 8

```
Met Glu Ile Lys Leu Phe Cys Val Phe Ile Val Phe Ile Ile Leu Phe
1               5                   10                  15

Ser Pro Phe Val Ile Ala Leu Ser Tyr Pro Asp Val Asn Tyr Thr Ala
            20                  25                  30

Glu Asn Gly Ile Ile Phe Val Gln Asn Val Thr Thr Gly Glu Lys Lys
        35                  40                  45

Pro Leu Tyr Leu His Gly Val Ser Trp Phe Gly Phe Glu Leu Lys Asp
    50                  55                  60

His Val Val Tyr Gly Leu Asp Lys Arg Asn Trp Lys Asp Ile Leu Lys
65                  70                  75                  80

Asp Val Lys Arg Leu Gly Phe Asn Ala Ile Arg Leu Pro Phe Cys Ser
                85                  90                  95

Glu Ser Ile Arg Pro Asp Thr Arg Pro Ser Pro Glu Arg Ile Asn Tyr
            100                 105                 110

Glu Leu Asn Pro Asp Leu Lys Asn Leu Thr Ser Leu Glu Ile Met Glu
        115                 120                 125

Lys Ile Ile Glu Tyr Ala Asn Ser Ile Gly Leu Tyr Ile Leu Leu Asp
    130                 135                 140

Tyr His Arg Ile Gly Cys Glu Glu Ile Glu Pro Leu Trp Tyr Thr Glu
145                 150                 155                 160

Asn Tyr Ser Glu Glu Gln Tyr Ile Lys Asp Trp Ile Phe Leu Ala Lys
                165                 170                 175

Arg Phe Gly Lys Tyr Pro Asn Val Ile Gly Ala Asp Ile Lys Asn Glu
            180                 185                 190

Pro His Gly Glu Ala Gly Trp Gly Thr Gly Asp Glu Arg Asp Phe Arg
        195                 200                 205

Leu Phe Ala Glu Lys Val Gly Arg Glu Ile Leu Lys Val Ala Pro His
    210                 215                 220

Trp Leu Ile Phe Val Glu Gly Thr Gln Tyr Thr His Val Pro Asn Ile
225                 230                 235                 240

Asp Glu Ile Ile Glu Lys Lys Gly Trp Trp Thr Phe Trp Gly Glu Asn
                245                 250                 255

Leu Met Gly Val Lys Asp Tyr Pro Val Arg Leu Pro Arg Gly Lys Val
            260                 265                 270

Val Tyr Ser Pro His Val Tyr Gly Pro Ser Val Tyr Met Met Asp Tyr
        275                 280                 285
```

```
Phe Lys Ser Pro Asp Phe Pro Asn Asn Met Pro Ile Ile Trp Glu Thr
    290                 295                 300
His Phe Gly Tyr Leu Thr Asp Leu Asn Tyr Thr Leu Val Ile Gly Glu
305                 310                 315                 320
Trp Gly Gly Asn Tyr Glu Gly Leu Asp Lys Val Trp Gln Asp Ala Phe
                325                 330                 335
Val Lys Trp Leu Ile Lys Lys Lys Ile Tyr Asn Phe Phe Tyr Trp Cys
            340                 345                 350
Leu Asn Pro Glu Ser Gly Asp Thr Gly Gly Ile Phe Leu Asp Asp Trp
        355                 360                 365
Lys Thr Val Asn Trp Glu Lys Met Arg Val Ile Tyr Arg Leu Ile Lys
    370                 375                 380
Ala Ala Asn Pro Glu Phe Glu Pro Leu Tyr Ile Ile Leu Lys Thr
385                 390                 395                 400
Asn Ala Thr Thr Ser Ile Leu Gly Val Gly Glu Arg Ile Arg Ile Tyr
                405                 410                 415
Trp Tyr Thr Asn Gly Lys Val Ile Asp Ser Asn Phe Ala His Ser Ser
            420                 425                 430
Glu Gly Glu Met Asn Ile Thr Val Thr Lys Ser Met Thr Leu Tyr Ile
        435                 440                 445
Ile Val Lys Lys Gly Asn Gln Thr Leu Arg Lys Glu Leu Lys Leu Tyr
    450                 455                 460
Val Ile Gly Gly Asn Tyr Gly Ser Asn Ile Ser Thr Thr Gln Leu Val
465                 470                 475                 480
Thr Pro Lys Lys Gly Gly Glu Arg Ile Ser Thr Ser Leu Lys Leu Ala
                485                 490                 495
Ile Ser Leu Leu Phe Ile Leu Leu Phe Val Trp Tyr Leu Leu Arg Glu
        500                 505                 510
Lys His

<210> SEQ ID NO 9
<211> LENGTH: 987
<212> TYPE: DNA
<213> ORGANISM: Thermotoga petrophila

<400> SEQUENCE: 9
atggaaacgc tcctccctgt agtcgtggtc cacgatattg agccagtttc aatgcgtctt      60
cagaggtaca agaacaaaaa ttcgataaaa agagaaaagc agggattaat accctgtttt     120
ttttattttt gggtgtattt agttctattt gcgaattttc agattttgaa tgtaaacatt     180
ttcataataa gatgttttct ggaggtgata atggtggtac tgatgacaaa accgggaaca     240
tcggattttg tatggaatgg cattcccctt ccatggagc tgaatctgtg aacataaag      300 gaatactccg ttctgtagc tatgaaattc gacggtgaaa aggtaacttt cgacgcggac      360
attcagaatc tttctccaaa agaaccagaa aggtacgttc tcggttatcc cgagttctat     420
tacggttata aaccctggga aaagcacacg gcagaaggtt cgaaacttcc agtacctgtt     480
tcctctatga atcatttttc cgtcgaagtt tctttcgata ttcaccacga accgtctctg     540
cctttgaact tgccatgga acatggctc acaagagaaa agtaccagac ggaagcgtcg      600
atcggcgatg ttgaaatcat ggtctggttc tatttcaaca atctcacacc agggggcaaa     660
aagatagagg agtttacgat tccgttcgtg ctgaacggag agagtgtcga aggcacctgg     720
gaactgtggc acgcggagtg gggatgggac tacctcgctt tccgcttgaa ggatcccgtg     780
```

```
aagaagggaa gggtgaagtt cgacgtgagg cattttcttg atgccgccgg gaaagctctt    840
tcgaattcca ctcgtgtgaa agattttgaa aatctttact tcaccgtctg ggaaattgga    900
accgagtttg gaagcccgga acaaagagc gcgcaattcg ggtggaagtt tgaaaacttc     960
tctattgatc tggaggtgag agaatga                                        987
```

<210> SEQ ID NO 10
<211> LENGTH: 328
<212> TYPE: PRT
<213> ORGANISM: Thermotoga petrophila

<400> SEQUENCE: 10

```
Met Glu Thr Leu Leu Pro Val Val Val His Asp Ile Glu Pro Val
1               5                   10                  15

Ser Met Arg Leu Gln Arg Tyr Lys Asn Lys Asn Ser Ile Lys Arg Glu
            20                  25                  30

Lys Gln Gly Leu Ile Pro Leu Phe Phe Tyr Phe Trp Val Tyr Leu Val
        35                  40                  45

Leu Phe Ala Asn Phe Gln Ile Leu Asn Val Asn Ile Phe Ile Ile Arg
    50                  55                  60

Cys Phe Leu Glu Val Ile Met Val Leu Met Thr Lys Pro Gly Thr
65                  70                  75                  80

Ser Asp Phe Val Trp Asn Gly Ile Pro Leu Ser Met Glu Leu Asn Leu
                85                  90                  95

Trp Asn Ile Lys Glu Tyr Ser Gly Ser Val Ala Met Lys Phe Asp Gly
            100                 105                 110

Glu Lys Val Thr Phe Asp Ala Asp Ile Gln Asn Leu Ser Pro Lys Glu
        115                 120                 125

Pro Glu Arg Tyr Val Leu Gly Tyr Pro Glu Phe Tyr Tyr Gly Tyr Lys
    130                 135                 140

Pro Trp Glu Lys His Thr Ala Glu Gly Ser Lys Leu Pro Val Pro Val
145                 150                 155                 160

Ser Ser Met Lys Ser Phe Ser Val Glu Val Ser Phe Asp Ile His His
                165                 170                 175

Glu Pro Ser Leu Pro Leu Asn Phe Ala Met Glu Thr Trp Leu Thr Arg
            180                 185                 190

Glu Lys Tyr Gln Thr Glu Ala Ser Ile Gly Asp Val Glu Ile Met Val
        195                 200                 205

Trp Phe Tyr Phe Asn Asn Leu Thr Pro Gly Gly Lys Lys Ile Glu Glu
    210                 215                 220

Phe Thr Ile Pro Phe Val Leu Asn Gly Glu Ser Val Glu Gly Thr Trp
225                 230                 235                 240

Glu Leu Trp His Ala Glu Trp Gly Trp Asp Tyr Leu Ala Phe Arg Leu
                245                 250                 255

Lys Asp Pro Val Lys Lys Gly Arg Val Lys Phe Asp Val Arg His Phe
            260                 265                 270

Leu Asp Ala Ala Gly Lys Ala Leu Ser Asn Ser Thr Arg Val Lys Asp
        275                 280                 285

Phe Glu Asn Leu Tyr Phe Thr Val Trp Glu Ile Gly Thr Glu Phe Gly
    290                 295                 300

Ser Pro Glu Thr Lys Ser Ala Gln Phe Gly Trp Lys Phe Glu Asn Phe
305                 310                 315                 320

Ser Ile Asp Leu Glu Val Arg Glu
                325
```

<210> SEQ ID NO 11
<211> LENGTH: 852
<212> TYPE: DNA
<213> ORGANISM: Caldivirga maquilingenesis

<400> SEQUENCE: 11

```
atgttgaaac ttattccact tgttaatggc aattataagt tgattcaatg ggagccactc      60
ggcggcgtgc acggagcaga tatcgagtgc atacatgtta ccccaaacgt atggaacata     120
gataaatcat cagttggcac tgtacagatc gaatatgagc cccaagttgg ctgtcttcgt     180
ttttcaattg atttcccgag gataagtata agacataatg taggcgtagc ggcatattca     240
gaagttattt acggacacaa gccgtggggc cccaccactt gcatggaccc tcagttcaag     300
ttccctatca aagtcaatga gtcaaaagga ctgtactcgt atgtaaatta taacgttaaa     360
tctaggtcac cagatgactc aatctttaat attgcttacg atctctggct tacaacgtcc     420
ccaaaccttaa caaacggacc ccagccagga gacgtagaag ttatgatctg gttgtactac     480
cacggacagc gccctgcagg cagactcatc ggggaactcc gcatgccgat tacattgggc     540
gatagtgagg cggcacgtga ctttgaagta tgggtggctg acacaggaat aggaatcggt     600
gaatgggcgg tagtgacctt cagaatcaag gacccaataa agggcggttt gataggagtt     660
aacctcataa actacatcga aagtgctttt aaaacgctcg aagaactcaa cccggtcaag     720
tggcggtacg gcgacctgct caacaaatat cttaatggaa ttgaattcgg cagtgagttt     780
ggtaatgtct cctcaggaat gataaaactt aattgggaac tctgcggcct gagccttgtg     840
aaagactctt ct                                                          852
```

<210> SEQ ID NO 12
<211> LENGTH: 284
<212> TYPE: PRT
<213> ORGANISM: Caldivirga maquilingenesis

<400> SEQUENCE: 12

```
Met Leu Lys Leu Ile Pro Leu Val Asn Gly Asn Tyr Lys Leu Ile Gln
  1               5                  10                  15

Trp Glu Pro Leu Gly Gly Val His Gly Ala Asp Ile Glu Cys Ile His
             20                  25                  30

Val Thr Pro Asn Val Trp Asn Ile Asp Lys Ser Ser Val Gly Thr Val
         35                  40                  45

Gln Ile Glu Tyr Glu Pro Gln Val Gly Cys Leu Arg Phe Ser Ile Asp
     50                  55                  60

Phe Pro Arg Ile Ser Ile Arg His Asn Val Gly Val Ala Ala Tyr Ser
 65                  70                  75                  80

Glu Val Ile Tyr Gly His Lys Pro Trp Gly Pro Thr Thr Cys Met Asp
                 85                  90                  95

Pro Gln Phe Lys Phe Pro Ile Lys Val Asn Glu Ser Lys Gly Leu Tyr
            100                 105                 110

Ser Tyr Val Asn Tyr Asn Val Lys Ser Arg Ser Pro Asp Asp Ser Ile
        115                 120                 125

Phe Asn Ile Ala Tyr Asp Leu Trp Leu Thr Thr Ser Pro Asn Leu Thr
    130                 135                 140

Asn Gly Pro Gln Pro Gly Asp Val Glu Val Met Ile Trp Leu Tyr Tyr
145                 150                 155                 160

His Gly Gln Arg Pro Ala Gly Arg Leu Ile Gly Glu Leu Arg Met Pro
                165                 170                 175
```

```
Ile Thr Leu Gly Asp Ser Glu Ala Ala Arg Asp Phe Glu Val Trp Val
            180                 185                 190

Ala Asp Thr Gly Ile Gly Ile Gly Glu Trp Ala Val Val Thr Phe Arg
        195                 200                 205

Ile Lys Asp Pro Ile Lys Gly Gly Leu Ile Gly Val Asn Leu Ile Asn
    210                 215                 220

Tyr Ile Glu Ser Ala Phe Lys Thr Leu Glu Glu Leu Asn Pro Val Lys
225                 230                 235                 240

Trp Arg Tyr Gly Asp Leu Leu Asn Lys Tyr Leu Asn Gly Ile Glu Phe
                245                 250                 255

Gly Ser Glu Phe Gly Asn Val Ser Ser Gly Met Ile Lys Leu Asn Trp
            260                 265                 270

Glu Leu Cys Gly Leu Ser Leu Val Lys Asp Ser Ser
        275                 280
```

<210> SEQ ID NO 13
<211> LENGTH: 2166
<212> TYPE: DNA
<213> ORGANISM: Thermotoga petrophila

<400> SEQUENCE: 13

| | |
|---|---:|
| atgatgggaa agatcgatga atcctttca cagctgacta ttgagaaaaa agtgaaactt | 60 |
| gtagtggggg ttggtcttcc aggactttt ggaaatccac attccagagt ggcaggtgca | 120 |
| gctggagaaa cgcatcctgt tccgaggctt ggaattcctt ctttcgttct ggccgacggt | 180 |
| cccgcgggcc tcagaataaa tcccacaaga gagaacgacg aaaacaccta ttacacaaca | 240 |
| gcgtttcctg ttgaaatcat gctcgcttcc acctggaaca aagatcttct ggaagaagta | 300 |
| ggaaaagcta tgggagaaga gtcagggaa tacggtgtcg atgtgcttct tgcacctgcg | 360 |
| atgaacattc acaggaaccc tctttgtgga ggaatttcg agtattattc agaagatcct | 420 |
| gtcctttccg gtgaaatggc ttcagccttt gtcaagggag ttcaatctca aggggtggga | 480 |
| gcctgcataa aacactttgt cgcgaacaac caggaaacga caggatggt agtggacacg | 540 |
| atcgtgtccg agcgagccct cagagaaata tatctgaaag gttttgaaat tgccgtcaag | 600 |
| aaagcaagac cctggaccgt gatgagcgct acaacaaac tgaatggaaa atactgttca | 660 |
| cagaacgaat ggcttttgaa gaaggttctc agggaagaat ggggatttga cggtttcgtg | 720 |
| atgagcgact ggtacgcggg agacaaccct gtagaacagc tcaaggccgg aaacgatatg | 780 |
| atcatgcctg aaaagcgta tcaggtgaac acggaaagaa gagatgaaat agaagaaatc | 840 |
| atggaggcgt tgaaggaggg aagactcagt gaggaagtcc tgaacgaatg tgtgagaaac | 900 |
| atcctcaaag ttcttgtgaa cgcgccttcc tttaagggt acaggtactc gaacaaaccg | 960 |
| gacctcgaat tcacgcgaa agttgcctac gaagcaggtg tggagggtgt tgtccttctt | 1020 |
| gagaacaacg gtgttcttcc attcgatgaa gtatccatg tcgccgtctt tggcaccggt | 1080 |
| caaatcgaaa caataaaggg aggaacggga agtggagaca cccatccgag atacacgatc | 1140 |
| tctatccttg aaggcataaa agaaagaaac atgaagttcg acgaagaact cacctccatc | 1200 |
| tatgaggatt acatcaaaaa gatgagagaa acagaggaat ataaacccag aactgactcc | 1260 |
| tggggaacgg ttataaaacc gaaacttcca gagaactttc tctcagaaaa agagataaag | 1320 |
| aaggctgcga agaaaaacga tgctgcagtt gttgtaatca gtaggatctc cggtgaggga | 1380 |
| tacgacagaa agccggtgaa aggtgacttc acctctccga tgacgagctg gagctcataa | 1440 |
| aaacagtctc aagggaattc cacgaacagg gtaagaaggt tgtggttctt ctcaacatcg | 1500 |

-continued

```
gaagtcccat tgaagttgca agctggagag atcttgtgga tggaatcctt ctcgtctggc    1560
aagcaggaca ggagatggga agaatagtgg ccgatgttct tgtgggaagg gtaaacccct    1620
ccggaaaact tccaacgacc ttcccgaagg attactcgga cgttccatcc tggacgttcc    1680
caggagagcc aaaggacaat ccgcaaagag tggtgtacga ggaagacatc tacgtgggat    1740
acaggtacta cgacaccttt ggtgtggaac ctgcctacga gttcggctac ggcctctctt    1800
acacaaagtt tgaatacaaa gatttaaaga tcgctatcga cggagatata ctcagagtgt    1860
cgtacacgat cacaaacacc ggggacagag ctggaaagga agtctcacag gtttatgtca    1920
aagctccaaa agggaaaata gacaaaccct tccaggagct gaaagcgttc cacaaaacaa    1980 aactttttgaa cccgggtgaa tccgaaaaga tctttctgga aattcctctt agagatcttg    2040
cgagtttcga tggaaagaa tggttgtcga gtcaggagaa tacgaggtca gggtcggtgc    2100
atcttcgagg gatataggtt gagagatatt tttctggttg agggagagaa gagattcaaa    2160
ccatga                                                               2166
```

<210> SEQ ID NO 14
<211> LENGTH: 722
<212> TYPE: PRT
<213> ORGANISM: Thermotoga petrophila

<400> SEQUENCE: 14

```
Met Met Gly Lys Ile Asp Glu Ile Leu Ser Gln Leu Thr Ile Glu Glu
1               5                   10                  15

Lys Val Lys Leu Val Gly Val Gly Leu Pro Gly Leu Phe Gly Asn
            20                  25                  30

Pro His Ser Arg Val Ala Gly Ala Gly Glu Thr His Pro Val Pro
        35                  40                  45

Arg Leu Gly Ile Pro Ser Phe Val Leu Ala Asp Gly Pro Ala Gly Leu
    50                  55                  60

Arg Ile Asn Pro Thr Arg Glu Asn Asp Glu Asn Thr Tyr Tyr Thr Thr
65                  70                  75                  80

Ala Phe Pro Val Glu Ile Met Leu Ala Ser Thr Trp Asn Lys Asp Leu
                85                  90                  95

Leu Glu Glu Val Gly Lys Ala Met Gly Glu Val Arg Glu Tyr Gly
            100                 105                 110

Val Asp Val Leu Leu Ala Pro Ala Met Asn Ile His Arg Asn Pro Leu
        115                 120                 125

Cys Gly Arg Asn Phe Glu Tyr Tyr Ser Glu Asp Pro Val Leu Ser Gly
    130                 135                 140

Glu Met Ala Ser Ala Phe Val Lys Gly Val Gln Ser Gln Gly Val Gly
145                 150                 155                 160

Ala Cys Ile Lys His Phe Val Ala Asn Asn Gln Glu Thr Asn Arg Met
                165                 170                 175

Val Val Asp Thr Ile Val Ser Glu Arg Ala Leu Arg Glu Ile Tyr Leu
            180                 185                 190

Lys Gly Phe Glu Ile Ala Val Lys Lys Ala Arg Pro Trp Thr Val Met
        195                 200                 205

Ser Ala Tyr Asn Lys Leu Asn Gly Lys Tyr Cys Ser Gln Asn Glu Trp
    210                 215                 220

Leu Leu Lys Lys Val Leu Arg Glu Glu Trp Gly Phe Asp Gly Phe Val
225                 230                 235                 240

Met Ser Asp Trp Tyr Ala Gly Asp Asn Pro Val Glu Gln Leu Lys Ala
                245                 250                 255
```

```
Gly Asn Asp Met Ile Met Pro Gly Lys Ala Tyr Gln Val Asn Thr Glu
            260                 265                 270

Arg Arg Asp Glu Ile Glu Glu Ile Met Glu Ala Leu Lys Glu Gly Arg
        275                 280                 285

Leu Ser Glu Glu Val Leu Asn Glu Cys Val Arg Asn Ile Leu Lys Val
290                 295                 300

Leu Val Asn Ala Pro Ser Phe Lys Gly Tyr Arg Tyr Ser Asn Lys Pro
305                 310                 315                 320

Asp Leu Glu Ser His Ala Lys Val Ala Tyr Glu Ala Gly Val Glu Gly
                325                 330                 335

Val Val Leu Leu Glu Asn Asn Gly Val Leu Pro Phe Asp Glu Ser Ile
            340                 345                 350

His Val Ala Val Phe Gly Thr Gly Gln Ile Glu Thr Ile Lys Gly Gly
        355                 360                 365

Thr Gly Ser Gly Asp Thr His Pro Arg Tyr Thr Ile Ser Ile Leu Glu
370                 375                 380

Gly Ile Lys Glu Arg Asn Met Lys Phe Asp Glu Glu Leu Thr Ser Ile
385                 390                 395                 400

Tyr Glu Asp Tyr Ile Lys Lys Met Arg Glu Thr Glu Glu Tyr Lys Pro
                405                 410                 415

Arg Thr Asp Ser Trp Gly Thr Val Ile Lys Pro Lys Leu Pro Glu Asn
            420                 425                 430

Phe Leu Ser Glu Lys Glu Ile Lys Lys Ala Lys Lys Asn Asp Ala
        435                 440                 445

Ala Val Val Ile Ser Arg Ile Ser Gly Glu Gly Tyr Asp Arg Lys
450                 455                 460

Pro Val Lys Gly Asp Phe Tyr Leu Ser Asp Asp Glu Leu Glu Leu Ile
465                 470                 475                 480

Lys Thr Val Ser Arg Glu Phe His Glu Gln Gly Lys Lys Val Val Val
                485                 490                 495

Leu Leu Asn Ile Gly Ser Pro Ile Glu Val Ala Ser Trp Arg Asp Leu
            500                 505                 510

Val Asp Gly Ile Leu Leu Val Trp Gln Ala Gly Gln Glu Met Gly Arg
        515                 520                 525

Ile Val Ala Asp Val Leu Val Gly Arg Val Asn Pro Ser Gly Lys Leu
530                 535                 540

Pro Thr Thr Phe Pro Lys Asp Tyr Ser Asp Val Pro Ser Trp Thr Phe
545                 550                 555                 560

Pro Gly Glu Pro Lys Asp Asn Pro Gln Arg Val Val Tyr Glu Glu Asp
                565                 570                 575

Ile Tyr Val Gly Tyr Arg Tyr Tyr Asp Thr Phe Gly Val Glu Pro Ala
            580                 585                 590

Tyr Glu Phe Gly Tyr Gly Leu Ser Tyr Thr Lys Phe Glu Tyr Lys Asp
        595                 600                 605

Leu Lys Ile Ala Ile Asp Gly Asp Ile Leu Arg Val Ser Tyr Thr Ile
610                 615                 620

Thr Asn Thr Gly Asp Arg Ala Gly Lys Glu Val Ser Gln Val Tyr Val
625                 630                 635                 640

Lys Ala Pro Lys Gly Lys Ile Asp Lys Pro Phe Gln Glu Leu Lys Ala
                645                 650                 655

Phe His Lys Thr Lys Leu Leu Asn Pro Gly Glu Ser Glu Lys Ile Phe
            660                 665                 670
```

Leu Glu Ile Pro Leu Arg Asp Leu Ala Ser Phe Asp Gly Lys Glu Trp
            675                 680                 685

Val Val Glu Ser Gly Glu Tyr Glu Val Arg Val Gly Ala Ser Ser Arg
        690                 695                 700

Asp Ile Arg Leu Arg Asp Ile Phe Leu Val Glu Gly Glu Lys Arg Phe
705                 710                 715                 720

Lys Pro

<210> SEQ ID NO 15
<211> LENGTH: 1341
<212> TYPE: DNA
<213> ORGANISM: Thermotoga petrophila

<400> SEQUENCE: 15

```
atgaacgtga aaaagttccc tgaaggattc ctctggggtg ttgcaacagc ttcctaccag      60
atcgagggtt ctcccctcgc agacggagct ggtatgtcta tctggcacac cttctcccat     120
actcctggaa atgtaaagaa cggtgacacg gagatgtgg cctgcgacca ctacaacaga      180
tggaaagagg acattgaaat catagagaaa ctcggagtaa aggcttacag attttcaatc     240
agctggccaa gaatacttcc ggaaggaaca ggaagggtga atcagaaagg actggatttt     300
tacaacagga tcatagacac cctgctggaa aaaggtatca cacccttgt gaccatctat      360
cactgggatc ttcccttcgc tcttcagttg aaaggaggat gggcgaacag agaaatagcg     420
gattggttcg cagaatactc aagggttctc tttgaaaatt cggcgaccg tgtgaagaac      480
tggatcacct gaacgaacc gtgggttgtt gccatagtgg gcatctgta cggagtccac      540
gctcctggaa tgagagatat ttacgtggct ttccgagctg ttcacaatct cttgagggca     600
cacgccaaag cggtgaaagt gttcaggaa actgtgaaag atggaaagat cggaatagtt      660
ttcaacaatg atatttcga acctgcgagt gaaaagagg aggacatcag agcggcgaga       720
ttcatgcatc agttcaacaa ctatcctctc tttctcaatc cgatctacag aggagattat     780
ccggagctcg ttctggaatt tgccagagag tatctaccgg agaattacaa agatgacatg     840
tccgagatac aggaaaagat cgactttgtt ggattgaact attaccggg tcatttggtg      900
aagttcgatc agatgcacc agctaaggtc tctttcgttg aaagggatct tccaaaaaca      960
gccatgggat gggagatcgt tccagaagga atctactgga tcctgaagaa ggtgaaagaa    1020
gaatacaacc caccagaggt ttacatcaca gagaatgggg ctgcttttga cgacgtagtt    1080
agtgaagatg aagagttca cgatcaaaac agaatcgatt atttgaaggc ccacattggt     1140
caggcatgga aggccataca ggagggagtg ccgcttaaag gttacttcgt ctggtcgctc    1200
ctcgacaatt cgaatgggc agagggatat tccaagagat tggtattgt gtacgtggac     1260
tacagtactc aaaaacgcat cataaaagac agtggttact ggtactcgaa cgtggtcaaa    1320
agcaacagtc tggaagattg a                                             1341
```

<210> SEQ ID NO 16
<211> LENGTH: 446
<212> TYPE: PRT
<213> ORGANISM: Thermotoga petrophila

<400> SEQUENCE: 16

Met Asn Val Lys Lys Phe Pro Glu Gly Phe Leu Trp Gly Val Ala Thr
1               5                   10                  15

Ala Ser Tyr Gln Ile Glu Gly Ser Pro Leu Ala Asp Gly Ala Gly Met
            20                  25                  30

```
Ser Ile Trp His Thr Phe Ser His Thr Pro Gly Asn Val Lys Asn Gly
         35                  40                  45

Asp Thr Gly Asp Val Ala Cys Asp His Tyr Asn Arg Trp Lys Glu Asp
 50                  55                  60

Ile Glu Ile Ile Glu Lys Leu Gly Val Lys Ala Tyr Arg Phe Ser Ile
 65                  70                  75                  80

Ser Trp Pro Arg Ile Leu Pro Glu Gly Thr Gly Arg Val Asn Gln Lys
                 85                  90                  95

Gly Leu Asp Phe Tyr Asn Arg Ile Ile Asp Thr Leu Leu Glu Lys Gly
            100                 105                 110

Ile Thr Pro Phe Val Thr Ile Tyr His Trp Asp Leu Pro Phe Ala Leu
        115                 120                 125

Gln Leu Lys Gly Gly Trp Ala Asn Arg Glu Ile Ala Asp Trp Phe Ala
    130                 135                 140

Glu Tyr Ser Arg Val Leu Phe Glu Asn Phe Gly Asp Arg Val Lys Asn
145                 150                 155                 160

Trp Ile Thr Leu Asn Glu Pro Trp Val Val Ala Ile Val Gly His Leu
                165                 170                 175

Tyr Gly Val His Ala Pro Gly Met Arg Asp Ile Tyr Val Ala Phe Arg
            180                 185                 190

Ala Val His Asn Leu Leu Arg Ala His Ala Lys Ala Val Lys Val Phe
        195                 200                 205

Arg Glu Thr Val Lys Asp Gly Lys Ile Gly Ile Val Phe Asn Asn Gly
    210                 215                 220

Tyr Phe Glu Pro Ala Ser Glu Lys Glu Glu Asp Ile Arg Ala Ala Arg
225                 230                 235                 240

Phe Met His Gln Phe Asn Asn Tyr Pro Leu Phe Leu Asn Pro Ile Tyr
                245                 250                 255

Arg Gly Asp Tyr Pro Glu Leu Val Leu Glu Phe Ala Arg Glu Tyr Leu
            260                 265                 270

Pro Glu Asn Tyr Lys Asp Asp Met Ser Glu Ile Gln Glu Lys Ile Asp
        275                 280                 285

Phe Val Gly Leu Asn Tyr Tyr Ser Gly His Leu Val Lys Phe Asp Pro
    290                 295                 300

Asp Ala Pro Ala Lys Val Ser Phe Val Glu Arg Asp Leu Pro Lys Thr
305                 310                 315                 320

Ala Met Gly Trp Glu Ile Val Pro Glu Gly Ile Tyr Trp Ile Leu Lys
                325                 330                 335

Lys Val Lys Glu Glu Tyr Asn Pro Pro Glu Val Tyr Ile Thr Glu Asn
            340                 345                 350

Gly Ala Ala Phe Asp Asp Val Val Ser Glu Asp Gly Arg Val His Asp
        355                 360                 365

Gln Asn Arg Ile Asp Tyr Leu Lys Ala His Ile Gly Gln Ala Trp Lys
    370                 375                 380

Ala Ile Gln Glu Gly Val Pro Leu Lys Gly Tyr Phe Val Trp Ser Leu
385                 390                 395                 400

Leu Asp Asn Phe Glu Trp Ala Glu Gly Tyr Ser Lys Arg Phe Gly Ile
                405                 410                 415

Val Tyr Val Asp Tyr Ser Thr Gln Lys Arg Ile Ile Lys Asp Ser Gly
            420                 425                 430

Tyr Trp Tyr Ser Asn Val Val Lys Ser Asn Ser Leu Glu Asp
        435                 440                 445
```

```
<210> SEQ ID NO 17
<211> LENGTH: 66
<212> TYPE: DNA
<213> ORGANISM: Artificial
<220> FEATURE:
<223> OTHER INFORMATION: synthetic sequence encoding fusion sequence
      with six histidines

<400> SEQUENCE: 17
gaacaaaaac tcatctcaga agaggatctg aatagcgccg tcgaccatca tcatcatcat      60
catcat                                                                66

<210> SEQ ID NO 18
<211> LENGTH: 21
<212> TYPE: PRT
<213> ORGANISM: Artificial
<220> FEATURE:
<223> OTHER INFORMATION: synthetic fusion sequence with six histidines

<400> SEQUENCE: 18

Glu Gln Lys Leu Ile Ser Glu Glu Asp Leu Asn Ser Ala Val Asp His
1               5                   10                  15

His His His His His
            20

<210> SEQ ID NO 19
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 19
atatccatgg agggaatac tattcttaaa atcgtactaa t                           41

<210> SEQ ID NO 20
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 20
atgctctaga aacctgggag cccttcttaa g                                     31

<210> SEQ ID NO 21
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 21
gaaacgctcc tccctgtagt                                                  20

<210> SEQ ID NO 22
<211> LENGTH: 38
<212> TYPE: DNA
<213> ORGANISM: Artificial
<220> FEATURE:
<223> OTHER INFORMATION: synthetic oligonucleotide primer

<400> SEQUENCE: 22
atgctctaga aattctctca cctccagatc aatagaga                              38
```

```
<210> SEQ ID NO 23
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 23
aggtgggtag ttcttctgat gg                                              22

<210> SEQ ID NO 24
<211> LENGTH: 41
<212> TYPE: DNA
<213> ORGANISM: Artificial
<220> FEATURE:
<223> OTHER INFORMATION: synthetic oligonucleotide primer

<400> SEQUENCE: 24
atgctctaga aattttacaa cttcgacgaa gaagtctttg a                         41

<210> SEQ ID NO 25
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 25
atatccatgg gaaagatcga tgaaatcctt tca                                  33

<210> SEQ ID NO 26
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 26
atgctctaga aatggtttga atctcttctc tccc                                 34

<210> SEQ ID NO 27
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 27
aacgtgaaaa agttccctga ag                                              22

<210> SEQ ID NO 28
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 28
atgctctaga aaatcttcca gactgttgct tttg                                 34

<210> SEQ ID NO 29
<211> LENGTH: 1230
<212> TYPE: DNA
<213> ORGANISM: Caldivirga maquilingensis

<400> SEQUENCE: 29
```

```
atggactact ctatcaactg ctctatcaac cctataaccc tcatggtcgc gcactcttct    60
cccctgaacc catctaacac actcgaactt acacttattc tcgaaaatgg catcaccacc   120
acagtaactg tcaccgcgac accacgcaac acttacccta tgatctccct ggctacatt   180
aatattaccc ctaacctctg gaaccttaac acagcttcgt catcaggata cgcctctatg   240
gtctacgatg catcacaggg tgctctttat attcatgtta atttcacaaa ggtttacctc   300
aatcagcaag ttggtgttgc cgcctactct gaattcatct atggctacaa accctggggc   360
acgctcacct ccgaggcagg cgggttcaat tttcctgtta agcttaccga actcggttct   420
cttctttcgt tcatcaatta ctcactcatt tcatattctc cacaagtcgc tatcttcgat   480
tgggcatacg acctttggct cacaacatcc ccaaatctca ccaacggccc tcaacccggc   540
gacgtcgagg tcatgatctg gctctattat cacctgcaac aacctgcggg ttttcccgtc   600
gctaacgtta cagtgccaat atgggtcaat ggctccctcg ttaacgaaac atttgaggtt   660
tggattggtt ctccacagat cgaacccggc acccacgcta tagtctcctt caggccaacg   720
aatccaatcc ctagaggcct cgtcggcgta aatgtcacga gttccttca  acttgccgtt   780
aactatctcg tgacactcta ccccctcatac tggaactaca catatctgga gagcaagtac   840
ttgaatggca tcgaattcgg atcagaatgg ggcaatccgt ctacatacaa tattacactc   900
aattgggtca tttataaagc ttatcttatc aaggtgcctc tggagtcaca gggcaccgtt   960
accgtcacat atactacaac tgttacatcc accatgactg ttacctcaat ccttgctacc  1020
acatccaccg tcaccactac atctacactt acatctaccg ttaccgccac ttcagttcct  1080
acttccaccg tcacgcagac tctcactacc tccatcgtca aaccgtcat  ccctgtctac  1140
tatactgcca ccataatcgt ccttcttata atcatcgcag tcgtcattgc acttgcgttc  1200
gcccgccgcg gcatccgggt tcgtctctgt                                  1230
```

<210> SEQ ID NO 30
<211> LENGTH: 410
<212> TYPE: PRT
<213> ORGANISM: Caldivirga maquilingensis

<400> SEQUENCE: 30

Met Asp Tyr Ser Ile Asn Cys Ser Ile Asn Pro Ile Thr Leu Met Val
1               5                   10                  15

Ala His Ser Ser Pro Leu Asn Pro Ser Asn Thr Leu Glu Leu Thr Leu
            20                  25                  30

Ile Leu Glu Asn Gly Ile Thr Thr Thr Val Thr Val Thr Ala Thr Pro
        35                  40                  45

Arg Asn Thr Tyr Pro Met Ile Ser Leu Gly Tyr Ile Asn Ile Thr Pro
    50                  55                  60

Asn Leu Trp Asn Leu Asn Thr Ala Ser Ser Ser Gly Tyr Ala Ser Met
65                  70                  75                  80

Val Tyr Asp Ala Ser Gln Gly Ala Leu Tyr Ile His Val Asn Phe Thr
                85                  90                  95

Lys Val Tyr Leu Asn Gln Gln Val Gly Val Ala Ala Tyr Ser Glu Phe
            100                 105                 110

Ile Tyr Gly Tyr Lys Pro Trp Gly Thr Leu Thr Ser Glu Ala Gly Gly
        115                 120                 125

Phe Asn Phe Pro Val Lys Leu Thr Glu Leu Gly Ser Leu Leu Ser Phe
    130                 135                 140

Ile Asn Tyr Ser Leu Ile Ser Tyr Ser Pro Gln Val Ala Ile Phe Asp
145                 150                 155                 160

```
Trp Ala Tyr Asp Leu Trp Leu Thr Thr Ser Pro Asn Leu Thr Asn Gly
                165                 170                 175

Pro Gln Pro Gly Asp Val Glu Val Met Ile Trp Leu Tyr Tyr His Leu
            180                 185                 190

Gln Gln Pro Ala Gly Phe Pro Val Ala Asn Val Thr Val Pro Ile Trp
        195                 200                 205

Val Asn Gly Ser Leu Val Asn Glu Thr Phe Glu Val Trp Ile Gly Ser
    210                 215                 220

Pro Gln Ile Glu Pro Gly Thr His Ala Ile Val Ser Phe Arg Pro Thr
225                 230                 235                 240

Asn Pro Ile Pro Arg Gly Leu Val Gly Val Asn Val Thr Lys Phe Leu
                245                 250                 255

Gln Leu Ala Val Asn Tyr Leu Val Thr Leu Tyr Pro Ser Tyr Trp Asn
            260                 265                 270

Tyr Thr Tyr Leu Glu Ser Lys Tyr Leu Asn Gly Ile Glu Phe Gly Ser
        275                 280                 285

Glu Trp Gly Asn Pro Ser Thr Tyr Asn Ile Thr Leu Asn Trp Val Ile
    290                 295                 300

Tyr Lys Ala Tyr Leu Ile Lys Val Pro Leu Glu Ser Gln Gly Thr Val
305                 310                 315                 320

Thr Val Thr Tyr Thr Thr Thr Val Thr Ser Thr Met Thr Val Thr Ser
                325                 330                 335

Ile Leu Ala Thr Thr Ser Thr Val Thr Thr Thr Ser Thr Leu Thr Ser
            340                 345                 350

Thr Val Thr Ala Thr Ser Val Ser Thr Ser Thr Val Thr Gln Thr Leu
        355                 360                 365

Thr Thr Ser Ile Val Lys Thr Val Ile Pro Val Tyr Tyr Thr Ala Thr
    370                 375                 380

Ile Ile Val Leu Leu Ile Ile Ile Ala Val Val Ile Ala Leu Ala Phe
385                 390                 395                 400

Ala Arg Arg Gly Ile Arg Val Arg Leu Cys
                405                 410

<210> SEQ ID NO 31
<211> LENGTH: 2214
<212> TYPE: DNA
<213> ORGANISM: Pyrococcus horikoshii

<400> SEQUENCE: 31
atgagatttc aattcggatt ctccaaagaa gatgaacagg tgctgggcac aatactaaca      60
ctcggaaatg gacaattagg agttagggga gaatttgaac tcgagagatc tccttatgga     120
acgatcgtta gcggggtcta tgattacact ccctacttct acagggaatt ggtaaatggt     180
cccaggacta tagggatgat aataattata gatggagaac taataaatcc aagctctcaa     240
aaagtcaagg aattccagag agagctcgat atagaaaaag cttattaag aactcactta     300 gagattgaaa caaaaatgg aaataaaatt ttatataaaa gtacaaggat agtccacatg     360
aaaagaaaaa acctaatcct tctagatttt gagctaaaag ctagcaaggg aggaatcgca     420
gttgtagtta atcccataga attcaatact gcaaatccag ggtttataga cgagataatg     480
atcaagcatt atagagtgga ctcgataaaa gagactgagg agggagtata cgctagggtg     540
aaaactttag acaataagta cacgttggaa attgcaagta gcttggttcc atcagaaatt     600
acatcgagga gcacctttag aaccgataat gaaattggag aaatttacat tgttaaactt     660
```

-continued

```
aaaccaggaa aaacgtacaa atttacaaag tacgttacag tatctaaagg agcagcttta    720
gaggagttaa aagatgttaa gagattagga tttgaaaagc tatatgaaga gcatataaac    780
agctggaaga gaatatggga gaaagtgaaa gtggaaatcg aaggagataa agaccttgaa    840
aatgccctaa actttaacat ttttcacttg atccaatccc ttccaccaac agataaagtc    900
tcgctaccag caagggggaat acatgggttt gggtataggg gacatatatt ctgggataca    960
gagatatatg cattaccttt cttcatattc acgatgccaa agaggccag agattgctc    1020
ctctatagat gcaacaactt agatgccgct aaagaaaatg caaagatgaa tggatatcaa   1080
ggggtccaat ttccctggga gtcggcagat gatggacgcg aggctacccc ctctgagata   1140
ccattggata tgttgggaag gaaaatcgtt agaatttaca ccggagagga ggaacatcac   1200
ataactgcgg atatagcata tatagttgat ttttattacc aagtctctgg agatctcgaa   1260
tttatgaaca ggtgtggcct tgagataatc tttgagacgg cccgattttg ggctagtagg   1320
gttgagttcg aggaaggaaa agggtacgtc attaaaaaag taataggacc tgatgaatac   1380
catgagcacg ttaacaacaa cttctttaca aacttaatgg ccaagcataa tctcgaactt   1440
gcaataagat actttagaga gtcaaagaat agggaaccgt ggaaaaagat tgtcgaaaaa   1500
ttaaacataa gagaggagga ggttgaaaaa tgggaagaga tagctaaaaa catgtacatt   1560
cccaggaaga tagacggagt ttttgaagag tttgatggtt actttgaatt gatggatttt   1620
gaagttgatc ccttcaatat tggagaaaaa acactccccg aggaaatcag gaataacata   1680
gggaaaacga aactcgttaa gcaggccgat gtcatcatgg cccaatatct ccttaaggac   1740
tacttctctc cagaggaaat aaagagtaac tttaactatt atataaggag aactacccat   1800
gcttcatcac tctccatgcc cccatacgcg atcattgcaa cctggatagg ggaggtaaag   1860
atagcatatg agtacttcaa gagatgtgca aatatagatc tcaaaaacgt gtacggaaac   1920
actgcagagg gatttcactt agcaacggcg ggaggaacct ggcaagtact cgtcagagga   1980
ttttgtggcc tcaatgtaaa aggaaacaaa atagagctta atcctaatct tcctgaaaaa   2040
tggaagtacg ttaagttcag gatattcttc aaaggttcat ggatagaatt taaaatttct   2100
aggaagaaag ttagggctag aatgcttgaa ggatcgagaa aagtcaaaat atctagcttt   2160
ggaaaggaag tagatctata tcctggaaaa gaggttgtaa tagtagctaa ttaa          2214
```

<210> SEQ ID NO 32
<211> LENGTH: 737
<212> TYPE: PRT
<213> ORGANISM: Pyrococcus horikoshii

<400> SEQUENCE: 32

```
Met Arg Phe Gln Phe Gly Phe Ser Lys Glu Asp Glu Gln Val Leu Gly
1               5                   10                  15

Thr Ile Leu Thr Leu Gly Asn Gly Gln Leu Gly Val Arg Gly Glu Phe
            20                  25                  30

Glu Leu Glu Arg Ser Pro Tyr Gly Thr Ile Val Ser Gly Val Tyr Asp
        35                  40                  45

Tyr Thr Pro Tyr Phe Tyr Arg Glu Leu Val Asn Gly Pro Arg Thr Ile
    50                  55                  60

Gly Met Ile Ile Ile Ile Asp Gly Glu Leu Ile Asn Pro Ser Ser Gln
65                  70                  75                  80

Lys Val Lys Glu Phe Gln Arg Glu Leu Asp Ile Glu Lys Gly Leu Leu
                85                  90                  95

Arg Thr His Leu Glu Ile Glu Thr Lys Asn Gly Asn Lys Ile Leu Tyr
```

```
                  100                 105                 110
        Lys Ser Thr Arg Ile Val His Met Lys Arg Lys Asn Leu Ile Leu Leu
                    115                 120                 125

Asp Phe Glu Leu Lys Ala Ser Lys Gly Gly Ile Ala Val Val Val Asn
                    130                 135                 140

Pro Ile Glu Phe Asn Thr Ala Asn Pro Gly Phe Ile Asp Glu Ile Met
        145                 150                 155                 160

Ile Lys His Tyr Arg Val Asp Ser Ile Lys Glu Thr Glu Glu Gly Val
                            165                 170                 175

Tyr Ala Arg Val Lys Thr Leu Asp Asn Lys Tyr Thr Leu Glu Ile Ala
                        180                 185                 190

Ser Ser Leu Val Pro Ser Glu Tyr Thr Ser Arg Ser Thr Phe Arg Thr
                    195                 200                 205

Asp Asn Glu Ile Gly Glu Ile Tyr Ile Val Lys Leu Lys Pro Gly Lys
                    210                 215                 220

Thr Tyr Lys Phe Thr Lys Tyr Val Thr Val Ser Lys Gly Ala Ala Leu
        225                 230                 235                 240

Glu Glu Leu Lys Asp Val Lys Arg Leu Gly Phe Glu Lys Leu Tyr Glu
                        245                 250                 255

Glu His Ile Asn Ser Trp Lys Arg Ile Trp Glu Lys Val Lys Val Glu
                        260                 265                 270

Ile Glu Gly Asp Lys Asp Leu Glu Asn Ala Leu Asn Phe Asn Ile Phe
                    275                 280                 285

His Leu Ile Gln Ser Leu Pro Pro Thr Asp Lys Val Ser Leu Pro Ala
                    290                 295                 300

Arg Gly Ile His Gly Phe Gly Tyr Arg Gly His Ile Phe Trp Asp Thr
        305                 310                 315                 320

Glu Ile Tyr Ala Leu Pro Phe Phe Ile Phe Thr Met Pro Lys Glu Ala
                        325                 330                 335

Arg Arg Leu Leu Leu Tyr Arg Cys Asn Asn Leu Asp Ala Ala Lys Glu
                        340                 345                 350

Asn Ala Lys Met Asn Gly Tyr Gln Gly Val Gln Phe Pro Trp Glu Ser
                    355                 360                 365

Ala Asp Asp Gly Arg Glu Ala Thr Pro Ser Glu Ile Pro Leu Asp Met
                    370                 375                 380

Leu Gly Arg Lys Ile Val Arg Ile Tyr Thr Gly Glu Glu Glu His His
        385                 390                 395                 400

Ile Thr Ala Asp Ile Ala Tyr Ile Val Asp Phe Tyr Gln Val Ser
                        405                 410                 415

Gly Asp Leu Glu Phe Met Asn Arg Cys Gly Leu Glu Ile Ile Phe Glu
                        420                 425                 430

Thr Ala Arg Phe Trp Ala Ser Arg Val Glu Phe Glu Glu Gly Lys Gly
                    435                 440                 445

Tyr Val Ile Lys Lys Val Ile Gly Pro Asp Glu Tyr His Glu His Val
                    450                 455                 460

Asn Asn Asn Phe Phe Thr Asn Leu Met Ala Lys His Asn Leu Glu Leu
        465                 470                 475                 480

Ala Ile Arg Tyr Phe Arg Glu Ser Lys Asn Arg Glu Pro Trp Lys Lys
                        485                 490                 495

Ile Val Glu Lys Leu Asn Ile Arg Glu Glu Val Glu Lys Trp Glu
                    500                 505                 510

Glu Ile Ala Lys Asn Met Tyr Ile Pro Arg Lys Ile Asp Gly Val Phe
                    515                 520                 525
```

```
Glu Glu Phe Asp Gly Tyr Phe Glu Leu Met Asp Phe Glu Val Asp Pro
        530                 535                 540

Phe Asn Ile Gly Glu Lys Thr Leu Pro Glu Glu Ile Arg Asn Asn Ile
545                 550                 555                 560

Gly Lys Thr Lys Leu Val Lys Gln Ala Asp Val Ile Met Ala Gln Tyr
                565                 570                 575

Leu Leu Lys Asp Tyr Phe Ser Pro Glu Glu Ile Lys Ser Asn Phe Asn
                580                 585                 590

Tyr Tyr Ile Arg Arg Thr Thr His Ala Ser Ser Leu Ser Met Pro Pro
            595                 600                 605

Tyr Ala Ile Ile Ala Thr Trp Ile Gly Glu Val Lys Ile Ala Tyr Glu
        610                 615                 620

Tyr Phe Lys Arg Cys Ala Asn Ile Asp Leu Lys Asn Val Tyr Gly Asn
625                 630                 635                 640

Thr Ala Glu Gly Phe His Leu Ala Thr Ala Gly Gly Thr Trp Gln Val
                645                 650                 655

Leu Val Arg Gly Phe Cys Gly Leu Asn Val Lys Gly Asn Lys Ile Glu
                660                 665                 670

Leu Asn Pro Asn Leu Pro Glu Lys Trp Lys Tyr Val Lys Phe Arg Ile
            675                 680                 685

Phe Phe Lys Gly Ser Trp Ile Glu Phe Lys Ile Ser Arg Lys Lys Val
        690                 695                 700

Arg Ala Arg Met Leu Glu Gly Ser Arg Lys Val Lys Ile Ser Ser Phe
705                 710                 715                 720

Gly Lys Glu Val Asp Leu Tyr Pro Gly Lys Glu Val Val Ile Val Ala
                725                 730                 735

Asn
```

THERMOCELLULASES FOR LIGNOCELLULOSIC DEGRADATION

BACKGROUND OF THE INVENTION

1. Field of the Invention

This invention generally relates to thermostable enzymes capable of degrading (hydrolyzing) cellulose at high temperatures, and the incorporation of nucleic acids coding for one or more of such enzymes into a host, and, more particularly, a host that produces or is composed of cellulosic material.

2. Background of the Invention

Cellulose is a polysaccharide consisting of a linear chain of several hundred to over nine thousand β (1→4) linked D-glucose units [formula $(C_6H_{10}O_5)n$]. Cellulose is the most abundant organic compound on earth, making up about 33 percent of all plant matter, about 50 percent of wood, and about 90 percent of products such as cotton. In nature, cellulose is present as part of the lignocellulosic biomass of plants, which is composed of cellulose, hemicellulose, and lignin. The carbohydrate polymers (cellulose and hemicelluloses) are tightly bound to the lignin, by hydrogen and covalent bonds.

Many highly desirable products are derived from lignocellulosic biomass. In particular, much interest has recently been focused on recapturing the saccharide building blocks locked in plant biomass for biofuel production. For example, fermentation of plant biomass to ethanol is an attractive carbon neutral energy option since the combustion of ethanol from biomass produces no net carbon dioxide in the earth's atmosphere. Further, biomass is readily available, and its fermentation provides an attractive way to dispose of many industrial and agricultural waste products. Finally, plant biomass is a highly renewable resource. Many dedicated energy crops can provide high energy biomass, which may be harvested multiple times each year.

One barrier to the production of products from biomass is that the cellulosic polymer has evolved to resist degradation and to confer hydrolytic stability and structural robustness to the cell walls of plants. This robustness or "recalcitrance" is due largely to extensive intermolecular hydrogen bonding between cellulose polymer chains. Some organisms, notably fungi, bacteria, and protozoans, but also some plants and animals, have evolved the ability to digest cellulose. In vivo cellulose breakdown typically entails the cooperative interaction of several cellulases, enzymes that catalyze the cellulolysis (hydrolysis) of cellulose. Several different kinds of cellulases, which differ structurally and mechanistically, are known, and some of these have been isolated, characterized and used to break down cellulose in vitro. General categories of cellulases include: endo-cellulases (endoglucanases), which randomly hydrolyze internal bonds to disrupt the crystalline structure of cellulose, thereby exposing individual cellulose polysaccharide chains; and exo-cellulases (exo-processive-endoglucanases), which cleave 2-4 units from the ends of the exposed chains produced by endocellulases to produce tetrasaccharides or disaccharides such as cellobiose. Two major types of exo-cellulases are known, one of which works processively from the reducing end, and one of which works processively from the non-reducing end of cellulose. A third major type of cellulase is cellobiase or beta-glucosidase, which hydrolyses exo-cellulase products such as cellobiose into individual glucose monosaccharides.

Typically, the digestion of cellulose is carried out at temperatures approaching 100° C. because, at high temperatures, intermolecular hydrogen bonds are disrupted and recalcitrant cellulose polymers become accessible to the cellulase enzymes. Therefore, cellulases used commercially in such processes must be able to withstand very high temperatures, preferably for extended periods of time.

There is an ongoing need to identify, isolate and characterize cellulases, especially thermally stable cellulases, for use in the enzymatic hydrolysis of cellulose. Of particular interest is the development of groups or systems of cellulases that include enzymes with endo-cellulase, exo-cellulase and beta-glucosidase activity, the enzymes in the system acting in concert to carry out the complete hydrolysis of cellulose to glucose at high temperatures.

SUMMARY OF THE INVENTION

Protein sequences which heretofore were not recognized as having enzymatic activity have been isolated and characterized as thermostable enzymes capable of degrading (hydrolyzing) cellulose at high temperatures. The activity is referred to herein as cellulase or cellulase-like. The enzymes, originating from Archaea and various thermophilic bacteria, include: endoglucanases that randomly hydrolyze internal glycosidic bonds; exo-processive-endoglucanases that split off cellobiose dimers; and β-glucosidases that reduce cellobiose into monomeric glucose molecules. While the β-glucosidase enzymes are technically not "cellulases" because cellobiose (not cellulose) is the substrate they cleave, the three groups of enzymes may be sometimes collectively referred to as "cellulases" herein. The enzymes are optimally catalytically active at temperatures at or above about 85° C. and retain >85% of their enzymatic activity even after a 5 day incubation at elevated temperature, e.g. 90° C. In some embodiments, the enzymes, or enzyme systems or groupings comprising multiple thermostable catalytic activities may advantageously be used to degrade cellulose. Preferably, in the case of systems which have multiple thermostable catalytic activities, such a system comprises at least one endoglucanase, at least one exo processive-endoglucanase, and at least one beta-glucosidase enzyme, and thus can carry out the complete hydrolysis of cellulose to glucose at high temperatures in a sequential, cooperative manner. Catalytic consolidation at high-temperatures using the enzyme systems described herein is not additive but synergistic, accessing recalcitrant cellulose and hydrolyzing beta linkages at temperatures above 85° C. Thus, one aspect of the invention is to employ the enzymes, alone or in a group, in processes to break down cellulosic material by contacting the cellulosic material with the enzymes and elevating the temperature to activate the enzymes to break down the cellulosic material. These processes might be performed, for example, in tanks where the cellulosic material is distributed in a liquid carrier; however, the enzymatic breakdown may be achieved simply through elevating the temperature of the cellulosic material with the enzymes being in contact with the cellulosic material.

The invention also contemplates the incorporation of nucleic acids coding for one or more of the enzymes into a host (e.g., a plant, fungi, bacterium or animal). In the case where the host produces or is composed of cellulosic material (e.g., plants such as corn, switch grass, sugar cane, sorghum, pinus and eucalyptus), the host can be subjected to breakdown of the cellulosic material, for example, after harvest. That is, in a particular example, corn or switchgass transformed to include nucleic acids coding for the enzymes will express the enzymes internally, and after collection or harvest of the corn or switchgrass, the enzymes can be activated to begin and preferably ultimately to completely degrade the cellulose simply by elevating the temperature of the corn or switchgrass.

BRIEF DESCRIPTION OF THE DRAWINGS

FIG. 1A-B. *Pyrococcus furiosus* Termocel 1 endoglucanase. A, nucleotide sequence (903 bp, SEQ ID NO: 1); and B, amino acid sequence (301 aa, SEQ ID NO: 2). Nucleotide sequence is optimized for expression in corn and shown without N-terminal signal peptide encoding sequence.

FIG. 2A-B. *Thermotoga petrophila* Termocel 2 endoglucanase. A, nucleotide sequence (825 bp, SEQ ID NO: 3); and B, amino acid sequence (274 aa, SEQ ID NO: 4).

FIG. 3A-B. *Pyrococcus horikoshii* Termocel 3 exocellulase. A, nucleotide sequence (1377 bp, SEQ ID NO: 5); and B, amino acid sequence (458 aa, SEQ ID NO: 6).

FIG. 4A-B. *Pyrococcus abyssi* Termocel 4 exocellulase. A, nucleotide sequence (1542 bp, SEQ ID NO: 7); and B, amino acid sequence (514 aa, SEQ ID NO: 8). Nucleotide sequence is optimized for expression in rice and shown without stop codon.

FIG. 5A-B. *Thermotoga petrophila* Termocel 5 endoglucanase. A, nucleotide sequence (987 bp, SEQ ID NO: 9); and B, amino acid sequence (328 aa, SEQ ID NO: 10).

FIG. 6A-B. *Caldivirga maquilingenesis* Termocel 6 endoglucanase. A, nucleotide sequence (852 bp, SEQ ID NO: 11); and B, amino acid sequence (284 aa, SEQ ID NO: 12). Nucleotide sequence is optimized for expression in corn.

FIG. 7A-B. *Thermotoga petrophila* Termocel 7 beta-glucosidase. A, nucleotide sequence (2169 bp, SEQ ID NO: 13); and B, amino acid sequence (722 aa, SEQ ID NO: 14).

FIG. 8A-B. *Thermotoga petrophila* Termocel 8 beta-glucosidase. A, nucleotide sequence (1341 bp, SEQ ID NO: 15); and B, amino acid sequence (446 aa, SEQ ID NO: 16).

FIG. 9. Characteristics of high-temperature operating thermo-stable cellulases. swAvicel=phosphoric acid swollen Avicel; $_{av}$Cellulose=Avicel; cellulase specific activity is expressed as of reducing sugar/mg protein/day at 85° C., pH 6; beta-glucosidase specific activity is expressed as nM p-nitrophenol (pN)/µg protein/minute.

FIG. 10A-E. Processive exocellulases (cellobiohydrolase). Capillary zone electrophoresis (CZE) of 8-aminonaphthalene-1,3,6 trisulfonic acid (ANTS)-labeled cellopentose breakdown products incubated with Termocel 1 (A), Termocel 2 (B) and Termocel 3 (C). CZE retention times (D) of purified monomer, (DPI) dimer (DP2), trimer (DP3) and the substrate cellopentose (DP5). Sequential predicted cleavage pattern (E) between DP5 and DP4, DP4 and DP3, DP3 and DP2. Assay conditions, Substrate, ANTS-cellopentose (FIG. 9C), buffer sodium phosphate/citrate 50 mM, incubated at 95° C., pH 6.

FIG. 11A-E. Processive endocellulases (endoglucanase). Capillary zone electrophoresis (CZE) of ANTS-labeled cellopentose breakdown products incubated with Termocel 4 (A), Termocel 5 (B) and Termocel 6 (C). CZE retention times (D) of purified monomer, (DPI) dimer (DP2), trimer (DP3) and the substrate cellopentose (DP5). Predicted cleavage pattern (E) between DP2 ad DP3 and DP3 and DP4. Assay conditions, Substrate, ANTS-cellopentose (FIG. 9C), buffer sodium phosphate 50 mM, incubated at 95° C., pH 6.

FIG. 12. Temperature optima for high-temperature catalytic cellulases, and activities at 60, 45 and 20° C. $_{sw}$Avicel=phosphoric acid swollen Avicel; $_{av}$Cellulose=Avicel; cellulase specific activity is expressed as µM of reducing sugar/mg protein/day at 85° C., pH 6; beta-glucosidase specific activity is expressed as nM p-nitrophenol (pN)/µg protein/minute.

FIG. 13A-D. Termocel thermostability. Termocels were incubated at 90° C. in phosphate/citrate buffer for the indicated number of hours and CMC or PNPG activity determined. The amount of residual activity is shown. A, Termocels 1 and 2; B, Termocels 3 and 4; C, Termocels 5 and 6; D, Termocels 7 and 8 With the exception of Termocel 3, all cellulases retained >80% of activity after 120 hrs at 90° C. Thus, these enzymes are stable at high temperatures.

FIG. 15. Table depicting biomass substrate specificity of particular Termocels.

FIG. 16A-B. *Caldivirga maquilingensis* Termocel 9 endoglucanase. A, nucleotide sequence (1230 bp, SEQ ID NO: 29); and B, amino acid sequence (410 aa, SEQ ID NO: 30). Nucleotide sequence is optimized for expression in corn.

FIG. 17A-B. *Pyrococcus horikoshii* Termocel 10 endoglucanase. A, nucleotide sequence (2214 bp, SEQ ID NO: 31); and B, amino acid sequence (737 aa, SEQ ID NO: 32).

FIG. 18A-F. Nucleotide sequences as set forth in SEQ ID NO: 1 (from *Pyrococcus furiosus*), SEQ ID NO: 3 (from *Thermotoga petrophila*), SEQ ID NO: 5 (from *Pyrococcus horikoshii*), SEQ ID NO: 7 (from *Pyrococcus abyssi*), SEQ ID NO: 9 (from *Thermotoga petrophila*), SEQ ID NO: 11 (from *Caldivirga maquilingensis*), SEQ ID NO: 29 (from *Caldivirga maquilingensis*), SEQ ID NO: 31 (from *Pyrococcus horikoshii*), SEQ ID NO: 13 (from *Thermotoga petrophila*), and SEQ ID NO: 15 (from *Thermotoga petrophila*).

FIG. 19A-C. Amino acid sequences as set forth in SEQ ID NO: 2 (from *Pyrococcus furiosus*), SEQ ID NO: 4 (from *Thermotoga petrophila*), SEQ ID NO: 6 (from *Pyrococcus horikoshii*), SEQ ID NO: 8 (from *Pyrococcus abyssi*), SEQ ID NO: 10 (from *Thermotoga petrophila*), SEQ ID NO: 12 (from *Caldivirga maquilingenesis*), SEQ ID NO: 30 (from *Caldivirga maquilingensis*), SEQ ID NO: 32 (from *Pyrococcus horikoshii*), SEQ ID NO: 14 (from *Thermotoga petrophila*), and SEQ ID NO: 16 (from *Thermotoga petrophila*).

DETAILED DESCRIPTION

Figure 14:
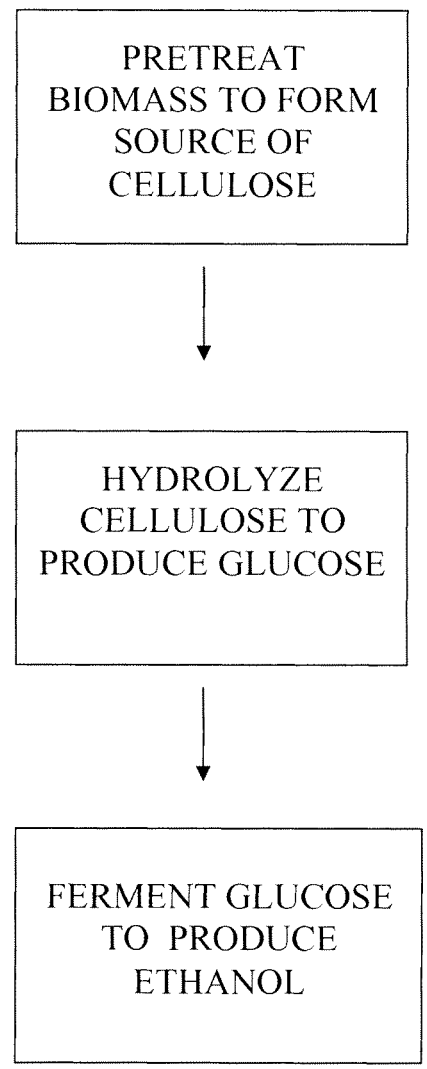
FIG. 14. Flow chart illustrating cellulose treatment steps.

The present invention is based on the identification and characterization of a comprehensive set of thermostable cellulases that work in concert to catalyze the hydrolysis of cellulose to glucose at very high temperatures. The cellulases, originally identified in archeal and bacterial genomes, include endoglucanases that randomly cleave internal glycosidic bonds; exo-processive-endoglucanases that further hydrolyze cellulose fragments into cellobiose dimers; and β-glucosidases that further hydrolyze cellobiose dimers to glucose monomers. While the enzymes may be used individually, in some embodiments of the invention they are grouped to form a cooperative enzyme system. By combining into a group at least one endoglucanase, at least one exo-processive-endoglucanase and at least one β-glucosidase, an enzyme system is formed that is capable of the complete breakdown of cellulose to glucose. Importantly, the enzyme system's various catalytic activities are optimal at temperatures that are high enough to destabilize the hydrogen bonds between crystalline cellulose strands (e.g. at temperatures greater than 80° C.). Destabilization of hydrogen bonds at high temperatures causes disruption of the crystalline structure of cellulose, thereby facilitating access by the first enzyme in the series (endoglucanase) to internal glycosidic bonds of individual cellulose polymer strands, and allowing the step-wise process of cellulose breakdown to begin.

Exemplary amino acid sequences of the recombinant enzymes of the invention and exemplary nucleotide sequences that encode them are depicted in FIGS. 1-8. However, those of skill in the art will recognize that the invention also encompasses variant proteins comprising amino acid sequences that are based on or derived from the sequences disclosed herein. By an amino acid sequence that is "derived from" or "based on" the sequence disclosed herein, we mean that a derived sequence (or variant sequence) displays at least about 50 to 100% identity to an amino acid sequence disclosed herein, or about 60 to 100% identify, or about 70 to 100% identity, or even from about 80 to 100% identify. In preferred embodiments, a variant sequence displays from about 90 to 100% or about 95 to 100% amino acid identity. In further preferred embodiments, a variant sequence is 95, 96, 97, 98 or 99% identical to at least one sequence disclosed herein. Variations in the sequences may be due to a number of factors and may include, for example: conservative or non-conservative amino acid substitutions; natural variations among different populations as isolated from natural sources; various deletions or insertions (which may be amino terminal, carboxyl terminal, or internal); addition of leader sequences to promote secretion from the cell; addition of targeting sequences to direct the intracellular destination of a polypeptide; etc. Such alterations may be naturally occurring or may be intentionally introduced (e.g. via genetic engineering) for any of a wide variety of reasons, e.g. in order to eliminate or introduce protease cleavage sites, to eliminate or introduce glycosylation sites, in order to improve solubility of the polypeptide, to facilitate polypeptide isolation (e.g. introduction of a histidine or other tag), as a result of a purposeful change in the nucleic acid sequence (see discussion of the nucleic acid sequence below) which results in a non-silent change in one or more codons and thus the translated amino acid, in order to improve thermal stability of the protein, etc. All such variant sequences are encompassed by the present invention, so long as the resulting polypeptide is capable of catalyzing the enzyme activity of the original protein as disclosed herein. For example, the invention includes shorter portions of the sequences that also retain the catalytic activity of the enzyme. The full-length protein sequences and/or active portions thereof are both referred to as polypeptides herein. In addition, the invention also includes chimeric or fusion proteins that include, for example: more than one of the enzymes disclosed herein (or active portions thereof); or one or more of the enzymes disclosed herein (or portions thereof) plus some other useful protein or peptide sequence(s), e.g. signal sequences, spacer or linker sequences, etc.

The invention also comprehends nucleic acid sequences that encode the proteins and polypeptides of the invention. Several exemplary nucleic acid sequences are provided herein. However, as is well known, due to the degeneracy of the nucleic acid triplet code, many other nucleic acid sequences that would encode an identical polypeptide could also be designed, and the invention also encompasses such nucleic acid sequences. Further, as described above, many useful variant forms of the proteins and peptides of the invention also exist, and nucleic acid sequences encoding such variants are intended to be encompassed by the present invention. In addition, such nucleic acid sequences may be varied for any of a variety of reasons, for example, to facilitate cloning, to facilitate transfer of a clone from one construct to another, to increase transcription or translation in a particular host cell (e.g. the sequences may be optimized for expression in, for example, corn, rice, yeast or other hosts), to add or replace promoter sequences, to add or eliminate a restriction cleavage site, etc. In addition, all genera of nucleic acids (e.g. DNA, RNA, various composite and hybrid nucleic acids, etc.) encoding proteins of the invention (or active portions thereof) are intended to be encompassed by the invention.

The invention further comprehends vectors, which contain nucleic acid sequences encoding the polypeptides of the invention. Those of skill in the art are familiar with the many types of vectors, which can be useful for such a purpose, for example: plasmids, cosmids, various expression vectors, viral vectors, etc.

Production of the nucleic acids and proteins of the invention can be accomplished in any of many ways that are known to those of skill in the art. The sequences may be synthesized chemically using methods that are well-known to those of skill in the art. Alternatively, nucleotide sequences may be cloned using, for example, polymerase chain reaction (PCR) and/or other known molecular biology and genetic engineering techniques Recombinant proteins may be made from a plasmid contained within a bacterial host such as *Escherichia coli*, in insect expression systems, yeast expression systems, plant cell expression systems, etc. Further, the nucleic acid sequences may be optimized for expression in a particular organism or system. To that end, the present invention also encompasses a host cell that has been transformed or otherwise manipulated to contain nucleic acids encoding the proteins and polypeptides of the invention, either as extra-chromosomal elements, or incorporated into the chromosome of the host. In particular, in the practice of the present invention, nucleic acid sequences encoding one or more of the cellulases (e.g. an entire "system" as described herein) may be introduced into plant cells, seeds, etc., to generate recombinant plants that contain the nucleic acids.

Plant transformation to incorporate one or more nucleic acids coding for one or more cellulase enzymes described herein can be accomplished by a variety of techniques known to those of skill in the art. Plant transformation is the introduction of a foreign piece of DNA, conferring a specific trait, into host plant tissue. Plant transformation can be carried out in a number of different ways; *Agrobacterium* mediated transformation, particle bombardment, electroporation and viral transformation.

Suitable examples of plants that may be transformed to include one or more cellulase enzymes or sets of enzymes include but are not limited to rice, corn, various grasses such as switchgrass, sugar cane, sorghum, pinus and eucalyptus, etc. Advantages of genetically engineering plants to contain and express the cellulase genes include but are not limited to the availability of the enzymes within the cell wall tissues (cellulosic fibers) and ready to be activated by high temperatures (e.g., heating to 70 or 80 C or more). Deposition of these enzymes produced by the plant cells and targeted to the apoplast, should largely overcome the recalcitrant nature of biomass.

The cellulases and/or cellulase enzyme systems of the invention may be used for the breakdown (catalysis) of cellulose in biomass from a wide variety of sources. Biomass comes in many different types, which may be grouped into four main categories: (1) wood residues (including sawmill and paper mill discards); (2) municipal paper waste; (3) agricultural residues (including corn stover and sugarcane bagasse); and (4) dedicated energy crops, which are mostly composed of fast growing tall, woody grasses. Cellulose-containing biomass from any of these or other sources may be acted upon by the enzymes and consolidated enzyme systems of the invention.

Generally, the breakdown of cellulose will be complete, i.e. the endproduct is glucose. This is especially true when a consolidated enzyme system that includes at least three different types of enzymes (for example, an endoglucanase, an exo-processive-endoglucanases, and a β-glucosidase) are employed. However, this need not always be the case. Depending on the goal of the reaction, only one enzyme may be utilized (e.g. an endoglucanase to generate randomly cleaved cellulose polymers); or only two enzymes may be utilized (e.g. an endoglucanase and an exo-processive-endoglucanases to generate dimeric disaccharides such as cellobiose), etc. Any desired grouping of the enzymes of the invention may be utilized to generate any desired endproduct that the enzymes are capable of producing from a suitable substrate. Further, one or more of the enzymes of the invention may be used in combination with other cellulases, or with enzymes having other types of activities. In one embodiment of the invention, a "system" could further include a yeast or other organism capable of fermenting glucose to e.g. ethanol.

The cellulases of the invention have very high temperature optima, an optimal temperature being the temperature at which an enzyme is maximally active (e.g. as an endoglucanase, an exo-processive-endoglucanases, or a β-glucosidase), as determined by a standard assay recognized by those of skill in the art. As described in the Examples section below, the lowest temperature optimum for an enzyme of the invention is about 85° C., and the highest temperature optimum is about 102° C. Further, the enzymes of the invention are thermally stable, i.e. they are capable of retaining catalytic activity at high temperatures (e.g. at their temperature maximum, or at temperatures that deviate somewhat from the maximum) for extended periods of time, for example, for at least for several hours (e.g. 1-24 hours), and in many cases, for several days (e.g. from 1-7 days or even longer). By "retain catalytic activity" we mean that the enzyme retains at least about 10, 20, 30, 40 or 50% or more of the activity displayed at the beginning of the extended time period, when measured under standard conditions; and preferably the enzyme retains 60, 65, 70, 75, 80, 85, 90, 95, or even 100% of the activity displayed at the beginning of the extended time period.

The enzymes of the invention are generally employed in reactions that are carried out at temperatures at or near those which are optimal for their activity. Some enzymes may be used over a wide temperature range (e.g. at a temperature that is about 50, 40, 30, 20, 10, 5 or fewer degrees lower than (below) the temperature optimum, and up to about 5, 10, 15, or more degrees greater than (above) the temperature optimum. For other enzymes, the range may be more restricted, i.e. they may display catalytic activity within a narrow temperature range of only less than about 10, or less than about 5, or fewer degrees of their optimal catalytic temperature. When carrying out a cellulose digestion reaction, the enzymes may be used one at a time sequentially (i.e. one enzyme is added, reaction occurs, and then another enzyme is added, with or without removal of the previous enzyme, and so on), or the reaction mixture may contain two or even all three of the enzymes (an enzyme system) may be added at the same time. When designing groups of enzymes to be included in an enzyme system, those of skill in the art will recognize that a suitable temperature at which all enzymes in the group are active will be selected as the temperature for reaction. Or, conversely, if it is desired to carry out a reaction at a particular temperature, enzymes with optimal activity at or near that temperature would be selected for inclusion in the set. For example, for a reaction to be carried out at 97° C., one might choose a set of enzymes that includes Termocel 5 (endocellulase, optimum=96° C.), plus Termocel 2 (exocellulase, optimum=98° C.), plus Termocel 7 (β-glucosidase, optimum=98° C.); whereas for a reaction that is to be carried out at 90° C., one might choose Termocel 6 (endocellulase, optimum=85° C.), plus Termocel 3 (exocellulase, optimum=94° C.), plus Terntocel 7 (β-glucosidase, optimum=92° C.). If an enzyme is used individually, the reaction may be carried out at a temperature near its optimum, or at which the enzyme retains sufficient activity to be useful. In addition, the selection of a reaction temperature may be based on other considerations, e.g. safety or other practical considerations of high temperature operations, or concerns about the cost of keeping a reaction mixture at a high temperature, the temperature used for preparing biomass for the reaction, the temperature of procedures that follow the reaction, etc. Generally, the degradation of cellulose will be carried out at a temperature in the range of from about 70 to about 95° C.

The invention also provides methods of use of the enzymes disclosed herein. The methods generally involve the used of at least three enzymes of the invention, at least one from each of the three classes endoglucanase, exo-processive-endoglucanases, and β-glucosidase. The three classes of enzymes act in concert to sequentially breakdown cellulose to glucose. The methods of the invention may be carried out for any purpose for which it is desirable to prepare glucose (or other products produced by the enzymes), and further metabolize into other chemicals, such as ethanol, xylitol, butanol, amino acids, glycol etc.

Generally, such methods are carried out by first pretreating a cellulose-rich feedstock by removing the lignin (usually through ball milling). The production of sugars (saccharification) of the pretreated cellulose is carried out by suspending the pretreated cellulose in a cellulase broth that contains suitable cellulase enzymes such as those disclosed herein. Generally, the reaction will be carried out at a temperature in the range of from about 70 to about 95 C, and the length of time for a reaction will be in the range of from about one hour to about six days. Reactions are carried out in media such as aqueous buffered to a suitable pH, e.g. in the range of from about pH 4 to about pH 9.

Thereafter, the desired products (e.g. glucose and cellobiose) may be harvested from the broth, or the reaction products may be further processed. For example, for the production of ethanol, fermentation of the glucose in the broth may be carried out by known conventional batch or continuous fermentation processes, usually using yeast. Ethanol may be recovered by known stripping or extractive distillation processes. This process is illustrated schematically in FIG. 14, which shows the steps of pretreating biomass to provide a source of cellulose; contacting the cellulose with one or more cellulase enzymes of the invention to hydrolyze cellulose to glucose, and fermenting the glucose to produce ethanol.

EXAMPLES

Example 1

Isolation and Characterization of Cellulases that Catalyze High-Temperature Thermo-Stable Bio-Consolidated Cellulose Breakdown Abstract Cellulose breakdown entails cooperative interaction of various cellulases by accessing and cleaving the recalcitrant cellulosic polymer. At high temperatures, most of the recalcitrant biomass polymers become enzymatically accessible because of intermolecular hydrogen bond disruption. Here, we describe a high-temperature operating thermo-stable cellulose enzyme system, consisting of endoglucanases, exoprocessive-endoglucanases and beta-glucosidases. Two catalytic types of cellulose cleaving enzymes was found: endoglucanases that randomly hydrolyze internal glycosidic bonds and exo-processive-endoglucanase, which split off cellobiose dimers. Finally, a third activity, β-glucosidase, reduces cellobiose into glucose molecules. The consolidated enzyme system operates optimally at temperatures above 85° C. and retains >85% of its enzymatic activity after a 5 day incubation at 90° C. Catalytic consolidation with high-temperatures is not additive but synergistic, accessing recalcitrant cellulose and hydrolyzing beta linkages above 85° C.

Introduction

Cellulose is an abundant biopolymer component of plant cell walls. Cellulose is a linear biopolymer of D-glucose, linked by β-1,4-glucosyl linkages. Cellulosic enzyme systems completely hydrolyze cellulose rendering glucose molecules. A cellulosic enzymatic system consists of multiple cellulases, endo-β-glucanase, cellobiohydrolase and β-glucosidase, which interact synergistically in producing glucose. Endoglucanases randomly hydrolyze the internal glycosidic bonds to decrease the length of the cellulose chain. Cellobiohydrolases are exo- or endo-processive enzymes that split off cellobiose of the shortened cellulose chains. Cellobiose is hydrolyzed by β-glucosidase to glucose.

Native cellulose molecules appear predominantly as crystalline cellulose, which shows a high degree of intermolecular hydrogen bonding explaining its remarkable stability and recalcitrance to enzymes. Thus disrupting crystal intermolecular hydrogen bonds through cellulose swelling and dissolution with high-temperature operating cellulases overcomes recalcitrance and result in enzymatic digestion of native cellulose.

Results

Isolation and Characterization of High-Temperature Operating and Thermostable Cellulases A series of ten high-temperature operating and thermostable cellulases were identified through bioinformatics driven searches of archeal and bacterial genomes. The corresponding genes were genetically manipulated to adapt expression to a laboratory tractable system (*Escherichia coli*) by codon optimization and usage controlled promoters. Individual proteins were expressed and isolated (purified) from *E. coli* crude extracts and analyzed for activity and other physical and chemical properties. Data presented in tabular form in FIG. 9 describes the eight enzymes isolated in this study.

Termocel 1 and 2, group into a class with similar physical and catalytic properties, they exhibit a molecular weight of 34,005 and 31,930 D, a pI of 4.8 and 4.77 and a net charge at pH 7 of −13.10 and −13.30, respectively. They appear to function through an exo-processive-endoglucanase cleaving pattern with a specific activity on Avicel of 63.4 and 8.1 U and on swollen cellulose of 13.6 and 2.2. U, respectively.

Termocel 3 and 4 differ slightly with a molecular weight of 51,930 and 59,980 D, a pI of 6.47 and 7.05 and a net charge at pH 7 of −3.60 and 0.30, respectively. These enzymes also seem not to overlap with their predicted mode of operation, one exoprocessive type and the other as a endoglucanase with specific activity on Avicel of 48.5 and 6.8 and on swollen cellulose of 8.4 and 2.2 U, respectively.

Termocel 5 and 6 fall in a third class with similar physical and catalytic properties. They exhibit a molecular weight of 38,226 and 31,818 D, a pI of 5.58 and 5.66 and a net charge at pH 7 of −6.60 and −5.00, respectively. They appear to function through an internal cleaving pattern (endoglucanase) with a specific activity on Avicel of 34.1 and 20.6 U and on swollen cellulose of 6.8 and 5.1 U respectively.

Termocel 7 and 8 are β-glucosidases with distinct physical properties but similar catalytic activity. They exhibit a molecular weight of 81,243 and 51,509 D, a pI of 5.38 and 5.84 and a net charge at pH7 of −16.90 and −9.10, respectively. They cleave cellobiose with a specific activity on pNPG of 69.4 and 60.9 U, respectively.

Termocel 9 and 10 are endocellulases that exhibit a molecular weight of 45,059 and 85,598 D, a pI of 6.16 and 7.80 and a net charge at pH 7 of −2.20 and 4.30, respectively. They have a specific activity on Avicel of 5.2 and 4.9 U and on swollen cellulose of 1.4 and 1.5 U respectively.

Mode of Operation

FIGS. 10 and 11 describe the mode of operations of all six cellulases. Termocel 1, 2 and 3 are cellulases that function by sequentially cleaving glucose residues of the non-reducing end of a polymeric substrate. FIG. 10 shows the sequential depolymerization breakdown products through capillary zone electrophoresis.

Termocel 4, 5 and 6 are cellulases that function by internally cleaving a multimeric substrate. FIG. 11 shows trimeric and dimeric breakdown products, indicating internal cleavage of the pentameric substrate.

High-Temperature Catalytic Operation

FIG. 12 shows the optimum temperature of operation of eight Termocels in tabular form. The highest optimum was found for Termocel 1 with and optimum of 102° C. and the lowest optimum was found to be Termocel 6 with 85° C. At 60° C., all Termocels lost at least 40% of their activity (except Termocel 4) and at 20° C. the Termocels operated with less than 20% of their optimum activity.

Among the beta-glucosidases, no significant differences between activity and temperature optimum were apparent. However, catalytic inactivation at lower temperatures (45 and 20° C.) to levels below 1% residual activity for Termocel 7 is remarkable.

Thermal Stability

Thermostability of the Termocels was evaluated to determine the working time frame with useful enzymatic activity at high-temperatures. Enzymes were incubated at 90° C. for up to 5 days and than assayed for CMC (endo-glucanase and exo-cellulase) or PNPG (beta-glucosidase) activity and results are reported as % of residual activity in FIG. 13. With the exception of Termocel 3, all enzymes retained over 80% of their initial enzymatic activity after a 5-day incubation period at 90° C.

Modes of Use

These high-temperature operating cellulases can be used in all processes in which cellulose degradation at high temperatures is desired. These applications include but are not restricted to food processing, feedstuff preparation, textile finishing and paper pulping. The consolidated enzyme system is useful to hydrolyze fibrous crystalline cellulosic biomass materials, at high temperatures with Termocel 1, 2, 3, 4, 5, 6, 7 and 8 to produce high-sugar containing fermentation broths. In addition the genes of the high-temperature operating enzyme system can be used in producing transgenic organisms capable of expressing one or more high-temperature operating and thermostable plant cell wall degrading enzymes.

Methods

Cloning

Genomic DNA of *Pyrococcus horikoshii* OT3 served as the PCR template for the amplification of the PHI 171 gene. Likewise, genomic DNA of *Thermotoga petrophila* RKU-1 served as PCR template for the cloning of the PetroA, PetroB, Tpet_0898 and Tpet_0952 genes. Primer sequences are shown in Table 1. Restriction sites were introduced (bold letters). The O-eglA, ZP and E1 genes were synthesized without using a DNA template; the codons of the three genes were also optimized according to the sequences of corn and rice genomes (FIGS. 1A, 4A and 6A). All gene segments generated were cloned into the N col and XbaI sites of the pBAD/Myc-His vector (Invitrogen), which carries a fusion sequence (GAACAAAAACTCA TCTCAGAAG AGGATCTGAAT-AGCGCCGTCGACCATCATCATCATCATCATCAT, SEQ ID NO: 17) encoding six histidine residues at the C-terminus of any protein expressed from the vetor (EQKLISEEDLN-SAVDHHHHHH, SEQ ID NO: 18) The expression plasmids were used to transform *Escherichia coli* TOP 10F' (Invitrogen). All constructs were verified by DNA sequencing.

TABLE 1

Oligonucleotide sequences used in this study.

| Primer | Sequence (5' → 3')[a] | SEQ ID NO: |
|---|---|---|
| Termocel 3 | ATATCCATGGAGGGGAATACTATTCTTAAAATC GTACTAAT (Forward) | 19 |
|  | ATGCTCTAGAAACCTGGGAGCCCTTCTTAAG (Reverse) | 20 |
| Termocel 5 | GAAACGCTCCTCCCTGTAGT (Forward) | 21 |
|  | ATGCTCTAGAAATTCTCTCACCTCCAGATCAAT AGAGA (Reverse) | 22 |
| Termocel 2 | AGGTGGGTAGTTCTTCTGATGG (Forward) | 23 |
|  | ATGCTCTAGAAATTTTACAACTTCGACGAAGAA GTCTTTGA (Reverse) | 24 |
| Termocel 7 | ATATCCATGGGAAAGATCGATGAAATCCTTTCA (Forward) | 25 |
|  | ATGCTCTAGAAATGGTTTGAATCTCTTCTCTC CC (Reverse) | 26 |
| Termocel 8 | AACGTGAAAAAGTTCCCTGAAG (Forward) | 27 |
|  | ATGCTCTAGAAAATCTTCCAGACTGTTGCTTT TG (Reverse) | 28 |

[a]Boldface indicates sequences complementary to the primers used to amplify the selectable markers.

Expression and Purification

An overnight growth of transformed *E. coli* strain containing the fusion protein vector was inoculated into fresh Luria-Bertani medium containing ampicillin. When the OD$^{600}$ reached 0.5-0.6, L-arabinose was added to a final concentration of 0.2%. The culture was allowed to grow for another 4-5 h at 37° C. and the cells were collected by centrifugation. The pellet was stored at −80° C. prior to further processes. Cells were disrupted by sonication and the cell debris was removed by centrifugation at 10,000×g for 20 min. The protein pool was then heat treated at 95° C. for 5 min, and denatured proteins were removed by centrifugation at 12,000×g for 20 min. The recombinant protein carrying a His6 tag was then purified by immobilized metal-chelate affinity chromatography (Qiagen). Hydrolysis of cellulose, hemicellulose and starch Hydrolysis of Avicel PH101, carboxymethyl cellulose (CMC), xylan from birch wood, α-cellulose, β-glucan barley, laminarin, lichenan, starch, swollen Avicel PH101, wheat arabinoxylan, xylan from beechwood and xylan from oat-spelt was measured spectrophotometrically by the increase of reducing ends at various temperatures and pH. The amount of reducing sugar ends was determined by the dinitrosalicyclic acid (DNS) method. The assay mix contained 10 µl of diluted enzymes, 30 µl of 100 mm sodium phosphate buffer, pH 6.0, and 20 µl of 0.5% (wt/vol) soluble substrates or 1% slurries (wt/vol) of insoluble substrates for 30 min or 1 hour. The reaction was terminated by adding 60 µl of DNS Solution. The absorbance of assay mix was read at 575 nm after the incubation at 100° C. for 5 min. The activity of enzymes as a function of temperature and pH was measured with CMC. Temperature gradient was achieved using PCR cycler (MJ Research). Phosphate/citrate buffers were used to generate pH gradient (ie., 2, 3, 4, 5, 6, 7, 8, 9.1).

For the thermostability assay, each enzyme was incubated at 90° C. An aliquot of enzymes was taken each day. Residual activity was measured with CMC.

Hydrolysis of p-nitrophetiol-β-D-glucoside

Activity of β-glucosidase was determined spectrophotometrically by monitoring the release of p-nitrophenol from the substrate p-nitrophenol-β-D-glucoside (Sigma) at various temperatures and pH. The assay mix contained 10 µl of diluted enzymes, 30 µl of 100 mm pH buffer, and 20 µl of 50 mM p-nitrophenol-β-D-glucoside for 10 min. The reaction was terminated by adding 120 µl of 1M $Na_2CO_3$. The absorbance of assay mix was read at 412 nm. Temperature and pH dependent activities and thermostability were measured as described above except that p-nitrophenol-β-D-glucoside was used as substrate.

Capillary Electrophoresis of Oligosaccharides

Capillary electrophoresis of oligosaccharides was performed on a BioFocus 2000 (Bio-Rad Laboratories,) with laser-induced fluorescence detection. A fused-silica capillary (TSPO50375, Polymicro Technologies) of internal diameter 50 µm and length 31 cm was used as the separation column for oligosaccharides. The samples were injected by application of 4.5 lbin-2 of helium pressure for 0.22 sec. Electrophoresis conditions were 15 kV/70-100 µA with the cathode at the inlet, 0.1 M sodium phosphate, pH 2.5, as running buffer, and a controlled temperature of 20° C. The capillary was rinsed with 1 M NaOH followed by running buffer with adip-cycle to prevent carryover after injection. Oligomers labeled with APTS were excited at 488 nm and emission was collected through a 520-nm band pass filter.

Biomass Substrate Specificity of Termocels

A table depicting the biomass substrate specificity of Termocels 1-8 is provided as FIG. 15.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A transformed host containing one or more recombinant cellulase enzymes comprising the amino acid sequence of SEQ ID NO: 2, wherein said host is corn.

2. A transformed host comprising one or more nucleic acid sequences encoding one or more recombinant cellulase enzymes comprising the amino acid sequence of SEQ ID NO: 2, wherein at least one of said nucleic acid sequences encoding the amino acid sequence of SEQ ID NO:2 is the nucleic acid sequence of SEQ ID NO:1.

3. A transformed host comprising one or more nucleic acid sequences encoding one or more recombinant cellulase enzymes comprising the amino acid sequence of SEQ ID NO: 2, wherein at least one of said nucleic acid sequences encoding the amino acid sequence of SEQ ID NO: 2 is the nucleic acid sequence of SEQ ID NO: 1, wherein said host is corn.

* * * * *

UNITED STATES PATENT AND TRADEMARK OFFICE
CERTIFICATE OF CORRECTION

| | | |
|---|---|---|
| PATENT NO. | : 8,847,031 B2 | Page 1 of 1 |
| APPLICATION NO. | : 13/003183 | |
| DATED | : September 30, 2014 | |
| INVENTOR(S) | : Prade et al. | |

It is certified that error appears in the above-identified patent and that said Letters Patent is hereby corrected as shown below:

In the Specification

At column 1, line 3, please insert the following paragraph:

--This invention was made with U.S. Government support under DOE Grant No. DE-FG36-06GO16107 awarded by the Department of Energy. The Government has certain rights in this invention.--

Signed and Sealed this
Thirtieth Day of December, 2014

Michelle K. Lee
*Deputy Director of the United States Patent and Trademark Office*